United States Patent [19]

Hobbs, Jr. et al.

[11] Patent Number: 5,047,519

[45] Date of Patent: Sep. 10, 1991

[54] ALKYNYLAMINO-NUCLEOTIDES

[75] Inventors: Frank W. Hobbs, Jr.; Anthony J. Cocuzza, both of Wilmington, Del.

[73] Assignee: E. I. Du Pont de Nemours and Company, Wilmington, Del.

[21] Appl. No.: 57,565

[22] Filed: Jun. 12, 1987

Related U.S. Application Data

[63] Continuation-in-part of Ser. No. 881,372, Jul. 2, 1986, abandoned.

[51] Int. Cl.$^5$ .............................................. C07H 1/00
[52] U.S. Cl. ...................................... 536/23; 536/24; 536/26; 536/27; 536/29; 544/243; 544/244
[58] Field of Search ..................... 536/23, 24, 28, 29, 536/26; 544/244, 243

[56] References Cited

FOREIGN PATENT DOCUMENTS 0251786 1/1988 European Pat. Off. ............. 536/27
0252683 1/1988 European Pat. Off. ............. 536/27
8403285 8/1984 World Int. Prop. O. .

OTHER PUBLICATIONS

Bergstrom et al., J. Am. Chem. Soc., vol. 98; 1587 (1976).
Langer et al., Proc. Natl. Acad. Sci., U.S.A., vol. 78; No. 11, pp. 6633–6637 (1981).
Draper, Nucleic Acids Research; vol. 12, No. 2, 989–1022 (1984).
Barr et al., J. Chem. Soc.; Perkins Trans. I, 1263–1267 (1978).
Bergstrom et al., J. Am. Chem. Soc.; vol. 100, 8106, (1978).
Vincent et al., Tetrahedron Letters, vol. 22; 945–947 (1981).
Robins et al., J. Org. Chem.; vol. 48, 1854–1862 (1983).
Sonogashira et al., Tetragedron Letters; No. 50, 4467–4470 (1975).
Edo et al., Chem. Pharm. Bull.; vol. 26, No. 12; 3843–3850 (1978).
Seela et al., Chem. Ber., vol. 111; 2925–2930 (1978).
Schram et al., J. Carbohydrates, Nucleosides and Nucleosides; vol. 2, No. 2, 177–184 (1975).
Bergstrom et al., J. Org. Chem., vol. 46; No. 7; 1423–1431 (1981).
Bergstrom et al., Nucleic Acids Research, vol. 8; 6213–6219 (1980).
Haralambidis et al., Nucleic Acids Research; vol. 15, No. 12, 4857–4876 (1987).
Gibson et al., Nucleic Acids Research; vol. 15; No. 16; 6455–6467 (1987).

*Primary Examiner*—Johnnie R. Brown
*Assistant Examiner*—James O. Wilson
*Attorney, Agent, or Firm*—George A. Frank

[57] ABSTRACT

Alkynylamino-nucleotides and labeled alkynylamino-nucleotides useful, for example, as chain terminating substrates for DNA sequencing are provided along with several key intermediates and processes for their preparation.

12 Claims, No Drawings

5,047,519

ALKYNYLAMINO-NUCLEOTIDES

REFERENCE TO RELATED APPLICATIONS

This application is a continuation-in-part of application Ser. No. 881,372, filed July 2, 1986, now abandoned and is related to U.S. Pat. No. 4,833,332 and Method, System and Reagents for DNA Sequencing, Ser. No. 07/057,566, filed concurrently herewith on June 2, 1987, by Prober et al. which is also a continuation-in-part of Ser. No. 881,372.

FIELD OF THE INVENTION

This invention pertains to alkynylaminonucleotides and especially to their use in preparing fluorescently-labeled nucleotides as chain-terminating substrates for a fluorescence-based DNA sequencing method.

BACKGROUND OF THE INVENTION

DNA sequencing is one of the cornerstone analytical techniques of modern molecular biology. The development of reliable methods for sequencing has led to great advances in the understanding of the organization of genetic information and has made possible the manipulation of genetic material (i.e. genetic engineering).

There are currently two general methods for sequencing DNA: the Maxam-Gilbert chemical degradation method [A. M. Maxam et al., Meth. in Enzym., Vol. 65, 499–559 (1980)] and the Sanger dideoxy chain termination method [F. Sanger. et al., Proc. Nat. Acad. Sci. USA, Vol. 74, 5463–5467 (1977)]. A common feature of these two techniques is the generation of a set of DNA fragments which are analyzed by electrophoresis. The techniques differ in the methods used to prepare these fragments.

With the Maxam-Gilbert technique, DNA fragments are prepared through base-specific, chemical cleavage of the piece of DNA to be sequenced. The piece of DNA to be sequenced is first 5'-end-labeled with $^{32}P$ and then divided into four portions. Each portion is subjected to a different set of chemical treatments designed to cleave DNA at positions adjacent to a given base (or bases). The result is that all labeled fragments will have the same 5'-terminus as the original piece of DNA and will have 3'-termini defined by the positions of cleavage. This treatment is done under conditions which generate DNA fragments which are of convenient lengths for separation by gel electrophoresis.

With Sanger's technique DNA fragments are produced through partial enzymatic copying (i.e. synthesis) of the piece of DNA to be sequenced. In the most common version the piece of DNA to be sequenced is inserted, using standard techniques, into a "sequencing vector", a large, circular, single-stranded piece of DNA such as the bacteriophage M13. This becomes the template for the copying process. A short piece of DNA with its sequence complementary to a region of the template just upstream from the insert is annealed to the template to serve as a primer for the synthesis. In the presence of the four natural deoxyribonucleoside triphosphates (dNTP's), a DNA polymerase will extend the primer from the 3'-end to produce a complementary copy of the template in the region of the insert. To produce a complete set of sequencing fragments, four reactions are run in parallel, each containing the four dNTP's along with a single dideoxyribonucleoside triphosphate (ddNTP) terminator, one for each base. ($^{32}P$-Labeled dNTP is added to afford labeled fragments.) If a dNTP is incorporated by the polymerase, chain extension can continue. If the corresponding ddNTP is selected, the chain is terminated. The ratio of ddNTP to dNTP's is adjusted to generate DNA fragments of appropriate lengths. Each of the four reaction mixtures will, thus, contain a distribution of fragments with the same dideoxynucleoside residue at the 3'-terminus and a primer-defined 5'-terminus.

The terms "terminator", "chain terminator" and "chain terminating substrate" are used interchangeably throughout to denote a substrate which can be incorporated onto the 3'-end of a DNA or RNA chain by an enzyme which replicates nucleic acids in a template-directed manner but, once incorporated, prevents further chain extension. In contrast, the natural deoxynucleotide substrates can be considered to be "chain propagating substrates".

The term "nucleoside" is used throughout to denote a heterocyclic base-sugar unit composed of one molecule of pyrimidine or purine (or derivatives thereof) and one molecule of a ribose sugar (or derivatives or functional equivalents thereof). The term "nucleotide" is used throughout to denote either a nucleoside or its phosphorylated derivative.

In both the Sanger and Mazam-Gilbert methods, base sequence information which generally cannot be directly determined by physical methods has been converted into chain-length information which can be determined, this determination can be accomplished through electrophoretic separation. Under denaturing conditions (high temperature, urea present, etc.), short DNA fragments migrate as if they were stiff rods. If a gel matrix is employed for the electrophoresis, the DNA fragments will be sorted by size. The single-base resolution required for sequencing can usually be obtained for DNA fragments containing up to several hundred bases.

To determine a full sequence, the four sets of fragments produced by either Maxam-Gilbert or Sanger methodology are subjected to electrophoresis in four parallel lanes. This results in the fragments being spatially resolved along the length of the gel. The pattern of labeled fragments is typically transferred to photo-sensitive film by autoradiography (i.e. an exposure is produced by sandwiching the gel and the film for a period of time). The developed film shows a continuum of bands distributed in the four lanes, often referred to as a sequencing ladder. The ladder is read by visually scanning the film (starting with the short, faster moving fragments) and determining the lane in which the next band occurs for each step on the ladder. Since each lane is associated with a given base (or combination of bases in the Maxam-Gilbert case), the linear progression of lane assignments translates directly into base sequence.

The Sanger and Maxam-Gilbert methods for DNA sequencing are conceptually elegant and efficacious but they are operationally difficult and time-consuming. Analysis of these techniques shows that many of the problems stem from the use of a single radioisotopic reporter. [A reporter can be defined as a chemical group which has a physical or chemical characteristic which can be readily measured or detected by appropriate physical or chemical detector systems or procedures. Ready detectability can be provided by such characteristics as color change, luminescence, fluorescence, or radioactivity; or it may be provided by the ability of the reporter to serve as a ligand recognition site to form specific ligand-ligand complexes which contain groups detectable by conventional (e.g., colorimetric, spectrophotometric, fluorometric or radioactive) detection procedures. The ligand-ligand complexes can be in the form of protein-ligand, enzymesubstrate, antibody-antigen, carbohydrate-lectin, proteincofactor, protein-effector, nucleic acid-nucleic acid or nucleic acid-ligand complexes.]

The use of short-lived radioisotopes such as $^{32}$P at high specific activity is problematic from both a logistical and a health-and-safety point of view. The short half-life of $^{32}$P necessitates the anticipation of reagent requirements several days in advance and prompt use of the reagent. Once $^{32}$P-labeled DNA sequencing fragments have been generated, they are prone to self-destruction and must be immediately subjected to electrophoretic analysis. The large electrophoresis gels required to achieve single base separation lead to large volumes of contaminated buffer leading to waste disposal problems. The autoradiography required for subsequent visualization of the labeled DNA fragments in the gel is a slow process (overnight exposures are common) and adds considerable time to the overall operation. Finally, there are the possible health risks associated with use of such potent radioisotopes.

The use of only a single reporter to analyze the position of four bases lends considerable operational complexity to the overall process. The chemical/enzymatic steps must be carried out in separate vessels and electrophoretic analysis must be carried out in four parallel lanes. Thermally induced distortions in mobility result in skewed images of labeled DNA fragments (e.g. the smile effect) which, in turn, lead to difficulties in comparing the four lanes. These distortions often limit the number of bases that can be read on a single gel.

The long times required for autoradiographic imaging along with the necessity of using four parallel lanes force a "snapshot" mode of visualization. Since simultaneous spatial resolution of a large number of bands is needed, very large gels must be used. This results in additional problems: large gels are difficult to handle and are slow to run, adding more time to the overall process.

Finally there is a problem of manual interpretation. Conversion of a sequencing ladder into a base sequence is a time-intensive, error-prone process requiring the full attention of a highly skilled scientist. Numerous attempts have been made to automate the reading and some mechanical aids do exist, but the process of interpreting a sequence gel is still painstaking and slow.

To address these problems, replacement of $^{32}$P/autoradiography with an alternative non-radioisotopic reporter/detection system has been considered. Such a detection system would have to be exceptionally sensitive to achieve a sensitivity comparable to $^{32}$P; each band on a sequencing gel contains on the order of $10^{-16}$ mole of DNA. One method of detection which is capable of reaching this level of sensitivity is fluorescence. DNA fragments could be labeled with one or more fluorescent labels (fluorescent dyes). Excitation with an appropriate light source would result in a characteristic emission from the label thus identifying the band.

The use of fluorescent labels as opposed to radioisotopic labels, would allow easier tailoring of the detection system to this particular application. For example, the use of four different fluorescent labels distinguishable on the basis of some emission characteristic (e.g. spectral distribution, life-time, polarization) would allow linking a given label uniquely with the sequencing fragments associated with a given base. With this linkage established, the fragments could be combined and resolved in a single lane and the base assignment could be made directly on the basis of the chosen emission characteristic.

So far two attempts to develop a fluorescence-based DNA sequencing system have been described. The first system, developed at the California Institute of Technology, has been disclosed in L. M. Smith, West German pat. Appl. #DE 3446635 A1 (1984); L. E. Hood et al., West German Pat. Appl. #DE 3501306 A1 (1985); L. M. Smith et al., Nucleic Acids Research, Vol. 13 2399–2412 (1985); and L. M. Smith et al., Nature, Vol. 321, 674–679 (1986). This system conceptually addresses the problems described in the previous section but the specifics of the implementation render Smith's approach only partially successful. For example, the large wavelength range of the emission maxima of the fluorescently-labeled DNA sequencing fragments used in this system make it difficult to excite all four dyes efficiently with a single monochromatic source. More importantly, the significant differential perturbations in electrophoretic mobility arising from dyes with different net charges make it difficult or impossible to perform single-lane sequencing with the set of dyes used in this system. These difficulties are explicitly pointed out by Smith et al.

In general, the methodology used to prepare the fluorescence-labeled sequencing fragments creates difficulties. For Maxam-Gilbert sequencing, 5'-labeled oligonucleotides are enzymatically ligated to "sticky ended", double-stranded fragments of DNA produced through restriction cleavage This limits one to sequencing fragments produced in this fashion. For Sanger sequencing, 5'-labeled oligonucleotides are used as primers. Four special primers are required. To use a new vector system one has to go through the complex process of synthesizing and purifying four new dye-labeled primers. The same thing will be true whenever a special primer is needed.

The use of labeled primers is inferior in other respects as well. The polymerization reactions must still be carried out in separate vessels. As in the Maxam-Gilbert and Sanger sequencing systems, effectively all fragments derived from the labeled primer will be fluorescently labeled. Thus, the resulting sequencing pattern will retain most of the common artifacts (e.g. false or shadow bands, pile-ups) which arise when enzymatic chain extension is interrupted by processes other than incorporation of a chain terminator.

In a second approach, W. Ansorge et al., J. Biochem. Biophys. Methods. Vol. 13, 315–323 (1986), have disclosed a non-radioisotopic DNA sequencing technique in which a single 5'-tetramethylrhodamine fluorescent label is covalently attached to the 5'-end of a 17-base oligonucleotide primer. This primer is enzymatically extended in four vessels through the standard dideoxynucleotide sequencing chemistry to produce a series of enzymatically copied DNA fragments of varying length. Each of the four vessels contains a dideoxynucleotide chain terminator corresponding to one of the four DNA bases which allows terminal base assignment from conventional electrophoretic separation in four gel lanes. The 5'-tetramethylrhodamine fluorescent label is excited by an argon ion laser beam passing through the width of the entire gel. Although this system has the advantage that a fluorescent reporter is used in place of a radioactive reporter, all of the disadvantages associated with conventional sequencing and with preparing labeled primers still remain.

Until now, no one has created a DNA sequencing system which combines the advantages of fluorescence detection with terminator labeling. If appropriate fluorescently-labeled chain terminators could be devised, labeled sequencing fragments would be produced only when a labeled chain terminator is enzymatically incorporated into a sequencing fragment, eliminating many of the artifacts associated with other labeling methods. If each of the four chain terminators needed to sequence DNA were covalently attached to a different distinguishable fluorescent reporter, it should be possible, in principle, to incorporate all four terminators during a single primer extension reaction and then to analyze the resulting sequencing fragments in a single gel lane. If such fluorescently-labeled chain terminators could be devised, these compounds would probably also be useful for other types of enzymatic labeling of nucleic acids. In particular, analogs of fluorescently-labeled chain terminators could be designed to use other, non-fluorescent, reporters or to serve as chain-propagating substrates for enzymes which replicate nucleic acids in a template-directed manner (e.g., reverse transcriptase, RNA polymerase or DNA polymerase). Introducing a reporter into DNA in a manner useful for sequencing is one of the most difficult nucleic acid labeling problems. Compounds and/or strategies developed for DNA sequencing are also likely to be applicable to many other labeling problems.

To be useful as a chain-terminating substrate for fluorescence-based DNA sequencing, a substrate must contain a fluorescent label and it must be accepted by an enzyme useful for sequencing DNA. Suitable substrate candidates are expected to be derivatives or analogs of the naturally-occurring nucleotides. Because of the expectation that a fluorescent label and a nucleotide will not fit into the active site of a replication enzyme at the same time, a well-designed substrate must have the fluorescent label separated from the nucleotide by a connecting group of sufficient length and appropriate geometry to position the fluorescent label away from the active site of the enzyme. The nature of the connecting group can vary with both the label and the enzyme used. For ease of synthesis and adaptability to variations in label and/or enzyme requirements however, it is most convenient to consider the connecting group as consisting of a linker which is attached to the nucleotide and to the fluorescent label.

In the design of fluorescently-labeled chain terminators for DNA sequencing, the linker must satisfy several requirements:

1) one must be able to attach the same or a functionally equivalent linker to all four bases found in DNA;

2) the linker must not prevent the labeled nucleotide from being utilized effectively as a chain terminating substrate for an enzyme useful for DNA sequencing;

3) the linker (plus optional spacer and label) must perturb the electrophoresis of oligonucleotides to which it is attached in a manner which is independent of the base to which it is attached;

4) the attachment of the linker to the base and the spacer or label must be stereoselective and regioselective to produce a single well-defined nucleotide substrate; and 5) the linker should preferably contain a primary or secondary amine for coupling with the label.

Although five different types of amine linkers have been disclosed for attaching labels to nucleotides and oligonucleotides (see below), none of these linkers meet all five of the requirements listed above for use in a chain terminating substrate useful in DNA sequencing.

Bergstrom et al., J. Am. Chem. Soc., Vol. 98, 1587 (1976), disclose a method for attaching alkene-amino and acrylate side-chains to nucleosides by Pd(II)-catalyzed coupling of 5-mercurio-uridines to olefins. Ruth PCT/US84/00279 discloses the use of the above side-chains as linkers for the attachment of reporters to non-enzymatically synthesized oligonucleotides. Langer et al., Proc. Nat. Acad. Sci. USA, Vol. 78, 6633 (1981), disclose the use of allylamino linkers for the attachment of reporters to nucleotides. The disadvantages of these linkers include the difficulty of preparing regioselectively the appropriate mercurial nucleotide precursors, the difficulty of separating the mixture of products generated by some of these nucleotide/olefin coupling reactions, and the potential lability of vinyl substituted nucleosides. Klevan et al., WO 86/02929, disclose a method for attaching linkers to the N4 position of cytidine and the N6 position of adenosine. The disadvantage of this method is that there is no analogous site in uridine and guanosine for attaching a linker.

Another potential linker which might satisfy the five requirements listed above is an alkynylamino linker, in which one end of the triple bond is attached to the nucleoside and the other end of the triple bond is attached to a group which contains a primary or secondary amine. To insure chemical stability, the amine should not be directly attached to the triple bond. Some methods of attaching alkyne groups to nucleosides have been disclosed (see below).

Barr et al., J. Chem. Soc., perkins Trans. I, 1263–1267 (1978), disclose the syntheses of 5-ethynyluridine 2'-deoxy-5-ethynyluridine, 5-ethynylcytosine, 5-ethynylcytidine, 2'-deoxy-5-ethynylcytidine and the α-anomers of the 2'-deoxyribonucleosides. The 2'-deoxyribonucleosides were prepared by constructing the heterocycles, coupling with a functionalized 2-deoxy sugar, separating the anomeric mixtures, and removing the protecting groups on the sugars.

Bergstrom et al., J. Am. Chem. Soc., Vol. 100, 8106 (1978), disclose the palladium-catalyzed coupling of alkenes with 5-mercuri or 5-iodo derivatives of uracil nucleosides. This method was reported to fail in analogous reactions of alkynes with uracil nucleoside derivatives.

Vincent et al., Tetrahedron Letters, Vol. 22, 945–947 (1981), disclose the synthesis of 5-alkynyl-2'-deoxyuridines by the reaction of 0-3',5'-bis(trimethylsilyl)deoxyuridine with alkynylzinc reagents in the presence of palladium or nickel catalysts [dichloro-bis(triphenylphosphine)palladium(II), dichloro-bis(benzonitrile)palladium(II) or dichloro(ethylene-(bis(diphenylphosphine))nickel(II)].

Robins et al., J. Org. Chem., Vol. 48, 1854–1862 (1983), disclose a method for coupling terminal alkynes, HC≡CR (R=H, alkyl, phenyl, trialkylsilyl, hydroxyalkyl or protected hydroxyalkyl), to 5-iodo-1-methyluracil and 5-iodouracil nucleosides (protected as their p-toluyl esters) in the presence of bis(triphenylphosphine)palladium(II) chloride and copper(I) iodide in warm triethylamine. When 3',5'-di-O-acetyl-5-iodo-2'deoxyuridine was reacted with hexyne, 4-(p-toluyloxy)butyne, 4-(tetrahydropyranyloxy) or 4-(trityloxy)-butyne, the major products were the cyclized furano[2,3-d]pyrimidin-2-ones rather than the desired alkynyluridines.

None of the above references discloses a method for attaching an alkynylamino linker to nucleosides. The methodology of Bergstrom fails, and that of Barr is not directly applicable. The catalysts used by Robins et al. and Vincent et al. have the potential to promote numerous undesirable side reactions (e.g., cyclization or intermolecular nucleophilic addition of the amine to an alkyne) when the alkyne contains an amino group. Coupling reactions have been reported only with iodonucleosides which contain an electron-deficient uracil base. Since Pd-catalyzed coupling reactions generally work best with electron-deficient aryl iodides, problems may be anticipated in coupling alkynes to any of the other three bases (which are all more electron-rich than uracil).

There remains a need for alkynylamino nucleotides and for methods permitting their preparation.

SUMMARY OF THE INVENTION

The compounds of this invention are alkynylamino-nucleotides having the structure:

$$\text{Nuc}—C\equiv C—R_1—NR_2R_3 \quad (I),$$

wherein $R_1$ is a substituted or unsubstituted diradical moiety of 1–20 atoms. $R_1$ can be straight-chained alkylene, $C_1$–$C_{20}$, optionally containing within the chain double bonds, triple bonds, aryl groups or heteroatoms such as N, O or S. The heteroatoms can be part of such functional groups as ethers, thioethers, esters, amines or amides. Preferably, $R_1$ is straight-chained alkylene, $C_1$–$C_{10}$; most preferably $R_1$ is —$CH_2$—. Substitutents on $R_1$ can include $C_1$–$C_6$ alkyl, aryl, ester, ether, amine, amide or chloro groups;

$R_2$ and $R_3$ are independently H, $C_1$–$C_4$ alkyl, or a protecting group such as acyl, alkoxycarbonyl or sulfonyl. Preferably $R_2$ is H, and $R_3$ is H or trifluoroacetyl;

Nuc (nucleotide) is $R_4$-Het (heterocyclic base:

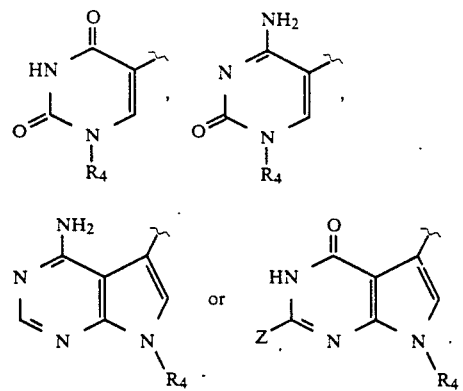

Z is H or $NH_2$; and
$R_4$ is a sugar or sugar-like moiety:

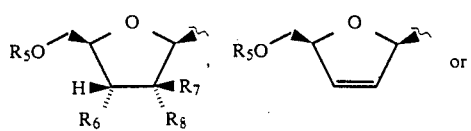

-continued

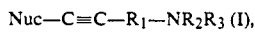

and wherein $R_5$ is H, $PO_3H_2$, $P_2O_6H_3$, $P_3O_9H_4$ or salts thereof,
and when $R_7$=$R_8$=H, the $R_6$=H, OH, F, $N_3$ or $NH_2$; or when $R_7$=H and $R_8$=OH. then $R_6$=H or OH; or when $R_7$=OH and $R_8$=H, then $R_6$=OH.

The labeled alkynylamino-nucleotides of this invention are structure I where $R_3$ is a reporter (label).

DETAILED DESCRIPTION OF THE INVENTION

The strategy used to incorporate reporters in the DNA sequencing fragments in a base-specific fashion is a critical feature of any DNA sequencing system. The use of the alkynylamino-nucleotides of this invention permit the modification of the Sanger methodology most advantageously by attaching a reporter (label) to an alkynylamino-nucleotide chain terminator. Although the reporter can be chosen from a wide variety of readily detectable groups (labels), for convenience the preferred approach is illustrated below using fluorescent reporters.

This approach offers a number of operational advantages. Most importantly, terminator labeling firmly links the attached reporter with the base-specific termination event. Only DNA sequencing fragments resulting from bona fide termination events will carry a reporter. This eliminates many of the artifacts observed in conventional sequencing. This approach also affords complete flexibility in the choice of sequencing vector since no special primers are involved. Automation is facilitated by the fact that the reporters are carried by four low molecular-weight reagents which can be selectively introduced in a single reaction.

There are no inherent operational disadvantages; the problems with this approach are encountered in the design stage. In general, the enzymes used for sequencing DNA are highly substrate selective and there is no reason a priori to expect to be able to make a nucleoside triphosphate with a covalently attached reporter that is an efficient chain-terminating substrate for a sequencing enzyme. It might be thought that attachment of a reporter to a substrate would cause sufficiently large changes in the steric and electronic character of the substrate to make it unacceptable to the enzyme or, even if accepted it would not be incorporated in the DNA chain. It has been found, however, that the small size of the alkynylamino linker of this invention and the ability to attach the alkynylamino linker to the 5-position of the pyrimidine nucleotides and the 7-position of the purine nucleotides provide labeled chain-terminating substrates that do not interfere excessively with the degree or fidelity of substrate incorporation.

The alkynylamino-nucleotides of this invention will be illustrated through the description of fluorescently-labeled alkynylamino nucleotide chain terminators. To delineate the structural scope and rationale of fluorescently-labeled alkynylaminonucleotides of this invention it is useful to break the labeled structure (I) into five components:

triphosphate-sugar-Het-C≡CR$_1$—NR$_2$-label (flourescent)

(i)       (ii)  (iii)       (iv)      (v)

(i) a triphosphate moiety, R$_5$
(ii) a "sugar", R$_4$
(iii) a heterocyclic base (Het),
(iv) a linker (—C≡CR$_1$NR$_2$—), and
(v) a fluorescent label, R$_3$.

(i) Triphosphate Moiety (R$_5$)

The triphosphate moiety or a close analog (e.g., α-thiotriphosphate) is an obligate functionality for any enzyme substrate, chain terminating or otherwise. This functionality provides much of the binding energy for the substrate and is the actual site of the enzyme-substrate reaction.

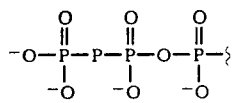

(ii) Sugar (R$_4$)

The "sugar" portion corresponds to the 2'-deoxyribofuranose structural fragment in the natural enzyme substrates. This portion of the molecule contributes to enzyme recognition and is essential for maintaining the proper spatial relationship between the triphosphate moiety and the heterocyclic base. To be useful for DNA sequencing, when the "sugar" is a ribofuranose, the 3'-α-position must not have a hydroxyl group capable of being subsequently used by the enzyme. The hydroxyl group must either be absent, replaced by another group or otherwise rendered unusable. Such sugars will be referred to as chain-terminating sugars. It is known that a number of modified furanose fragments can fulfill this requirement, including:

2'3'-dideoxy-β-D-ribofuranosyl [(a), F. Sanger et al., Proc. Nat. Acad. Sci. USA, Vol. 74, 5463–5467 (1977)], β-D-arabinofuranosyl, [(b) F. Sanger et al., Proc. Nat. Acad. Sci. USA, Vol. 74, 5463–5467 (1977)], 3'-deoxy-β-D-ribofuranosyl [(c), Klement et al., Gene Analysis Technology, Vol. 3, 59–66 (1986)].

3'-amino-2',3'-dideoxy-β-D-ribofuranosyl [(d), Z. G. Chidgeavadze et al., Nuc. Acids Res., Vol. 12, 1671–1686 (1984)], 2',3'-dideoxy-3'-fluoro-B-D-ribofuranosyl [(e), Z. G. Chidgeavadze et al., FEBS Lett., Vol. 183, 275–278 (1985)], and 2',3'-dideoxy-2',3'-didehydro-β-D-ribofuranosyl [(f), Atkinson et al., Biochem., Vol. 8, 4897–4904 (1969)].

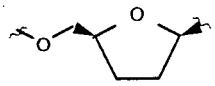 (a)

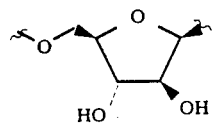 (b)

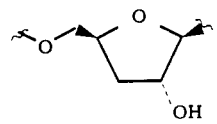 (c)

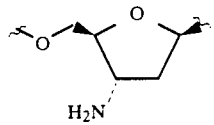 (d)

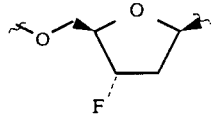 (e)

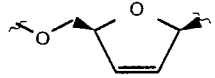 (f)

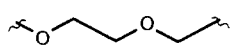 (g)

Acyclonucleoside triphosphates, (AcyNTP's), in which the so-called sugar is an acyclic group [e.g., 2-oxyethoxymethyl, (g)], can also be used as chain terminators in DNA sequencing by the Sanger methodology. The use of AcyNTP's as chain-terminating substrates has been demonstrated by carrying out conventional Sanger sequencing ($^{32}$P reporter) with the AcyNTP's substituting for the ddNTP's. The sequencing ladders produced with AcyNTP's were virtually identical to those produced with ddNTP's, except that a higher concentration of AcyNTP (approximately 10×) was required to obtain a similar distribution of DNA fragments. The AcyNTP's are effective with both DNA polymerase I (Klenow fragment) and AMV reverse transcriptase. The alkynylamino derivatives of AcyNTP's are therefore also expected to function as chain-terminating substrates.

The AcyNTP's have the advantage of being more easily synthesized than the ddNTP's. While the synthesis of ddNTP's is not a major problem in conventional sequencing, it is significant when structurally complex, fluorescently-labeled chain terminators are being prepared. The use of the 2-oxyethoxymethyl group as a sugar greatly simplifies reagent synthesis while maintaining acceptable performance.

Medicinal research has identified other sugar modifications which can be useful for DNA sequencing. For example, 3'-azido-2',3'-dideoxythymidine, [AZT; Mitsuya et al., Proc. Nat. Acad. Sci. USA,Vol. 82, 7096-7100 (1985)] and 9-[2'-hydroxy-1'-(hydroxymethyl)ethoxymethyl]guanine [DHPG; Aston et al., Biochem. Biophys. Res. Comm., Vol. 108, 1716-1721 (1982)] are two antiviral agents which are presumed to act by being converted to triphosphates which cause chain termination of DNA replication. Nucleoside triphosphates with such sugar units can also be useful for DNA sequencing.

(iii) Heterocyclic Base (Het)

The heterocyclic base functions as the critical recognition element in nucleic acids, acting as a hydrogen-bonding acceptor and donor in a particular spatial orientation. The heterocyclic base elements are essential for incorporation with the high fidelity necessary for accurate sequencing. This structural part is also the site of attachment of the linker.

Preferred heterocyclic bases include: uracil (h), cytosine (i), 7-deazaadenine (j), 7-deazaguanine (k), and 7-deazahypoxanthine (1). The unnatural 7-deazapurines can be employed to attach the linker without adding a net charge to the base portion and thereby destabilizing the glycosidic linkage. In addition, other heterocyclic bases which are functionally equivalent as hydrogen-bonding donors and acceptors can be used, e.g., 8-aza-7-deazapurines and 3,7-dideazaadenine can be used in place of 7-deazapurines and 6-azapyrimidines can be used in place of pyrimidines. (To simplify the nomenclature, the heterocyclic bases are named and numbered throughout as 7-deazapurines.)

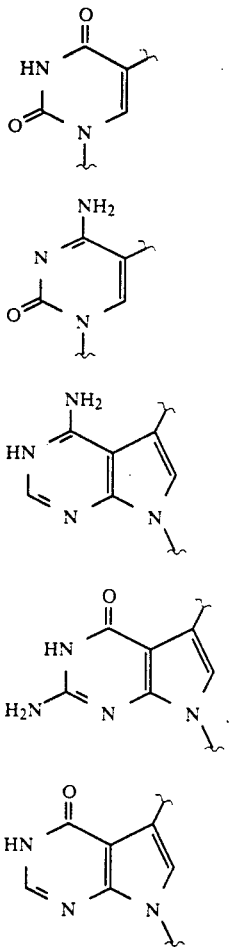

(h)
(i)
(j)
k (iv) Linker

The linker is an alkynylamino group in which one end of the triple bond is attached to an amine through a substituted or unsubstituted diradical moiety, $R_1$, of 1-20 atoms: the other end of the triple bond is covalently attached to the heterocyclic base at the 5-position for pyrimidines or the 7-position (purine numbering) for the 7-deazapurines. The amine nitrogen of the alkynylamino group is attached to a reactive functional group (e.g., carbonyl) on the fluorescent label. The linker must not significantly interfere with binding to or incorporation by the DNA polymerase. The diradical moiety can be straight-chained alkylene, $C_1$-$C_{20}$, optionally containing within the chain double bonds, triple bonds, aryl groups or heteroatoms such as N, O or S. The heteroatoms can be part of such functional groups as ethers, thioethers esters, amines or amides. Substituents on the diradical moiety can include $C_1$-$C_6$ alkyl, aryl, ester, ether, amine, amide or chloro groups. Preferably, the diradical moiety is straight-chained alkylene, $C_1$-$C_{10}$; most preferably the diradical is —$CH_2$—.

(v) Fluorescent Label ($R_3$)

The fluorescent label provides detectable, emitted radiation following excitation by absorption of energy from an appropriate source, such as an on ion laser. It is desirable to have unique, distinguishable fluorescent reporters for each DNA base encountered in sequencing applications.

A family of reporters useful for fluorescent labeling in a DNA sequencing method based on labeled chain-terminators can be derived from the known dye, 9-carboxyethyl-6-hydroxy-3-oxo-3H-xanthene [S. Biggs et al., J. Chem. Soc., Vol. 123, 2934–2943 (1923)]. This xanthene family has the general structure, 1,

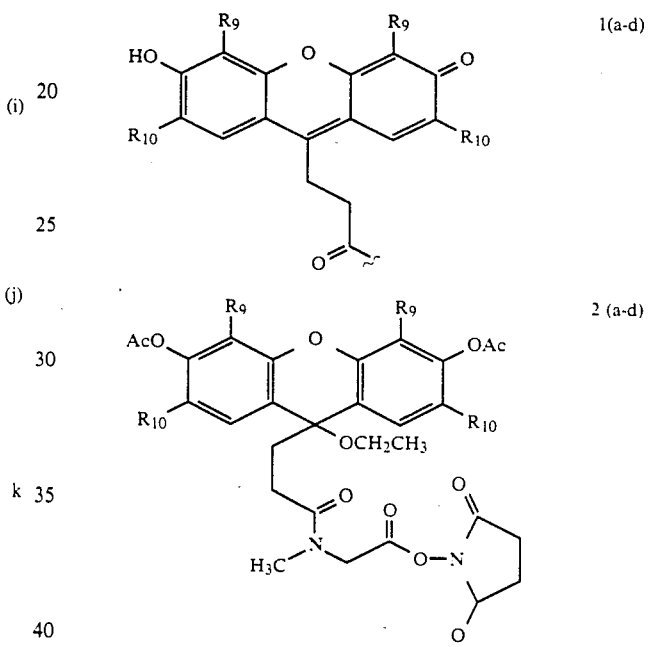

1(a-d)

2 (a-d)

1 where $R_9$ and $R_{10}$ include H, lower alkyl, lower alkoxy, halo, and cyano.

A preferred set of dyes suitable for DNA sequencing is structure 1, a) $R_9$=$R_{10}$=H, abs. 487 nm, emis. 505 nm; b) $R_9$=H, $R_{10}$=$CH_3$, abs. 494 nm, emis. 512 nm; c) $R_9$=$CH_3$, $R_{10}$=H, abs. 501 nm, emis. 519 nm; and d) $R_9$=$R_{10}$=$CH_3$, abs. 508 nm, emis. 526 nm. The instruments described by L. M. Smith L. E. Hood et al., L. M. Smith et al. and W. Ansorge et al. are capable of detecting sequencing fragments labeled with any one of these dyes at concentrations suitable for DNA sequencing, but these instruments are not capable or discriminating among the above set of four dyes. A method for discriminating the dyes and using this information to determine DNA sequences is disclosed in copending application Ser. No. 07/057,565, hereby incorporated by reference.

This application discloses a system for sequencing DNA, comprising a means for detecting the presence of radiant energy from closely-related yet distinguishable reporters, which are covalently attached to compounds which function as chain terminating nucleotides in a modified Sanger DNA chain elongation method. One distinguishable fluorescent reporter is attached to each of four dideoxynucleotide bases represented in Sanger DNA sequencing reactions, i.e., dideoxynucleotides of adenine guanine, cytosine and thymine. These reporter-labeled chain terminating reagents are substituted for unlabeled chain terminators in the traditional Sanger method and are combined in reactions with the corresponding deoxynucleotides, an appropriate primer, template, and polymerase. The resulting mixture contains DNA fragments of varying length that differ from each other by one base which terminate on the 3' end with uniquely labeled chain terminators corresponding to each of the four DNA bases. This new labeling method allows elimination of the customary radioactive label contained in one of the deoxynucleotides of the traditional Sanger method.

Detection of these reporter labels can be accomplished with two stationary photomultiplier tubes (PMT's) which receive closely-spaced fluorescent emissions from laser-stimulated reporters attached to chain terminators on DNA fragments. These fragments can be electrophoretically separated in space and/or time to move along an axis perpendicular to the sensing area of the PMT's. The fluorescent emissions first pass through a dichroic filter having both a transmission and reflection characteristic, placed so as to direct one characteristic (transmission) to one PMT, and the other characteristic (reflection) to the other PMT. In this manner, different digital signals are created in each PMT that can be ratioed to produce a third signal that is unique to a given fluorescent reporter, even if a series of fluorescent reporters have closely spaced emissions. This system is capable of detecting reporters which are all efficiently excited by a single laser line, such as 488 nm, and which have closely spaced emissions whose maxima usually are different from each other by only 5 to 7 nm. Therefore, the sequential base assignments in a DNA strand of interest can be made on the basis of the unique ratio derived for each of the four reporter-labeled chain terminators which correspond to each of the four bases in DNA.

Since these xanthene dyes contain reactive functional groups, the above copending application also discloses the design and preparation of reagents which are useful for attaching these dyes to the amino group of an alkynylamino linker. N-hydroxysuccinimide esters 2 (where $R_9$ and $R_{10}$ are as defined structure 1) are preferred examples of such reagents. During the preparation of 2, a sarcosine group is added to the basic dye structure to minimize side reactions. In the above copending application, this optional sarcosine group is referred to as a "spacer". Since only the preferred reagents are used herein, the fluorescent part of a labeled alkynylamino chain terminator is considered to include a sarcosine spacer. After the N-hydroxysuccinimide leaving group has been displaced by the amino group of the linker, the fluorescent dye (part structure 1) is liberated by treatment with concentrated ammonium hydroxide. N-hydroxysuccinimide esters are acylating agents which react selectively with highly-nucleophilic amino groups such as the ones present in the alkynylamino linkers described above. Control experiments have demonstrated that N-hydroxysuccinimide esters similar to 2 react much more slowly with the amino groups of the heterocyclic base than with the linker amino group. If reaction occurs to a small extent with the heterocyclic amino groups, it has been discovered that the resulting amides are hydrolyzed by the ammonium hydroxide treatment which liberates the dye. It is therefore possible to use esters such as 2 to attach selectively any reporter such as a fluorescent dye to the amino group of the linker without modifying the nucleotide in an unwanted fashion.

Fluorescently-labeled alkynylamino-nucleotide chain-terminators of this invention function as well in DNA sequencing with AMV reverse transcriptase as the corresponding substrates containing allylamino linkers which are disclosed in copending application Ser. No. 07/057,565. However, the compounds of this invention are easier to synthesize than the corresponding substrates containing allylamino linkers because the alkynylamino linkers are more easily attached to a preselected position on the various bases needed for DNA sequencing. In addition, the alkynylamino linkers can be attached to the nucleotides in higher yield. Finally, nucleotides containing an alkyne in conjugation with a heterocyclic ring are expected to be more stable than corresponding nucleotides containing an alkene. Suitable fluorescently-labeled chain terminators derived from alkynylamino-nucleotides are shown by structure 3, where Nuc, $R_1$–$R_4$ and $R_6$–$R_8$ are as defined above, $R_5=HO_9P_3$ and provided that when $R_8$ is H or OH, $R_6$ must not be OH.

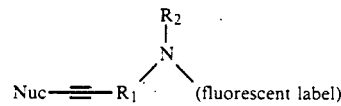

Scheme 1 describes methods for preparing the alkynylamino nucleotides of this invention where the sugar is a 2,3-dideoxyribofuranosyl group. These methods are compatible with all of the sugars of this invention. When combined with known methods for modifying the sugars of nucleotides, these methods can be used to prepare alkynylamino nucleotides in which the 2,3-dideoxyribofuranosyl group is replaced by the other sugars of the invention.

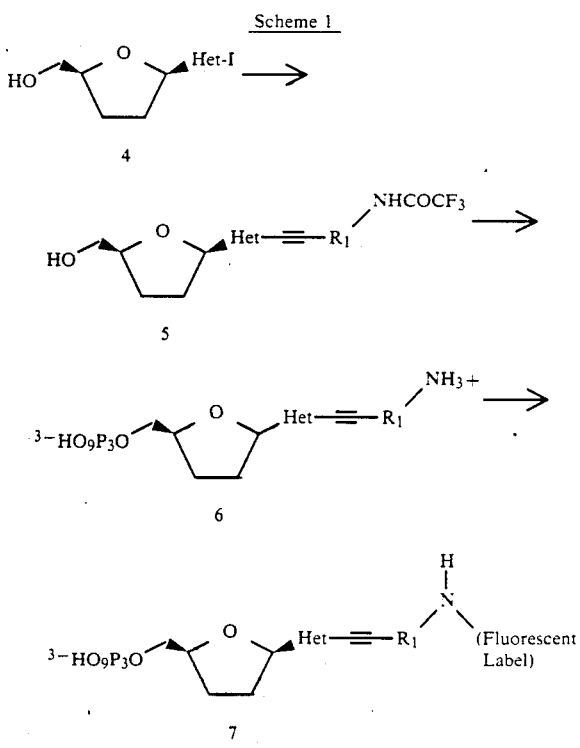

A variety of routes can be used to prepare the first key intermediates, the iodonucleosides (4). (In some instances, the corresponding bromonucleosides can be used in place of the iodonucleosides.)

5-Iodo-2',3'-dideoxyuridine can be prepared by treating 2',3'-dideoxyuridine [Pfitzer et al., J. Org. Chem., Vol. 29, 1508 (1964)] with ICl [Robins et al., Can. J. Chem., Vol. 60, 554–557 (1982)].

5-Iodo-2',3'-dideoxycytidine can be prepared by converting 2',3'-dideoxycytidine (Rayco Co.) to the corresponding 5-mercurio nucleoside [Bergstrom et al., J. Carbohydrates, Nucleosides and Nucleotides, Vol. 4, 257–269 (1977)] and then treating with iodine.

Although methods for preparing 7-deazaguanosine and 2'-deoxy-7-deazaguanosine are known, it has been shown [Seela et al., Chem. Ber., Vol. III, 2925–2930 (1978)] that electrophilic attack on 7-deaqzaguanines occurs at both the 7- and 8-positions. However, it has now been found that the desired 7-iodo-7-deazapurines can be obtained by treatment of 6-methoxy-2-thiomethyl-7-deazapurines with N-iodosuccinimide, followed by replacement of the 2-thiomethyl and 6-methoxy substituents as shown in Scheme 2 and described in Example 3. The use of N-iodosuccinimide for regioselective iodination of a 7-deazapurine ring system is unprecedented.

Scheme 2

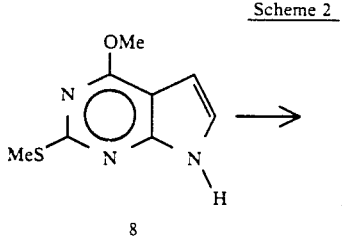

8

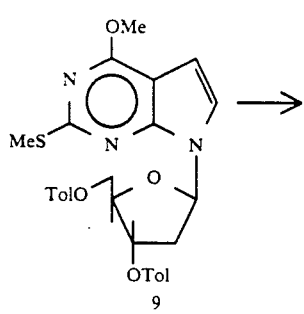

9

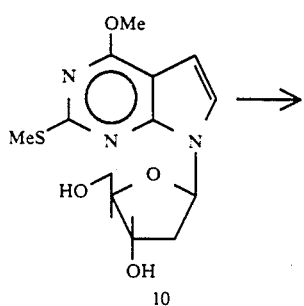

10

-continued
Scheme 2

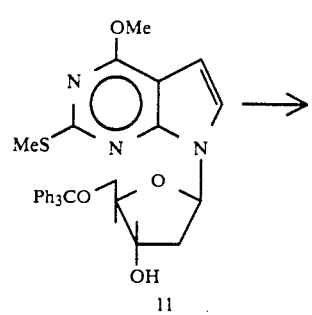

11

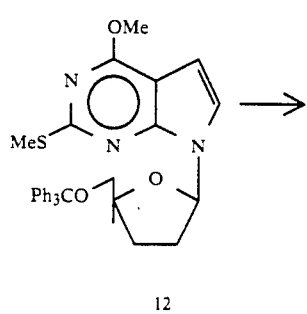

12

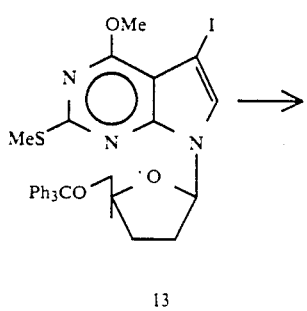

13

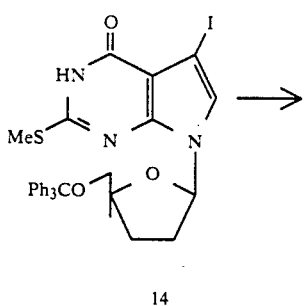

14

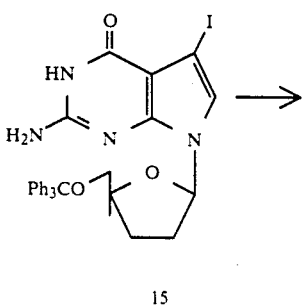

15

-continued
Scheme 2

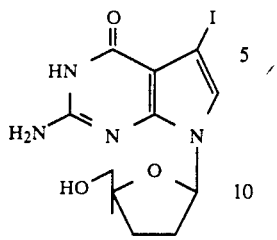

16

7-Iodo-2',3'-dideoxy-7-deazaadenosine can be prepared by deoxygenation of tubercidin, followed by mercuration/iodination (Scheme 3). The deoxygenation reactions were adapted from procedures disclosed by Moffatt et al., [J. Am. Chem. Soc., Vol. 95, 4016–4030 (1972)] and Robins et al., [Tetrahedron Lett., Vol. 25, 367–340 (1984)] to give an improved synthesis of 2',3'-dideoxy-7-deazaadenosine as shown in Scheme 3 and described in Example 4.

7-Iodo-7-deazaadenosine can be prepared by regioselective mercuration/iodination of tubercidin (7-deazaadenosine), as reported by Bergstrom et al., J. Carbohydrates, Nucleosides and Nucleotides, Vol. 5, 285–296 (1978) and Bergstrom et al., J. Org. Chem., Vol. 46, 1424 (1981).

Scheme 3

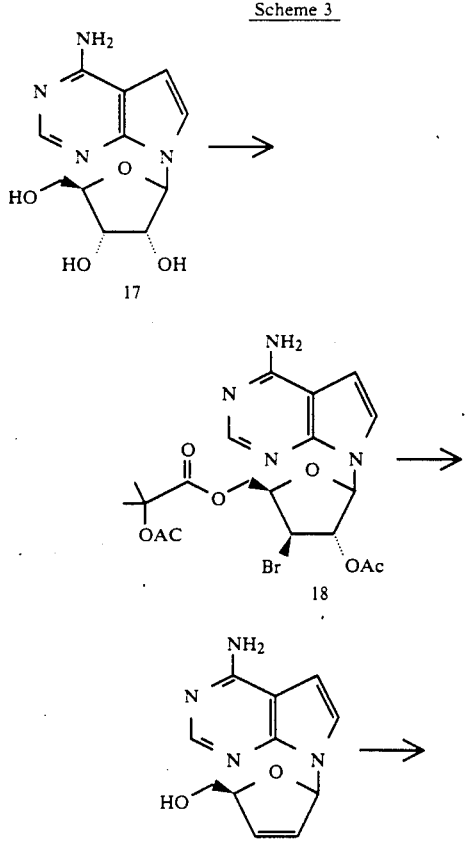

-continued
Scheme 3

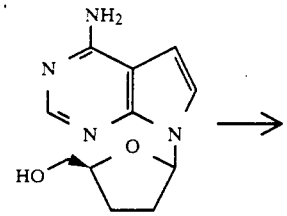

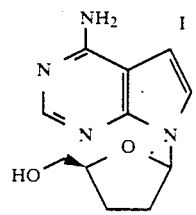

Alternative routes to 7-iodo-2',3'-dideoxy-7-deazaadenosine can be used which do not use tubercidin, an expensive fermentation product, as a starting material. These routes are shown in Schemes 4 and 5 and are described in Examples 5 and 6. In one of these routes, the problem of regioselectively introducing an iodine in the 7-position was solved by another unprecedented iodination. In this case, treatment of 6-chloro-7-deazapurine 32 with iodine monochloride afforded only the 7-iodo regioisomer 33.

Scheme 4

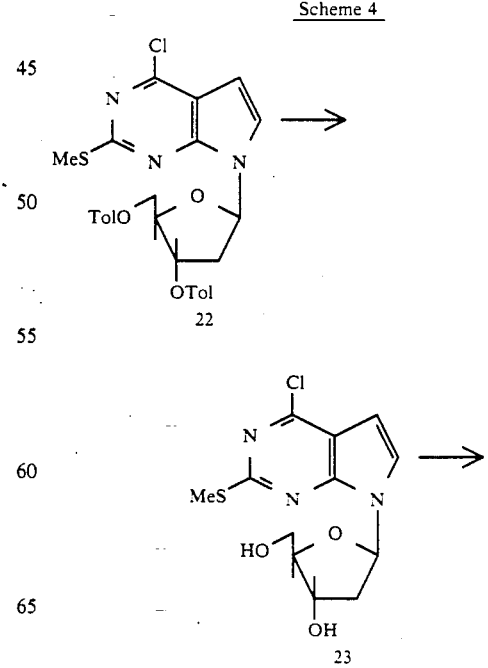

-continued
Scheme 4
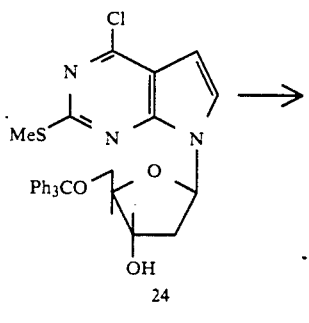
24
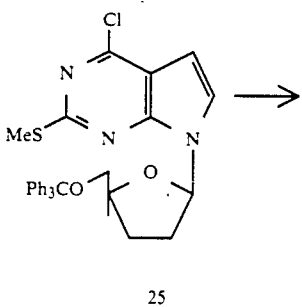
25
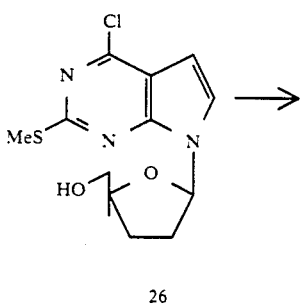
26
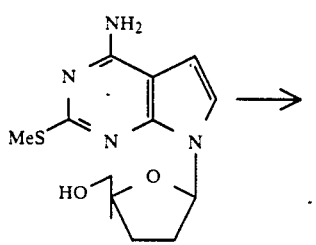
27
-continued
Scheme 4
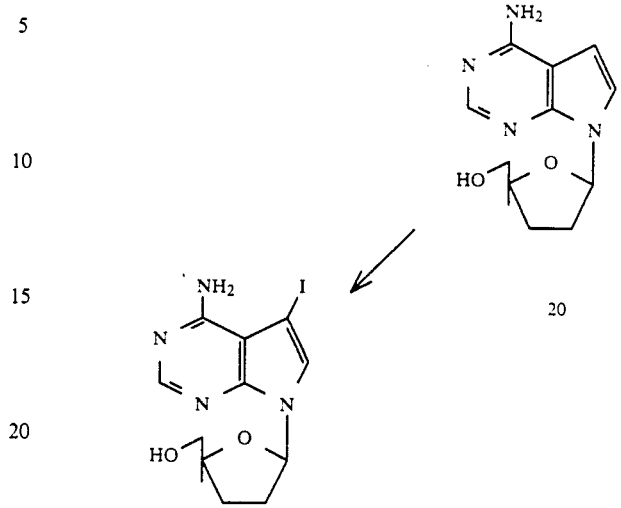
21 20
Scheme 5
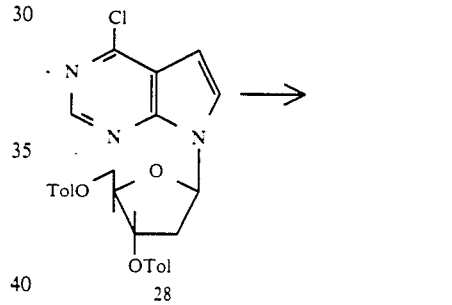
28
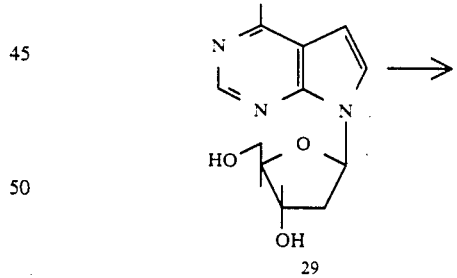
29
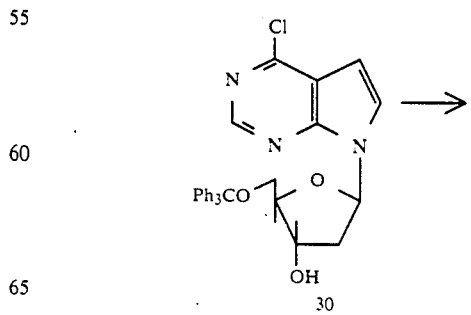
30

-continued
Scheme 5

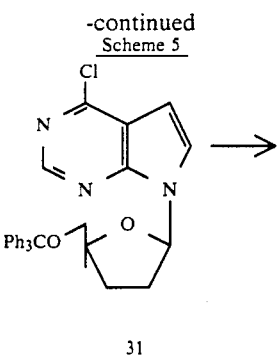

31

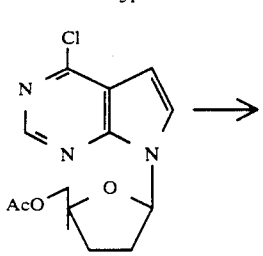

32

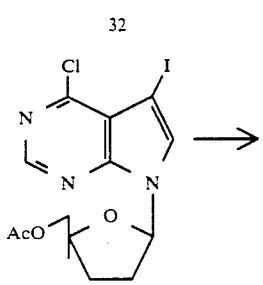

33

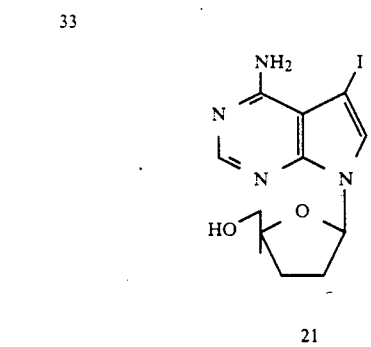

21

Although a method for coupling terminal alkynes with protected 5-iodouracil nucleosides using a Pd(II)/Cu(I) catalyst has been reported by Robins et al. [Tetrahedron Lett., Vol. 22, 421–424 (1981)], this method does not effect the desired coupling between alkynylamines (e.g., propargylamine) and the unprotected 5-iodopyrimidine or 7-iodo-purine nucleosides. The ability to use alkynylamines in direct coupling was highly desirable to provide directly compounds with an amine group for subsequent attachment of the fluorescent label. Similarly, a method using unprotected nucleosides was sought to provide a more direct route to the desired compounds by eliminating an otherwise unnecessary series of protection/deprotection reactions.

Under the conditions described below. alkynylamines were successfully coupled to a variety of halonucleosides in excellent Yields using a Pd(O)/Cu(I) catalyst. This coupling reaction was also successful when the alkynylamine nitrogen was protected by an acyl group such as acetyl and trifluoroacetyl, alkoxycarbonyl group such as 9-fluorenylmethyloxycarbonyl group, and a sulfonyl group such as p-toluenesulfonyl group. Unexpectedly, the number of carbon atoms between the amino group and the triple bond was found not to be critical in the procedure described below;

3-amino-1-propyne (propargylamine), 5-amino-1-pentyne,
N-(2-propynyl)trifluoroacetamide,
N-(4-pentynyl)-trifluoroacetamide and N-(11-dodecynyl)-trifluoroacetamide
were all successfully used in the coupling reaction.

The broad success of this Pd(O)/Cu(I) catalyzed coupling reaction is unexpected in view of the art. For example Bergstrom et al. [J. Am Chem. Soc. Vol. 100, 8106 (1978)] noted that alkYnes failed to couple to 5-mercuri or 5-iodo derivatives of uracil nucleosides using Pd catalysts. Also. Robins et al. [J. Org. Chem. Vol. 48, 1854–1862 (1983)] disclosed that the Pd(II)/Cu(I) catalyzed reactions of 3',5'-di-O-acetyl-5-iodo-2'-deoxyuridine frequently produced cyclized products. When the process described below is used, the coupling succeeds even with alkynylamines (such as 5-amino-1-pentyne) which have the potential to cyclize readily.

Typically, the alkynylamino-nucleosides of this invention can be prepared by placing the halonucleoside and Cu(I) in a flask, flushing with Ar to remove air, adding dry dimethylformamide, followed by addition of the alkynylamine triethylamine and Pd(O). The reaction mixture can be stirred for several hours, or until thin layer chromatography (TLC) indicates consumption of the halonucleoside. When an unprotected alkynylamine is used, the alkynylamino-nucleoside can be isolated by concentrating the reaction mixture and chromatographing on silica gel using an eluting solvent which contains ammonium hydroxide to neutralize the hydrohalide generated in the coupling reaction. When a protected alkynylamine is used, methanol/methylene chloride can be added to the reaction mixture, followed by the bicarbonate form of a strongly basic anion exchange resin. The slurry can be then stirred for about 45 min, filtered, and the resin rinsed with additional methanol/methylene chloride. The combined filtrates can be concentrated and promptly purified by flash-chromatography on silica gel using a methanol-methylene chloride gradient.

The alkynylamino-nucleotides of this invention are preferably prepared from 5-iodopyrimidine or 7-iodo-7-deazapurine nucleosides, but the analogous bromonucleosides can also be used. [The Pd(O)/Cu(I) catalyzed coupling reaction can also be used to introduce alkynylamine groups at other positions on the aromatic or heteroaromatic ring, provided only that the appropriate halonucleotide is available.]

Suitable alkynylamines for the Pd(O)/Cu(l) catalyzed coupling reaction are terminal alkynes wherein the triple bond is attached to an amine by a diradical moiety of 1–20 atoms. The diradical moiety can be straight-chain alkylene, ($C_1$–$C_{20}$ e.g., —$C_3H_6$—), or can contain double bonds (e.g., as in —CH=CHCH$_2$—). triple bonds (e.g., as in —C≡C—CH$_2$—) or aryl groups [e.g., (para —$C_6H_4$—, or para—$CH_2$—$C_6H_3$—]. The diradical can also contain heteroatoms such as N, O, or S in the chain as part of ether, ester, amine, or amido groups. Suitable substituents on the diradical moiety can include $C_1$–$C_6$ alkyl, aryl, ester, ether, amine, amide or chloro groups. Preferably, the diradical is a straight-chain alkylene ($C_1$–$C_{10}$); most preferably, the diradical is —$CH_2$—. Suitable substituents on the amine are lower alkyl ($C_1$–$C_4$) and protecting groups such as trifluoroacetyl. In general, the amine of the alkynylamine can be primary, secondary or tertiary. For use as a linker, however the alkynylamine is preferably a primary amine. The amine of the alkynylamine is usually protected because amine protection is required in the next step. The coupled product is also more readily purified when this amine is introduced in protected form. A trifluoroacetyl protecting group is preferred because it is easily removed after the coupling product is converted to the corresponding 5'-triphosphate. Generally, a 1.5-3.0 fold excess of alkynylamine (relative to iodonucleoside) can be used to insure complete conversion of the iodonucleoside to an alkynylamino-nucleoside.

Suitable solvents for the coupling reaction include polar solvents which dissolve the iodo- or bromonucleoside and do not decompose the Pd(O)/Cu(I) catalyst system. N,N-Dimethylformamide (DMF), acetonitrile, THF, dimethylsulfoxide (DMSO), hexamethylphosphoramide (HMPA), and alcohols can all be used; solvents which contain small amounts of water are also acceptable. Preferably, the solvent is DMF. Preferably, the concentration of the halonucleoside is 0.02-1.0M, most preferably 0.2-0.5M.

Suitable Pd catalysts are Pd(O) complexes, for example, tetrakis(triarylphosphine)Pd(O). Preferably, the Pd(O) catalyst is tetrakis(triphenylphosphine)Pd(O). The amount of Pd catalyst used is generally 1-25 mol % (based on iodonucleoside), preferably 5-15 mol %. The larger amounts of catalyst are used to conduct the reaction on a very small scale or to decrease the reaction time for coupling.

The Cu(I) co-catalyst is preferably a cuprous halide or pseudohalide (such as cuprous cyanide), most preferably CuI.

The mole ratio of Cu(I) co-catalyst to Pd(O) catalyst is more than 1.0 but less than 20. When a protected alkynylamine is used, the preferred mole ratio of Cu/Pd is 2. When the alkynylamine is unprotected, the unhindered basic nitrogen atom diminishes the catalytic activity of the copper. In this case, a Cu/Pd ratio of 5 is preferred. In either case, no reaction is observed at room temperature when Cu/Pd=1. The reaction rate generally increases as the Cu/Pd ratio increases. With protected alkynylamines and Cu/Pd ratios greater than 2, however, this increase is accompanied by increased side-products as indicated by TLC.

Triethylamine probably serves as an acid-scavenger in this reaction; other strongly basic amines can also be used. An excess of the unprotected alkynylamine can also serve as the acid-scavenger, but preferably triethylamine is added as well.

Protected alkynylamino nucleosides can be converted to the corresponding 5'-triphosphates by treatment with phosphorus oxychloride and then tri-n-butylammonium pyrophosphate [Ruth et al., Mol. Pharmacol., 415 (1981)]. The resulting crude triphosphate can be purified at this stage by ion-exchange chromatography by eluting with a volatile buffer such as triethylammonium bicarbonate. The desired nucleoside triphosphate is well-separated from side products, but lyophilization results in some removal of the protecting group on the linker nitrogen when this protecting group is a trifluoroacetyl group. Deprotection can be completed by treatment with 14% aqueous ammonia and the product can again be purified by ion exchange chromatography. Since the nature of the linker and its protecting group do not appear to block conversion to a triphosphate, this methodology can be used to prepare a wide variety of nucleoside mono-, di-, and triphosphates with protected or unprotected alkynylamino linkers.

After the preparation of the alkynylamino-nucleotides of this invention, the stage is set for the production of any desired reporter-labeled alkynylaminonucleotide of this invention.

The preferred set of four fluorescently-labeled alkynylamino-nucleotide chain-terminators (34-37) shown below is derived from alkynylamino-nucleotides of this invention. This set of labeled compounds is prepared as described in Example 19 by coupling N-hydroxysuccinimide esters 2 with alkynylamino nucleoside triphosphate 6, followed by ammonia deprotection.

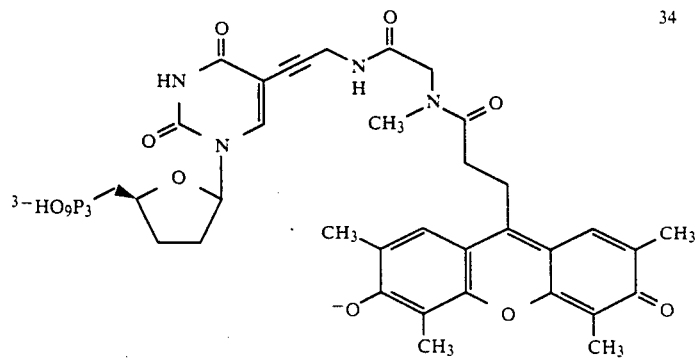

-continued

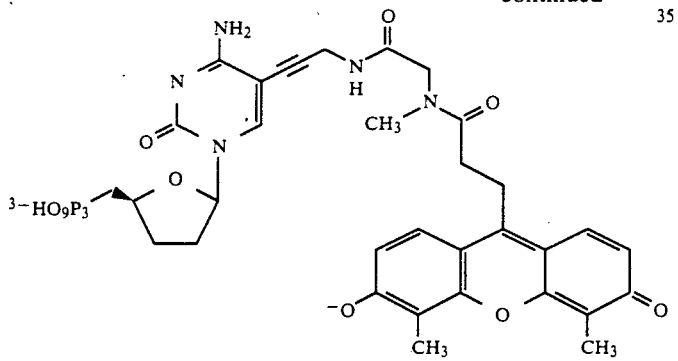

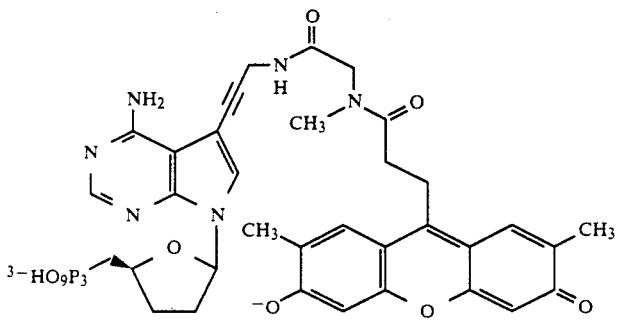

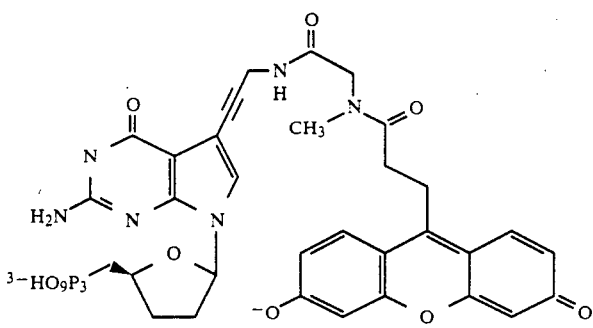

These four fluorescently-labeled chain terminators were used in place of the standard dideoxynucleotide chain terminators when sequencing DNA using AMV reverse transcriptase according to the procedure of Zagursky et al., Gene Analysis Techniques, Vol. 2, 89-94 (1985). The resulting fluorescentlylabeled sequencing ladders can be analyzed by an instrument designed to detect fluorescent molecules as they migrate during gel electrophoresis, preferably by the instrument described in U.S. Pat. No. 4,833,332, to Robertson et al., issued May 23, 1989. A system of this type using two filters is described in the copending Robertson et al. application, the contents of which are incorporated herein by reference. As described in Robertson et al., a pair of modules are positioned above and below a plane in which the reporter exciting light beam scans multiple lanes on an electrophoresis gel. Each channel contains reporter-labeled DNA fragments. Each detection module comprises a photomultiplier tube having a wide entrance area and a separate wavelength selective filter positioned between its PMT and the fluorescent species in the gel. These filters are interference filters having complementary transmission band characteristic which simulate the dichroic filter action. The filters permit the PMT's to generate signals that vary in amplitude in different senses as a function of the nature of the species. One filter largely passes the lower emission wavelengths and rejects the high emission wavelengths while the other filter does precisely the reverse. Transmission filters may be used with each interference filter to reject light from off axis angles greater than a predetermined angle. The wavelength filters have roughly complementary transmission vs. wavelength characteristics in the emission region of the four dyes, with the transition wavelengths occurring near the center of the species radiant energy spectra.

Detection of the fragments can also be carried out by the methods described by Smith et al., Hood et al., and Ansorge et al. Simultaneous analysis of four bases in a single lane using the information provided by this particular set of four fluorescent dyes, however, can only be done by means of the signal processing systems described in the above co-pending patent application.

In order to compare the results obtained by fluorescence detection with those obtained by standard sequencing techniques, this set of four labeled chain terminators has also been used to generate fluorescently-labeled sequencing fragments which also contain a $^{32}P$ reporter. (The $^{32}P$ reporter can be enzymatically incorporated during primer extension by adding labeled dNTP or by 5'-labeling of the primer with a kinase.) The resulting doubly-labeled sequencing ladders can be analyzed both by autoradiography and by a fluorescent gel reader. These fluorescently-labeled sequencing ladders are very similar and functionally equivalent to ladders produced by the standard dideoxynucleotide chain terminators except that all bands run approximately two bases slower. The relative intensity of various bands in these sequencing ladders is modified by the addition of a linker and dye but the modified chain terminal or does not appear to cause any bands to be missed. Under appropriate gel electrophoresis conditions, the linker and dye on these chain terminators do not cause any of the bands to migrate anomalously: a faster-moving band contains fewer bases than a slower-moving band. The spacing between adjacent bands with different dyes varies slightly depending on which dyes are next to each other. When using either fluorescent or radioactive detection under optimal conditions, these minor variations in relative band intensity and position do not interfere with the use of these chain terminators to sequence DNA.

The usefulness of alkynylamino nucleotides for the preparation of labeled chain terminating substrates for DNA sequencing is not limited to synthesis of only the set of four compounds shown above (34-37). Other combinations of sugars, bases and dyes have been assembled by means of an alkynylamino linker and these compounds are also useful for sequencing DNA.

In addition to their utility in preparing fluorescently-labeled chain terminators, the alkynylamino nucleotides of this invention are generally useful for attaching a variety of reporters to nucleotides or oligonucleotides. Because the most nucleophilic site in these molecules is the amino group introduced with the linker, a reporter containing an activated carboxylic acid (e.g., N-hydroxysuccinimide ester), an isocyanate, an isothiocyanate, an activated aryl halide (e.g., 1-fluoro-2,4-dinitrobenzene), or other electrophilic functional groups of appropriate reactivity, can be selectively attached to this nitrogen atom. The resulting labeled adducts can then be used in other applications to be described below.

Since the heterocyclic base subunit of nucleotides is used in the genetic code, the function of many nucleotides is often determined by the nature of the sugar subunit. Likewise, the utility of alkynylamino nucleotides depends specifically on what type of sugar subunit is present. This utility will be diminished if the alkynylamino linker and/or the reporter interfere with a needed function of the nucleotide. The alkynylamino linker-containing nucleotides of this invention have distinct advantages such as: the small steric bulk of the alkynylamino-linker minimizes perturbation of the nucleotide; positioning the linker on the 5-position of pyrimidine nucleotides and the 7-position of 7-deazapurine nucleotides eventually places the linker and reporter in the major groove when the nucleotide is incorporated into double-stranded DNA (this will serve to minimize interference with hybridization and other processes, which require that a double-stranded conformation be possible); and alkynylamino-nucleotides with a reporter attached are excellent substrates for AMV reverse transcriptase. Because functionally-related enzymes tend to interact with their substrates in similar ways, it is likely that these nucleotides will also be substrates for other useful enzymes (such as other reverse transcriptases, DNA polymerases, and RNA polymerases) which perform template-directed nucleotide polymerization.

The alkynylamino-nucleotides of this invention offer an attractive alternative for the chemical (non-enzymatic) synthesis of labeled 2'-deoxyoligonucleotides. Ruth International Application Number: PCT/US84/00279 discloses a method for incorporating a reporter group into a defined-sequence single-strand oligonucleotide. The method includes the preparation of appropriately protected and activated monomeric nucleotides which possess a linker with a protected amino group, use of these monomeric nucleotides to synthesize oligonucleotides chemically, followed by the selective attachment of a reporter to the linker amino group. The small size of the alkynylamino linkers and their location on the 5-position of pyrimidine nucleotides and the 7-position of 7-deazapurine nucleotides are expected to improve the performance of oligonucleotides containing them. An appropriately protected and activated monomer, (38), similar to one described by Ruth, could be prepared from commercially-available 5-iodo-2'-deoxyuridine by the Pd(O)/Cu(I) catalyzed attachment of an alkynylamino linker, followed by the selective dimethoxytritylation of the 5'-alcohol and finally conversion to a 3'-phosphoramidite with chloro(diisopropylamino)methoxyphosphine. This monomer and other similar alkynylamino-containing monomers are expected to be useful oligonucleotide synthesis and reporter attachment according to the methods described by Ruth. (The trifluoroacetyl protecting group on the linker nitrogen is removed by the basic and/or nucleophilic reagents normally used for final deprotection during the chemical synthesis of oligonucleotides.) If the reporter is unaffected by the reactions used in oligonucleotide synthesis, it could also be attached to the alkynylamino linker at an earlier stage.

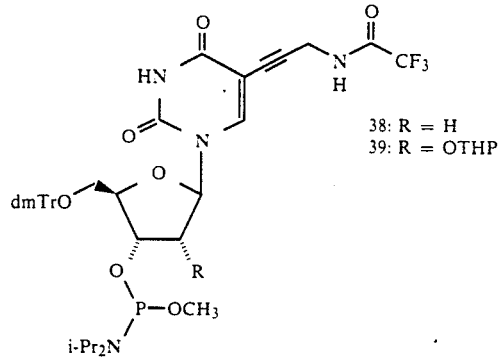

38: R = H
39: R = OTHP

Although chemical synthesis of oligoribonucleotides is currently not as efficient or useful as synthesis of 2'-deoxyoligonucleotides, an appropriate monomer, [(39), -O-tetrahydropyranyl (OTHP)] could be prepared and used to make labeled RNA.

In yet another application the enzymatic labeling of double-stranded nucleic acids can be facilitated through the use of the alkynylamino linkers. Langer et al., Proc. Nat. Acad. Sci. USA, 78, 6633 (1981), disclosed a nick-translation method for labeling double-stranded DNA with biotin reporters. An allylamino linker was used to attach biotin to the 5-position of 2'-deoxyuridine triphosphate and uridine triphosphate. The resulting biotinylated nucleotides are substrates for DNA and RNA polymerases. Alternatively, an alkynylamino linker could be used for biotin attachment or, in general, for the attachment of other reporters such as fluorescent dyes. Adenosine triphosphate analogs (40) and (41) with alkynylamino linkers could be prepared more easily than adenosine analogs with an allylamino linker. Nucleotide triphosphates analogs of (40) and (41) could be used for nick-translation labeling of DNA or RNA by the enzymatic procedures of Langer et al.

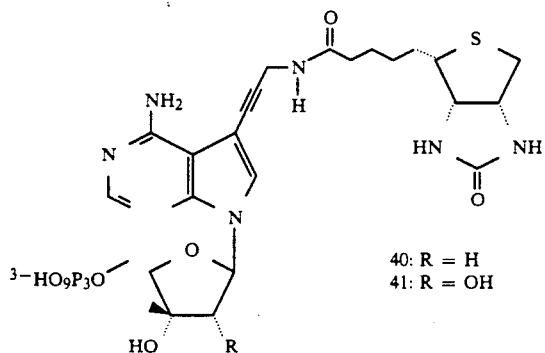

40: R = H
41: R = OH

The following Examples illustrate the invention.

All temperatures are in degrees centigrade. (25° refers to ambient or room temperature). All parts and percentages not otherwise indicated are by weight, except for mixtures of liquids which are by volume. The following abbreviations are employed: DMF—dimethylformamide; DMSO—dimethylsulfoxide; NHTFA—trifluoroacetamido-group; TEAB—triethylammonium bicarbonate; Tris—tris(hydroxymethyl)aminomethane; SF—succinylfluorescein; NMR—nuclear magnetic resonance spectrum; IR—infrared spectrum; UV—ultraviolet spectrum or detection; TLC—thin layer chromatography on silica gel; HPLC—high pressure liquid chromatography; GC—gas chromatography; mp—melting point; mp d—melting point with decomposition; bp—boiling point. In reporting NMR data, chemical shifts are given in ppm and coupling constants (J) are given in Hertz. All melting points are uncorrected. Ion exchange resins were washed with appropriate aqueous and organic solvents prior to use. The identity of all compounds described herein was established by appropriate spectroscopic and analytical techniques. Unless otherwise noted, purification by chromatography on silica gel was performed as described by Still et al., J. Org. Chem. 43, 2923–2926 (1978).

EXAMPLE 1

PREPARATION OF 5-(3-AMINO-1-PROPYNYL)-2',3'-DIDEOXYCYTIDINE 5'-TRIPHOSPHATE (42)

(Compound 42 is an example of structure 6 wherein Het is cytosine (i) and $R_1$ is —$CH_2$—. It is the immediate precursor to labeled chain terminator 35.)

A PREPARATION OF N-PROPARGYLTRIFLUOROACETAMIDE (43)

Propargylamine (24.79 g, 0.450 mole; Aldrich, 99%) was added dropwise over 1 h to methyl trifluoroacetate (69.19 g, 0.540 mole, 1.2 eq, Aldrich) at 0°. After stirring an additional hour at 0°, distillation though a 15 cm Vigreux column afforded 62.12 g (91%) of trifluoroacetamide 43 as a colorless liquid (bp 68.5°–69.5° at 11 torr). This material was homogeneous by NMR and GC and was used interchangeably with spectroscopically-identical material prepared by acylating propargylamine with trifluoroacetic acid anhydride.

$^1$H—NMR (CDCl$_3$): 6.85 (broad s, 1H, NHTFA), 4.17 (dd, J=5.6 and 2.5, 2H, CH$_2$), 2.35 (t, J=2.5, 1H, CH). IR (neat; cm$^{-1}$): 3300 (N—H), 3095 and 2935 (C—H), 2130 (acetylene), 1720 (C=O), 1550 (N—H), 1430, 1365, 1160, 1040, 998, 918, 857, 829, 772, and 725.

B. PREPARATION OF 5-IODO-2',3'-DIDEOXYCYTIDINE (44)

A solution of 2',3'-dideoxycytidine (2.11 g, 10 mmol, Raylo) and mercuric acetate (3.35 g, 10.5 mmol, Fisher) in 50 mL of methanol was refluxed for 19 h. The resulting white suspension was diluted with methanol (50 mL) and dichloromethane (100 mL). Iodine (3.05 g, 12 mmol) was added and the suspension was stirred at 25° until a clear purple solution was present After 4 h, the free base form of AG3 X4A resin (20 mL, 38 meq, Bio-Rad; a weakly basic polystyrene resin) was added and hydrogen sulfide was bubbled into the reaction for 15 min. Complete precipitation of mercury(II) was verified by TLC. The reaction was filtered though filter aid and the filter aid was washed with 1:1 methanol-dichloromethane. The filtrate was evaporated onto silica gel (10 g) and the loaded silica gel was placed on top of a 150 g silica gel column. Elution with 5%, 10% and 20% methanol in dichloromethane afforded 2.79 g (83%) of iodide 44 as a colorless crystalline solid. Two recrystallizations from boiling water afforded, after vacuum-drying at 50°, large, analytically-pure prisms (mp: d 178°).

$^1$H—NMR (DMSO-d$_6$): 8.50 (s, 1H, H$_6$), 7.73 (broad s, 1H, —NH$_2$a), 6.53 (broad s, 1H, —NH$_2$b), 5.86 (dd, J=6.5 and 2.1, 1H, H1'), 5.19 (t, 1H, 5'OH), 4.04 (m, 1H, H4'), 3.75 (ddd, J=12.1, 5.2, and 2.9, 1H, H5'a), 3.53 (dt, J=12.1 and 3.8, 1H, H5'b), and 2,3–1.7 (m, 4H, H2' and H3'). Calculated for C$_9$H$_{12}$N$_3$O$_3$I: C 32.07%, H 3.59%, N12.46%. Found: C 32.05%, H 3.80%, N 12.46%.

C. A GENERAL PROCEDURE FOR COUPLING AMINOALKYNES TO IODONUCLEOSIDES. PREPARATION OF 5-(3-TRIFLUOROACETAMIDO-1-PROPYNYL)-2',3'-DIDEOXYCYTIDINE (45).

A 50-mL, thee-necked flask was charged with iodocytidine 44 (770 mg, 2.00 mmol) and cuprous iodide (76.2 mg, 0.400 mmol, 0.20 eq; Aldrich, Gold Label). After flushing the flask with argon, dry dimethylformamide (10 mL, Aldrich) was added to produce a 0.2M solution of iodocytidine which contained suspended cuprous iodide. N-propargyltrifluoroacetamide (0.70 mL, 6.00 mmol, 3.0 eq) and triethylamine (0.56 mL, 4.00 mmol, 2.0 eq, stored over molecular sieves) were added via syringe. Tetrakis(triphenylphosphine)palladium(O) (231 mg, 0.20 mmol, 0.10 eq) was weighed into a vial in a dry box and added to the reaction mixture. The cuprous iodide dissolved, affording a yellow solution which gradually darkened over several hours. The reaction was allowed to proceed until TLC indicated that the starting material was completely consumed. After 4 h, the reaction was diluted with 20 mL of 1:1 methanol-dichloromethane and the bicarbonate form of AGI X8 resin (Bio-Rad, 2.0 g, ca. 6 eq; a strongly basic, anion exchange, polystyrene resin) was added. After stirring for about 15 min, evolution of gas ceased. After 30 min, the reaction mixture was filtered and the resin was washed with 1:1 dichloromethanemethanol. The combined filtrates were rapidly concentrated with a rotary evaporator. (Removal of dimethylformamide required about 10 min at 45° and 2 torr.) The residue was immediately purified by chomatography on 100 g of silica gel using 10%, 15% and 20% methanol in dichloromethane. Removal of solvent from the appropriate fractions afforded 651 mg (90%) of alkynylamine nucleoside 45 as a pale yellow crystalline foam which was homogeneous by TLC and NMR. The product from a similar preparation was established to be a hemi-hydrate by elemental analysis.

$^1$H—NMR (DMSO-$d_6$): 9.96 (broad s, 1H, NHTFA), 8.32 (s, 1H, H6), 7.76 (broad s, 1H, NH$_2$a), 6.78 (broad s, 1H, NH$_2$b), 5.88 (dd, J=6.5 and 2.5, 1H, H1'), 5.13 (t, J=5.1, 1H, 5'OH) 4.28 (d, J=5.0, 2H, —CH$_2$—), 4.04 (m, 1H, H4'), 3.73 (ddd, J=12.0, 5.0 and 3.1, 1H, H5'a), 3.53 (dt, J=12.1 and 4.0, 1H, H5'b), 2.3–1.7 (m, 4H, H2' and H3'). $^{19}$F—NMR (DMSO-$d_6$): −74.0 (s). UV (MeOH): maxima at 238.5 (17,100) and 295.5 (9,300). Calculated for $C_{14}H_{15}N_4O_4F_3 \cdot 1/2H_2O$: C 45.53, H 4.37, N 15.17. Found: C 45.56, H 4.52, N 15.26.

D. PREPARATION OF TRIS(TRI-N-BUTYLAMMONIUM) PYROPHOSPHATE.

Tetrasodium pyrophosphate decahydrate (4.46 g, 10 mmol) was dissolved in the minimum amount of water (about 50 mL) and passed though a column of AG50W X8 resin (100–200 mesh, 4×10 cm bed; a strongly-acidic, cation exchange, polystyrene resin) poured in water. The column was eluted with water and the eluent was collected in an ice-cooled flask until pH of the eluent approached neutrality. Tri-n-butylamine (Aldrich Gold Label, 7.1 mL, 30 mmol) was added to the eluent and the two phases were stirred vigorously until all of the amine dissolved. The resulting solution was lyophilized. The residue was co-evaporated twice with dry pyridine and once with dry dimethylformamide. The residue was dissolved in dry dimethylforamide (10 mL) and the resulting 1.0M solution was stored (for as long as one month) at 0° under argon until used.

E. A GENERAL PROCEDURE FOR CONVERTING PROTECTED ALKYNYLAMINO NUCLEOSIDES TO THE CORRESPONDING 5'-TRIPHOSPHATES AND REMOVING THE TRIFLUOROACETYL PROTECTING GROUP. PREPARATION OF 5-(3-AMINO-1-PROPYNYL)-2',3'-DIDEOXYCYTIDINE 5'-TRIPHOSPHATE (42)

Alkynylamino nucleoside 45 (361 mg, 1.00 mmol) was dissolved in trimethyl phosphate (2.0 mL, Aldrich Gold Label) while stirring under argon in an oven-dried flask. The solution was cooled to −10° and phosphorus oxychloride (0.093 mL, 1.00 mmol, Aldrich Gold Label) was added by syringe. After stirring the reaction mixture at −10° for 30 min, a second aliquot of phosphorus oxychloride (0.093 mL, 1.00 mmol) was added and the solution was allowed to warm slowly to 25° while stirring. Aliquots from the reaction mixture were quenched with 1N aqueous hydroxide and analyzed by HPLC. When conversion to the corresponding nucleotide monophosphate was at a maximum (in this case 100 min after the second addition of phosphorus oxychloride), the reaction mixture was added dropwise to a precooled (−10°) solution of tris(tri-n-butylammonium) pyrophosphate (6.0 mL of the above 1.0M solution in dry dimethylformamide). The solution was allowed to warm slowly to 25° while stirring under argon. After 100 min, the reaction solution was added slowly to a precooled (0°) solution of triethylamine (1.4 mL) in water (20 mL). The solution was stirred with ice-cooling for 15 min and then allowed to stand overnight at about 2°.

The volatiles were removed by vacuum evaporation at 25° and 0.5 torr. The residue was redissolved in water (75 mL) and applied to a column of DEAE-SEPHADEX ion exchanger (A-25-120, 2.6×65 cm bed) that had been equilibrated with: 1) pH 7.6, 1.0M aqueous TEAB (300 mL), 2) 1.0M aqueous potassium bicarbonate (300 mL), and 3) pH 7.6, 0.1M aqueous TEAB (300 mL). The column was eluted with a linear gradient of pH 7.6 aqueous TEAB from 0.1M (1 L) to 1.0M (1 L). The column was driven at 100 mL/h while collecting fractions every 12 min. The elution was monitored by absorbance at 270 nm (40 AUFS). The desired material eluted as a well-separated, major band near the end of the gradient (Fractions 73–80). The product-containing fractions were pooled, concentrated (at below 30°), and co-evaporated twice with absolute ethanol. The residue was taken up in water (20.4 mL) and lyophilized.

The intermediate product was taken up in water (12.5 mL) and concentrated ammonium hydroxide (12.5 mL) was added. After stirring for 3.5 h, the solution was stirred under aspirator vacuum for 2 h to remove the excess ammonia gas and then lyophilized. The residue was taken up in pH 7.6 0.1M aqueous TEAB (10 mL) and applied to a column of DEAE-SEPHADEX ion exchange resin (A-25-120, 1.6×55 cm bed) that had been prepared as described above. The column was eluted while collecting 6 mL fractions with a linear gradient of TEAB from 0.1M (280 mL) to 1.0M (280 mL). The product eluted as a single major peak. The fractions estimated to contain pure product (#39–45) were pooled, concentrated (at below 30°), co-evaporated with absolute ethanol (2×), and taken up in water (9.8 mL). The solution was assayed by Uv absorption and HPLC and then lyophilized.

A dilute solution of the product showed absorption maxima at 240 and 293.5 nm in pH 8.2 50 mM aqueous Tris buffer. Assuming an absorption coefficient for the product equal to that of the starting material (9,300), the yield of product, based on the absorption at 293.5 nm, was 0.32 mmol (32%). HPLC (Zorbax SAX, 0.2M pH 6.5 aqueous potassium phosphate, monitoring 270 nm) of the final product showed essentially a single peak (>99%).

$^1$H—NMR (D$_2$O): 8.57 (s, 1H, H6), 6.03 (dd, J=6.4 and 1.6, 1H, H1'), 4.42 (m, 2H, H4' and H5'a), 4.18 (ddd, J=12, 5.5 and 3, 1H, H5'b), 4.036 (s, 2H, —CH2—), 2.5–1.9 (m, 4H, H2' and H3,), plus counterion (triethylammonium) peaks. $^{31}$P—NMR (D$_2$O): −9.02 (d, J=20, 1P), −9.74 (d, J=20, 1P), −21.37 (t, J=20, 1P). UV (pH 8.2 aq Tris): maxima at 240 and 293.5 nm.

EXAMPLE 2

PREPARATION OF 5-(3-AMINO-1-PROPYNYL)-2',3'-DIDEOXYURIDINE 5'-TRIPHOSPHATE (46)

(Compound 46 is an example of structure 6 wherein Het is uracil (h) and R' is —CH$_2$—. It is the immediate precursor to labeled chain terminator 34.)

A. PREPARATION OF 5-IODO-2',3'-DIDEOXYURIDINE (47)

Dideoxyuridine (2.122 g, 10.0 mmol) was dissolved in 30 mL of warm methanol and, after cooling to 25°, iodine monochloride (4.06 g, 25 mmol, 2.5 eq, Fisher) in methanol (20 mL) was added over 5 min. The dark purple reaction mixture was heated in a 50° bath under nitrogen for 20 min and then immediately cooled in an ice-water bath. After standing without stirring for 165 min, the resulting precipitate was collected by filtration and washed with cold methanol (2×10 mL). Vacuum-drying overnight afforded 2.232 g (66%) of iodide 47 as off-white microcrystals. This material was used without further purification in the next reaction, but other preparations were purified by chomatography or recrystallization from boiling methanol (30 mL/g) to give white needles (mp d 160°–164°). NMR indicated that the crude precipitate was homogeneous, but also that the 5'-hydroxyl proton was very broad due to exchange catalyzed by trace impurities. Chomatographed or recrystallized materials afforded spectra in which this proton was, as usual, a sharp triplet.

$^1$H—NMR (DMSO-d$_6$): 11.60 (broad s, 1H, H3), 8.57 (s, 1H, H6), 5.90 (dd, J=2.0 and 6.6, 1H, H1'), 5.2 (broad s, 1H, 5'OH), 4.06 (m, 1H, H4'), 3.75 and 3.53 (m, 2H, H5'), 2.26, 2.02 and 1.84 (m, 4H, H2'and H3').

B. PREPARATION OF 5-(3-TRIFLUOROACETAMIDO-1-PROPYNYL)2',3'-DIDEOXYURIDINE (48)

Iodouridine 47 was coupled for 3 h to N-propargyltrifluoroacetamide following the general method given in Example 1C. Chomatography with a 0–5% methanol in dichloromethane gradient afforded material which was homogeneous by TLC, but which was difficult to dry. After co-evaporating the chomatographed product several times with chloroform and vacuum-drying, 536.5 mg of alkynylamino nucleoside 48 was obtained as a white foam. This material was homogeneous by TLC and was pure by NMR except for a small amount (39 mole%; corrected yield 66%) of chloroform.

$^1$H—NMR (DMSO-d$_6$): 11.61 (s, 1H, H3), 10.07 (distorted t, 1H, NHTFA), 8.35 (s, 1H, H6), 7.26 (s, 0.39H, CHCl$_3$), 5.89 (dd, J=6.6 and 3.2, 1H, H1'), 5.15 (t, J=5.2, 1H, 5'OH), 4.22 (broad d, 2H, —CH$_2$N—), 4.04 (apparent hept, J=3.5, 1H, H4'), 3.73 and 3.53 (m, 2H, H5'), 2.26, 2.03 and 1.84 (m, 4H, H2'and H3'). TLC (95:5 dichloromethane-methanol, two elutions, UV): Starting iodide 47, R$_f$=0.37; product 48, 0.28; catalysts, 0.95 and 0.80 plus slight streakiness.

C. PREPARATION OF 5-(3-AMINO-1-PROPYNYL)-2',3'-DIDEOXYURIDINE 5'-TRIPHOSPHATE (46).

Alkynylamino nucleoside 48 (0.30 mmol) was converted to the corresponding triphosphate and its trifluoroacetyl group was removed following the general procedure given in Example 1E. After addition of the second aliquot of phosphorus oxychloride, phosphorylation was allowed to proceed for a total of 210 min. Assuming an absorption coefficient for the product equal to that of the starting material (13,000), the yield of triphosphate 46, based on its UV absorption at 291.5 nm, was 18%.

EXAMPLE 3

PREPARATION OF 7-(3-AMINO-1-PROPYNYL)-2',3'-DIDEOXYGUANOSINE 5'-TRIPHOSPHATE (49)

(Compound 49 is an example of structure 6 wherein Het is 7-deazaguanine (k) and R$_1$ is —CH$_2$—. It is the immediate precursor of labeled chain terminator 37.)

A. PREPARATION OF 6-METHOXY-2-METHYLTHIO-9-(3,5-DI-O-p-TOLUOYL-2-DEOXY-β-D-RIBOFURANOSYL)-7-DEAZAPURINE (9)

6-Methoxy-2-methylthio-7-deazapurine (8, 9.2 g, prepared following the procedure of F. Seela et al., Chem. Ber., Vol. 111, 2925 (1978)) was azeotropically dried by dissolving in 150 mL of dry pyridine and evaporating to dryness at 30°–35°. This material was suspended in 450 mL of dry acetonitrile at room temperature under nitrogen and sodium hydride (2.16 g of a 60% suspension in oil) was added with stirring. After 45 min, 1-chloro-2-deoxy-3,5-di-O-p-toluoyl-α-D-ribofuranose (18.6 g, prepared following the procedure of M. Hoffer, Chem. Ber., Vol. 93, 2777 (1960)) was added in thee equal portions over a 20 min. After stirring the reaction mixture for an additional 45 min at room temperature, acetic acid (1 mL) and dichloromethane (300 mL) were added. The mixture was suction filtered though a pad of filter-aid, and the filtrate was evaporated to dryness. The residue was dissolved in benzene and this solution was washed with water (2×) and brine (1×). After drying the organic layer over sodium sulfate and evaporating, the residue was dissolved in methanol (400 mL) and allowed to crystallize affording 19.24 g (73.8%) of ribosylated product 9 as colorless crystals (mp 106°–107°).

$^1$H—NMR (CDCl$_3$): 2.42 (s, 3H, toluoyl CH$_3$), 2.44 (s, 3H, toluoyl CH$_3$), 2.64 (s, 3H, SCH$_3$), 2.70 and 2.89 (m, 2H, H2'), 4.08 (s, 3H, OCH$_3$), 4.56 (m, 1H, H3'), 4.65 (m, 2H, H5'), 5.74 (m, 1H, H4'), 6.44 (d, J=4, 1H, H7), 6.77 (dd, J=8 and 6, 1H, H1'), 7.05 (d, J=4, 1H, H8) and 7.25 and 7.95 (m, 8H, toluoyl H). Recrystallization of a sample of the above material from methanol containing a small amount of dichloromethane afforded crystals of mp 109°–110°.

B. PREPARATION OF 6-METHOXY-2-METHYLTHIO-9-(2-DEOXY-β-D-RIBOFURANOSYL)-7-DEAZAPURINE (10)

A suspension of ester 9 (19 g) and the hydroxide form of REXYN 201 resin (38 g; a strongly basic. anion exchange, polystyrene resin) in 600 mL of methanol was refluxed for 1.5 h under nitrogen. The hot suspension was suction filtered to remove the resin and the filtrate was evaporated to dryness. The solid residue was dissolved in ether (450 mL) and, after 10 min, the solution was filtered though a pad of filter aid to remove a small amount of a colored impurity. The solution was seeded with crystals of the desired product obtained from a previous reaction and allowed to stand overnight at 25°. Crystalline diol 10 was collected by filtration and the mother liquor was concentrated to afford a second crop. Each crop was washed thoroughly with ether and dried to afford a total of 8.43 g (78.0%) of diol 10 as colorless crystals (mp 129°–130°).

$^1$H—NMR (DMSO-d$_6$) 2.21 and 2.55 (m, 2H, H2'), 2.56 (s, 3H, SCH$_3$), 3.53 (m, 2H, H5'), 3.82 (m, 1H, H3'), 4.02 (s, 3H, OCH$_3$), 4.36 (m, 1H, H4,), 4.90 (t, J=5.5, 1H, 5'OH), 5.30 (d, J=5.5, 1H, 3'H), 6.48 (d, J=4, 1H, H7), 6.55 (dd, J=.8 and 6, 1H, H1'), 7.48 (d, J=1H. 1H, H8). Recrystallization of a sample of this material from dichloromethane containing a small amount of methanol afforded crystals of mp 130°–131°.

C. PREPARATION OF 6-METHOXY-2-METHYLTHIO-9-(5-O-TRIPHENYLMETHYL-2-DEOXY-β-D-RIBOFURANOSYL)7-DEAZAPURINE (11)

Diol 10 (7.2 g), was azeotropically dried by dissolving in dry pyridine and evaporating the solution to dryness at 35°. The residue was dissolved in dry pyridine (100 mL) and triphenylmethyl chloride (8.0 g), triethylamine (4.0 mL), and 4-(dimethylamino)pyridine (300 mg) were added. After heating the reaction mixture at 65° under nitrogen for 30 min, a second addition of triphenylmethyl chloride (1.0 g) was made and heating was continued for 16.5 h. After cooling, the reaction mixture was concentrated and the residue was partitioned between dichloromethane and water. The aqueous layer was extracted with dichloromethane and the combined organic layers were washed with 0.3N hydrochloric acid, aqueous sodium bicarbonate, and brine. After drying over sodium sulfate and concentrating, purification of the crude product by chomatography on silica gel with 0%, 1%, 1.5% and 2% methanol in dichloromethane afforded 12.1 g (94.5%) of monotrityl ether 11 as a colorless glass.

$^1$H—NMR (CDCl$_3$): 2.58 (s, 3H, SCH$_3$), 2.42 and 2.62 (m, 2H, H2'), 3.37 (m, 2H, H5'), 4.04 (m, 1H, H3'), 4.08 (s, 3H, OCH$_3$), 4.60 (m, 1H, H4'), 6.40 (d, J=4, 1H, H7), 6.68 (apparent t, J=7, 1H, H1'), 7.00 (d, J=4, 1H, H8), 7.27 and 7.43 (m, 15H, trityl H). This data was obtained from a different batch of 11 prepared as described above.

D. PREPARATION OF 6-METHOXY-2-METHYLTHIO-9-(5-O-TRIPHENYLMETHYL-2,3-DIDEOXY-β-D-RIBOFURANOSYL)7-DEAZAPURINE (12)

A solution of trityl ether 11 (12.1 g), 4-dimethylaminopyridine (9.2 g), and phenyl chlorothionocarbonate (7.5 mL, Aldrich) in dry dichloromethane (220 mL) was stirred at 25° for 2 h under nitrogen. Since TLC analysis indicated that the reaction was incomplete, phenyl chlorothionocarbonate (4.0 mL) was added and the reaction mixture was stirred for an additional 1 h. The solution was diluted with dichloromethane (280 mL) and was washed sequentially with 0.5N hydrochloric acid (500 mL), 0.5N sodium hydroxide (500 mL), and brine. The organic layer was dried over sodium sulfate and evaporated to dryness.

The resulting crude thionocarbonate was dissolved in dry toluene (350 mL) and azoisobisbutyronitrile (350 mg) and tri-n-butyltin hydride (10 mL) were added. The resulting solution was heated at 100°-105° for 10 min. After cooling, the solution was diluted with a little ether and was shaken with 10% aqueous potassium fluoride (350 mL). The two layers were filtered though a pad of filter aid (to remove a dark sludge) and separated. The organic layer was washed with 0.75N potassium hydroxide and brine, dried over sodium sulfate and concentrated. Chomatography of the resulting oil on silica gel with 1:1 dichloromethane-ether and then with dichloromethane afforded 9.93 g (84.5%) of dideoxynucleoside 12 as a colorless solid (mp 122°-124°).

$^1$H—NMR (CDCl$_3$): 2.10, 2.33, and 2.43 (m, 4H, H2'and H3'), 2.60 (s, 3H, SCH$_3$), 3.30 (m, 2H, H5'), 4.08 (s, 3H, OCH$_3$), 4.29 (m, 1H, H4'), 6.36 (d, J=3.7, 1H, H7), 6.53 (dd, J=7 and 4, 1H, H1'), 7.09 (d, J=3.7, 1H, H8), 7.25 and 7.45 (m, 15H, trityl H).

E. PREPARATION OF 7-IODO-6METHOXY-2-METHYLTHIO-9(5-O-TRIPHENYLMETHYL-2,3-DIDEOXY-β-D-RIBOFURANOSYL)7-DEAZAPURINE (13)

N-Iodosuccinimide (10.0 g) was added to a solution of deazapurine 12 (9.9 g) in dry dimethylformamide (550 mL). After stirring in the dark under nitrogen for 16 h, 10% aqueous sodium bicarbonate (2.5 mL) was added and the reaction mixture was concentrated in vacuo at 50° to a volume of 100 mL. This solution was partitioned between water and ethyl acetate. The organic layer was washed with 5% aqueous sodium hydrosulfite and brine, dried over sodium sulfate, and concentrated. Chomatography of the slightly impure product on silica gel with dichloromethane afforded 11.68 g (95.6%) of iodide 13 as a colorless glassy solid.

$^1$H—NMR (CDCl$_3$): 2.06, 2.24, and 2.41 (m, 4H, H2'and H3'), 2 58 (s, 3H, SCH$_3$), 3.30 (m, 2H, H5'), 4.10 (s, 3H, OCH$_3$), 4.29 (m, 1H, H4'), 6.47 (dd, J=6 and 4, 1H, H1'), 7.19 (s, 1H, H8), 7.30 and 7.46 (m, 15H, trityl H). This data was obtained from a different batch of 13 prepared as described above.

F. PREPARATION OF 7-IODO-2-METHYLTHIO-9-(5-O-TRIPHENYLMETHYL-2,3-DIDEOXY-β-D-RIBOFURANOSYL)7-DEAZAPURIN-4-ONE (14)

Sodium thiocresolate was prepared by adding sodium methoxide (1 eq) to a solution of thiocresol in methanol and then evaporating to dryness. A mixture of methyl ether 13 (4.0 g), sodium thiocresolate (4.0 g), and hexamethylphosphoramide (10 mL) in dry toluene (150 mL) was refluxed under nitrogen for 4.5 h. After cooling, the mixture was partitioned between ethyl acetate and water. The organic layer was washed with water and brine, dried over sodium sulfate, and evaporated to dryness. Chomatography of the resulting crude product on silica gel with 0% and 2% methanol in dichloromethane afforded 3.80 g (97.0%) of deazapurinone 14 as a colorless glassy solid.

$^1$H—NMR (CDCl$_3$): 2.05, 2.25, and 2.42 (m, 4H, H2' and H3'), 2.60 (s, 3H, SCH$_3$), 3.30 (m, 2H, H5'), 4.28 (m, 1H, H4'), 6.40 (dd, J=7 and 4, 1H, H1'), 7.05 (s, 1H, H8), 7.30 and 7.46 (m, 15H, trityl H), 10.00 (broad s, 1H, H1).

G. PREPARATION OF 7-IODO-5'-O-TRIPHENYLMETHYL2',3'-DIDEOXY-7-DEAZAGUANOSINE (15)

Meta-chloroperoxybenzoic acid (1.23 g, 85%, Aldrich) was added to a stirred solution of methylthio ether 14 (3.6 g) in dry dichloromethane (150 mL) at 0° under nitrogen. After 15 minutes, the cooling bath was removed and stirring was continued at 25° for 40 min. This solution was washed with aqueous sodium bicarbonate and brine and dried over sodium sulfate. Methanol (two percent by volume) was added and the resulting solution was passed though a short plug of silica gel to remove polar impurities. The resulting crude sulfoxide (3.07 g) was dissolved in dioxane (40 mL) and placed in a glass-lined bomb. Ammonia (10.0 g) was added and the mixture was heated at 100° for 2 h in an autoclave. The resulting solution was evaporated to dryness. The residue was dissolved in dichloromethane (20 mL) and filtered though a pad of filter-aid. Methanol (40 mL) was added to the solution and, on cooling, 1.57 g of colorless product crystallized. The mother liquor was evaporated and purified by medium pressure liquid chomatography on silica gel with 5% methanol in dichloromethane to afford an additional 328 mg of product as colorless crystals. The total yield of deazaguanosine 15 was 1.90 g (55.4%).

$^1$H—NMR (CDCl$_3$): 2.05, 2.23, and 2.35 (m, 4H, H2' and H3'), 3.29 (m, 2H, H5'), 4.26 (m, 1H, H4'), 5.90 (broad s, 2H, NH$_2$), 6.24 (dd, J=7 and 4, 1H, H1'), 6.90 (s, 1H, H8), 7.30 and 7.46 (m, 15H, trityl H) 10.90 (broad s, 1H, H1). Recrystallization of a sample of this material from methanol-dichloromethane afforded crystals of mp 201°–203°.

H. PREPARATION OF 2',3'-DIDEOXY-7-IODO-7-DEAZAGUANOSINE (16)

A solution of trityl ether 15 (1.7 g) in formic acid (12 mL) was stirred at room temperature for 10 min. The resulting yellow suspension was then quickly evaporated to dryness in vacuo at 30°. Chomatography of the residue on silica gel with 5%, 7%, and 10% methanol in dichloromethane afforded 940 mg of a colorless solid. Trituration of this solid with ether containing a little dichloromethane yielded 838 mg (81.0%) of nucleoside 16 as colorless crystals.

$^1$H—NMR (DMSO-d$_6$): 1.95, 2.09, and 2.26 (m, 4H, H2' and H3'), 3.48 and 3.54 (m, 2H, H5'), 3.98 (m, 1H, H4'), 4.90 (broad t, J=5, 1H, 5'OH), 6.08 (m, 1H, H1'), 6.32 (broad s, 2H, NH$_2$), 7.12 (s, 1H, H8), 10.46 (broad s, 1H, H1).

I. PREPARATION OF 7-(3-TRIFLUOROACETAMIDEO-1-PROPYNYL)2',3'-DIDEOXY-7-DEAZAGUANOSINE (50)

Iodide 16 (376 mg, 1.00 mmol) was coupled for 2.25 h to N-propargyltrifluoroacetamide by the general method given in Example 1C. Product and starting material were indistinguishable by TLC, so the reaction was monitored by reverse phase HPLC (10 cm ODS, 1 mL/min, gradient from 100% water to 100% methanol over 5 min, then 100% methanol, with UV detection at 280 nm: starting iodide 16, 5.49 min; product 50, 5.75 min; intermediate, 6.58 min). The crude product was poorly soluble in dichloromethane, so it was concentrated from a dichloromethane-methanol solution onto silica gel (5 g) before being loaded onto the chomatography column. Elution with 2%, 5%, 7% and 10% methanol in dichloromethane afforded 300 mg (78%) of alkynylamino nucleoside 50 as a yellow solid.

$^1$H—NMR (DMSO-d$_6$): 1.96, 2.08, and 2.28 (m, 4H, H2' and H3'), 3.47 and 3.55 (m, 2H, H5'), 3.99 (m, 1H, H4'), 4.22 (broad s, 2H, —CH$_2$—), 4.90 (t, J=5, 1H, 5'OH), 6.09 (dd, J=6 and 4, 1H, H1'), 6.33 (broad s, 2H, NH$_2$), 7.30 (s, 1H, H8), 10.05 (broad s, 1H, NHTFA), 10.50 (broad s, 1H, H1). $^1$H-Decoupled $^{13}$C—NMR (DMSO-d$_6$): 155.5 (q, J=36.5, trifluoroacetyl carbonyl), 157.8, 153.1 and 149.9 (C2, C4 and C6), 122.6 (C8), 115.9 (q, J=288, CF3), 99.4 and 97.5 (C7 and C5), 84.2 and 77.4 (acetylenic), 83.2 and 81.0 (C1' and C4'), 62.9 (C5'), 29.7 (propargylic), 31.8 and 25.8 (C2' and C3'). This $^{13}$C—NMR data was obtained from a different batch of 50 prepared as described above.

J. PREPARATION OF 7-(3-AMINO-1-PROPYNYL)-2',3'DIDEOXY-7-DEAZAGUANOSINE 5'-TRIPHOSPHATE (49)

Alkynylamino nucleoside 50 (0.90 mmol) was converted to the corresponding 5'-triphosphate and the trifluoroacetyl protecting group was subsequently removed following the general procedure given in Example 1E. After the second addition of phosphorus oxychloride, the reaction was stirred for an additional 165 min. Assuming an absorption coefficient for the product equal to that of the starting material (11,900), the yield of 5'-triphosphate 49, based on its absorption at 272.5 mn, was 18%.

EXAMPLE 4

PREPARATION OF 7-(3-AMINO-1-PROPYNYL)-2',3'-DIDEOXY7-DEAZAADENOSINE 5'-TRIPHOSPHATE (51)

(Compound 51 is an example of structure 6 wherein Het is 7-deazaadenine (j) and R$_1$ is —CH$_2$—. It is the immediate precursor to labeled chain terminator 36.)

A. PREPARATION OF 2'-ACETOXY-3'-BROMO-5'-(2-ACETOXYISOBUTYRYL)ADENOSINE (18)

2-Acetoxyisobutyryl bromide (19.5 mL, 150 mmol, 5 eq, prepared according to the procedure of Russell et al, J. Am. Chem Soc., 95, 4016-4030 (1973)) was added over 15 min to a suspension of tubercidin (17, 7-deazaadenosine, 6.66 g, 25.0 mmol, Sigma) in dry acetonitrile (250 mL, Aldrich). The suspended solid dissolved in about 5 min and the reaction was stirred under nitrogen for 22 h at 25°. The reaction mixture was added to a solution of dipotassium hydrogen phosphate (43.55 g, 300 mmol, 6 eq) in water (400 mL). After stirring for 30 min, the solution was extracted with ethyl acetate (1×400 mL and 2×200 mL). The combined organic layers were dried over magnesium sulfate and evaporated to dryness to afford 14.73 g, (118%) of white foam. This material was greater than 95% one slightly broadened spot by TLC (with UV detection), but NMR showed that one major and at least one minor product were present. The NMR spectrum was consistent with the major product being bromoacetate 18.

$^1$H—NMR (DMSO-d$_6$) for the major component 18: 8.08 (s, 1H, H2), 7.34 (d, J=3.7, 1H, H8), 7.12 (broad s, 2H, NH$_2$), 6.70 (d, J=3.7, 1H, H7), 6.32 (d, J=3.8, 1H, H1'), 5.61 (dd, J=2.4 and 3.8, 1H, H2'), 4.89 (dd, J=2.4 and 4.5, 1H, H3'), 4.43 (m, 1H, H4'), 4.35 (dd, J=12 and 4, 1H, H5'a), 4.29 (dd, J=12 and 7, 1H, H5'b), 2.08 (s, 3H, OAc), 2.00 (s, 3H, OAc), and 1.49 (s, 6H, 2CH$_3$).

B. PREPARATION OF 2',3'-DIDEOXY-2',3'-DIDEHYDRO7-DEAZAADENOSINE (19)

Zinc-copper couple was freshly prepared by rapidly (total elapsed time of about 10 min) washing zinc dust (20 g, Mallinkrodt) with 1N hydrochloric acid (3×50 mL), water (2×50 mL), 2% cupric sulfate (2×50 mL), water (4×50 mL), ethanol (3×50 mL) and ether (2×50 mL). During each wash, the zinc dust was stirred in a fritted funnel until it was suspended and the wash was removed by suction while minimizing exposure of the zinc to air. The couple was vacuum dried for 30 min. The above crude bromoacetate (14.63 g) was dissolved in dry dimethylformamide (150 mL, Aldrich) and approximately 25 mL of solvent was removed with a rotary evaporator (45°, at 2 torr). Fresh zinc-copper couple (14.63 g, about 9 eq) was added and the resulting suspension was stirred under nitrogen at 25°. Depending on the quality of the zinc-copper couple, this reaction can show an induction period and/or variable rate, so the reaction was allowed to proceed until TLC (90:9:1 dichloromethane-methanol-concentrated ammonium hydroxide: starting material $R_f=0.45$ and products $R_f=0.39$ and 0.36) indicated the starting material had been completely consumed. In this case, the reaction was complete in less than 15 min. After 100 min, saturated aqueous sodium bicarbonate (75 mL) was added carefully over 10 min to the reaction mixture. The reaction mixture was filtered though a filter aid and the filter aid was washed with methanol (2×50 mL). The combined filtrates were evaporated to dryness and the residue was partitioned between water (150 mL) and ethyl acetate (150 mL). The aqueous layer was extracted with ethyl acetate (2×100 mL) and the combined organic extracts were dried over magnesium sulfate, concentrated, and vacuum dried for 1 h.

The resulting dark orange semisolid was dissolved in methanol (100 mL) and then water (25 mL) and REXYN 201 resin (29 g, 4.3 meq/g, 5 eq, hydroxide form) were added. The reaction mixture was refluxed for a total of 210 min. Monitoring by TLC (85:13:2 dichloromethane-methanol-concentrated ammonium hydroxide: intermediate, Rf=0.49; final product 19, 0.24) indicated that the reaction had rapidly halted at about 70% conversion, so after 165 min, additional resin (29 g) was added. Without cooling, the resin was removed by filtration and washed with 1:1 dichloromethane-methanol (2×75 mL). The combined filtrates were evaporated to dryness and the resulting purple solid was recrystallized from boiling isopropanol (150 mL) to afford 3.778 g, of olefin 19 as a off-white needles (mp 205°-206°). A second crop of 0.631 g, of product (pale purple needles, mp 202°-203°) was obtained by concentrating the mother liquors to 25 mL. Both crops (total 4.409 g, 76%) were homogeneous by TLC and pure by NMR except for a trace of isopropanol.

$^1$H—NMR (DMSO-$d_6$): 8.07 (s, 1H, H2), 7.15 (d, J=3.6, 1H, H8), 7.12 (broad s. 1H, H1,), 7.01 (broad s, 2H, NH$_2$), 6.57 (d, J=3.6, 1H, H7), 6.43 and 6.02 (broad d, J=6.0, 1H each, H2'and H3'), 4.95 (t, J=6.5, 1H, 5'OH), 4.79 (m, 1H, H4'), and 3.52 (m, 2H, H5').

C. PREPARATION OF 2',3'-DIDEOXY-7-DEAZAADENOSINE (20)

A 450-mL Parr bottle was charged with olefin 19 (3.80 g), ethanol (76 mL), 10% palladium on carbon (380 mg, Aldrich) and 40 psi of hydrogen. After shaking for 4.67 h at 25°, 14.5 psi of hydrogen had been absorbed and hydrogen uptake had ceased. TLC (two elutions with 85:13:2 dichloromethane-methanol-concentrated ammonium hydroxide: starting material 19, 0.45; product 20, 0.48) showed complete conversion to a single UV-active new product. The catalyst was removed by filtration though filter aid and washed with ethanol. Removal of solvent from the filtrate and vacuum drying overnight afforded 3.98 g, (104%) of dideoxynucleoside 20 as a white foam. NMR indicated that the product was homogeneous except for the presence of 8 wt % of ethanol (96% corrected yield). Similar batches of this material resisted crystallization and became extremely hygroscopic upon azeotropic drying with anhydrous solvents. Therefore this material was stored under vacuum for about 1 week and used when NMR indicated that the material contained 5 wt % of ethanol. The lack of crystallinity and spectral characteristics observed for this product were in accord with those reported previously by Robins et al., Can. J. Chem., Vol. 55, 1259 (1977).

$^1$H—NMR (DMSO-$d_6$): 8.04 (s, 1H, H2), 7.33 (d, J=3.6, 1H, H8), 6.97 (broad s, 2H, NH$_2$), 6.56 (d, J=3.6, 1H, H7), 6.34 (dd, J=5.2 and 6.4, 1H, H1'), 4.96 (t, J=5.6, 1H, 5'OH), 4.33 (t, J=5.1, 0.43H, ethanol OH), 4.04 (m, 1H, H4,), 3.4-3.6 (m, 2.86H, H5' and ethanol CH$_2$), 2.33, 2.21 and 2.02 (m, 4H, H2' and H3'), and 1.06 (t, J=7.0, 1.3H, ethanol CH$_3$).

D. PREPARATION OF 7-IODO-2',3'-DIDEOXY-7-DEAZAADENOSINE (21)

A mechanically-stirred solution of 95% pure dideoxynucleoside 20 (2.95 g, 11.96 mmol), anydrous sodium acetate (4.13 g, 50.3 mmol, 4 eq), and mercuric acetate (3.81 g, 11.95 mmol, 1.00 eq, Fisher, 99.9%) in water (190 mL) was heated under nitrogen at 65° for 2 h. After cooling the resulting white suspension of mercurial to 25°, iodine (4.79 g, 18.9 mmol, 1.6 eq) and ethyl acetate (190 mL) were added. After 1 h, the suspended mercurial had been consumed and a clear purple solution remained. After 2 h, sodium sulfite (6.35 g) was added and the purple color disappeared. After stirring for 30 min, hydrogen sulfide gas was gently bubbled into the reaction for 15 min. Mercuric sulfide (a black colloid) and iodide 21 (a white powder) precipitated from the reaction. Complete precipitation of mercury(II) was assessed by TLC by monitoring the disappearance of one of the two major UV-active spots. The reaction mixture was filtered though filter aid and separated into two layers. The filter aid was washed with boiling ethyl acetate (9×100 mL) until TLC indicated that no further product was being extracted. Each ethyl acetate extract was washed with the aqueous layer. The combined ethyl acetate layers were dried over magnesium sulfate and evaporated to dryness. The resulting crude solid turned red upon exposure to air. This material was dissolved in 3:1 dichloromethanemethanol (100 mL) and the free base form of AG3 X4A anion exchange resin (5.0 g, BioRad, 2.9 meq/g dry) was added. Hydrogen sulfide was bubbled into the red solution for 10 min and the red color was discharged. A slight cloudiness was eliminated by briefly warming and the solution was rapidly filtered though a 2 cm plug (15 g) of silica gel. The silica gel was eluted with additional 3:1 dichloromethane-methanol (100 mL). Silica gel (50 g) was added to the filtrate and hydrogen sulfide was bubbled in for 10 min. The solvent was removed from this mixture with a rotary evaporator and the silica gel was "dried" by co-evaporating with chloroform (200 mL). This silica gel was rapidly loaded onto a silica gel, column (500 g) which had been degassed with a stream of nitrogen. Elution under nitrogen with 5% (6 L) and 10% (4 L) boiling methanol in dichloromethane afforded 2.92 g, (64%) of iodide 21 as a white powder and 456 mg (7.5%) of less polar 7,8-diiodo2',3'-dideoxy-7-deazaadenosine. Recrystallization of the major product from boiling ethyl acetate (200 mL) afforded 2.626 g, of white needles (mp 158°-160°). Concentration of the mother liquors to 10 mL afforded a second crop of 0.391 g, of light red needles (mp 156°-). Both crops were homogeneous according to NMR and TLC and together represent a 64% overall yield of iodonucleoside 21 from olefin 19. $^1$H—NMR (DMSO-d$_6$): 8.09 (s, 1H, H2), 7.67 (s, 1H, H8), 6.65 (broad s, 2H, NH$_2$), 6.34 (dd, J=4.4 and 6.8, 1H, H1′), 4.95 (t, J=5.5, 1H, 5′OH), 4.04 (apparent hept, J=3.5, 1H, H4′), 3.59 and 3.49 (m, 2H, H5′), 2.30, 2.28 and 2.00 (m, 4H, H2′ and H3′).

E. PREPARATION OF 7-(3-TRIFLUOROACETAMIDO-1-PROPYNYL)2′,3′-DIDEOXY-7-DEAZAADENOSINE (52)

Iodide 21 (720.3 mg, 2.00 mmol) was coupled for 90 min with N-propargyltrifluoroacetamide following the standard procedure given in Example 1C. Chomatography with 7% methanol in dichloromethane afforded 705.8 mg (92%) of coupling product 52 as an off white powder which was homogeneous according to NMR and TLC. Recrystallization from boiling ethyl acetate (10 mL) afforded 372 mg of white microcrystals (mp 169°–171°).

$^1$H—NMR (DMSO-d$_6$): 10.1 (distorted t, 1H, NHTFA), 8.10 (s, 1H, H2), 7.78 (s, 1H, H8), 6.0–7.5 (very broad s, 2H, NH$_2$), 6.34 (dd, J=4.5 and 7.0, 1H, H1′), 4.98 (t, J=5, 1H, 5′OH), 4.31 (slightly broadened s, H2—CH$_2$N—), 4.10 (apparent hept, J=3.5, 1H, H4′), 3.60 and 3.40 (m, 2H, H5′), 2.37, 2.18 and 2.00 (m, 4H, H2′ and H3′). TLC (90:9:1 dichloromethane-methanol-concentrated ammonium hydroxide; UV): starting iodide 21, R$_f$=0.36; product 52, 0.26).

F. PREPARATION OF 7-(3-AMINO-1-PROPYNYL)-2′,3′-DIDEOXY7-DEAZAADENOSINE 5′-TRIPHOSPHATE (51)

Alkynylamino nucleoside 52 (1.00 mmol) was converted to the corresponding 5′-triphosphate and the trifluoroacetyl group was removed following the general procedure described in Example 1E. After addition of the second aliquot of phosphorus oxychloride, the solution was stirred for 120 min. Assuming an absorption coefficient for the product equal to that of the starting material (12,700), the yield of triphosphate 51, based on the absorption at 279.5 nm, was 40%.

$^1$H—NMR (D$_2$O): 7.97 (s, 1H, H2), 7.80 (s, 1H, H8), 6.33 (m, 1H, H1′), 4.44 (m, 1H, H4′), 4.27 (m, 1H, H5′a), 4.14 (m, 1H, H5′b), 4.11 (broad s, 2H, —CH$_2$—), 2.6–2.0 (m, 4H, H2′ and H3′), plus counterion (triethylammonium) peaks. $^{31}$P-NMR (D$_2$O): −8.59 (broad d, J=20, 1P), −9.56 (d, J=20, 1P), and −21.38 (m, 1P). UV (pH 8.2 aq Tris): maxima at 238 and 279.5 nm.

EXAMPLE 5

A SECOND PREPARATION OF 7-IODO-2′,3′-DIDEOXY-7-DEAZAADENOSINE (21)

(Compound 21 is an intermediate prepared and used in Example 4.)

A. PREPARATION OF 6-CHLORO-2-METHYLTHIO-9-(2-DEOXY-β-D-RIBOFURANOSYL)-7-DEAZAPURINE (23)

Methanol (210 mL) and concentrated ammonium hydroxide (210 mL) were added to a solution of 6-chloro-2-methylthio-9-(3,5-di-O-p-toluoyl-2-deoxy-β-D-ribofuranosyl)-7-deazapurine (22, 26.8 g, prepared as described by Kazamierczuk et al., J. Am. Chem. Soc., Vol. 106, 6379 (1984)) in dichloromethane (210 mL). The resulting mixture was stirred at room temperature for 5 d and then evaporated to dryness. The residue was dried by co-evaporation with ethanol. The crude product was dissolved in dichloromethane and colorless crystals precipitated upon standing. The precipitate was collected and washed thoroughly with ether to afford 14.5 g, (79.1%) of diol 23 (mp d 190°–192°).

$^1$H—NMR (DMSO-d$_6$): 2.26 and 2.55 (m, 2H, H2′), 2.57 (s, 3H, SCH$_3$), 3.54 (m, 2H, H5′), 3.84 (m, 1H, H3′), 4.37 (m, 1H, H4′), 4.95 (m, 1H, OH), 5.34 (m, 1H, OH), 6.57 (m, 1H, H1′), 6.63 (m, 1H, H7), 7.80 (m, 1H, H8). This data was obtained from a different batch of diol 23 prepared as described above.

B. PREPARATION OF 6-CHLORO-2-METHYLTHIO-9-(5-O-TRIPHENYLMETHYL-2-DEOXY-β-D-RIBOFURANOSYL)7-DEAZAPURINE (24)

Diol 23 (14.5 g) was dried by co-evaporation with dry pyridine. Triphenylmethyl chloride (16 g), 4-(dimethylamino)pyridine (600 mg), and triethylamine (8.0 mL) were added to a solution of the dry diol in dry pyridine (200 mL). After stirring the reaction mixture at 65° under nitrogen for 6 h, additional triphenylmethyl chloride (2.0 g) and triethylamine (1.0 mL) were added and heating was continued for 17 h. After cooling, methanol (3 mL) was added and the reaction mixture was evaporated to dryness. The residue was partitioned between dichloromethane and 0.3N hydrochloric acid. The organic layer was washed with aqueous sodium bicarbonate and brine, dried over sodium sulfate, and evaporated to dryness. Chomatography of the resulting crude product on silica gel with 1% and 1.5% methanol in dichloromethane afforded 22.7 g, (88.6%) of monotrityl ether 24 as a glassy solid. $^1$H—NMR (CDCl$_3$): 2.48 and 2.60 (m, 2H, H2′), 2.59 (s, 3H, SCH$_3$), 3.40 (m, 2H, H5′), 4.08 (m, 1H, H3′), 4.61 (m, 1H, H4′), 6.43 (m, 1H, H7), 6.68 (m, 1H, H1′), 7.2–7.5 (m, 16H, trityl H and H8). This data was obtained from a different batch of 24 prepared as described above.

C. PREPARATION OF 6-CHLORO-2-METHYLTHIO-9-(5-O-TRIPHENYLMETHYL-2,3-DIDEOXY-β-D-RIBOFURANOSYL)-7-DEAZAPURINE (25)

4-(Dimethylamino)pyridine (16.5 g) and phenyl chlorothionocarbonate (13.5 mL) were added to a solution of trityl ether 24 in dry dichloromethane (300 mL). After stirring the reaction mixture at room temperature under nitrogen for 2.25 h, dichloromethane (200 mL) was added. The solution was washed with 0.5N hydrochloric acid (700 mL), 0.5N sodium hydroxide (700 mL), and brine. The organic layer was dried over sodium sulfate and evaporated to dryness.

The resulting crude thiocarbonate was dissolved in dry toluene (450 mL) and the solution was heated to a gentle reflux. Azoisobisbutyronitrile (600 mg) and tri-n-butyltin hydride (17.7 mL) were added. After stirring at reflux under nitrogen for 15 min, additional tri-n-butyltin hydride (2.0 mL) was added and the reaction mixture was refluxed for another 15 min. After cooling, the reaction mixture was diluted with ether (200 mL) and washed with 10% aqueous potassium fluoride (500 mL), 0.75N potassium hydroxide (500 mL), and brine. After drying over sodium sulfate and concentrating, chomatography of the resulting crude product on silica gel with 2:1 dichloromethane-ether and dichloromethane afforded 10.1 g, of dideoxynucleoside 25. The impure fractions were combined and rechomatographed to afford an additional 3.76 g, of pure product These products were combined to afford 13.9 g, (63.0%) of 25 as a colorless solid (mp 140°-142.5°).

$^1$H—NMR (CDCl$_3$): 2.11, 2.36, and 2.46 (m, 4H, H2' and H3'), 2.60 (s, 3H, SCH$_3$), 3.33 (apparent d, J=4, 2H, H5'), 4.32 (m, 1H, H4'), 6.39 (d, J=3.7, 1H, H7), 6.52 (dd, J=6.7 and 3.7, 1H, H1,), 7.25 and 7.45 (m, 15H, trityl H), 7.32 (d, 1H, J=3.7, H8). This data was obtained from a different batch of 25 prepared as described above.

D. PREPARATION OF 6-CHLORO-2-METHYLTHIO-9-(2',3'-DIDEOXY-β-D-RIBOFURANOSYL)-7-DEAZAPURINE (26)

Trifluoroacetic acid (10 mL) was added to a solution of trityl ether 25 (7.58 g) in 1:1 methanol-dichloromethane (100 mL) and the solution was stirred at 25° under nitrogen for 17 h. The reaction mixture was partitioned between dichloromethane (500 mL) and aqueous sodium bicarbonate, and the aqueous layer was re-extracted with dichloromethane. The combined organic layers were dried over sodium sulfate and evaporated to dryness. Chomatography of the residue on silica gel with 0% and 5% methanol in dichloromethane afforded 4.07 g (97.1%) of nucleoside 26 as a thick colorless glass.

$^1$H—NMR (CDCl$_3$): 2.16, 2.26, and 2.50 (m, 4H, H2' and H3'), 2.63 (s, 3H, SCH$_3$), 2.76 (broad s, 1H, OH), 3.67 and 3.93 (m, 2H, H5'), 4.27 (m, 1H, H4'), 6.38 (dd, J=6.7 and 5.2 Hz, 1H, H1'), 6.51 (d, J=3.7 Hz, 1H, H7), 7.26 (d, 1H, J=3.7 Hz, H8). This data was obtained from a different batch of 26 prepared as described above.

E. PREPARATION OF 2',3'-DIDEOXY-2-METHYLTHIO7-DEAZAADENOSINE (27)

Ammonia (10 g) was distilled into a solution of chloride 26 (1.83 g) in methanol (50 mL) in a glass-lined bomb. The solution was heated in an autoclave at 100° for 15 h. After cooling, the reaction mixture was evaporated to dryness. Purification of the resulting crude product on silica gel with 0%, 3% and 5% methanol in dichloromethane afforded 1.27 g, (80.4%) of deazaadenosine 27 as a colorless solid (mp 184°-185°).

$^1$H—NMR (DMSO-d$_6$): 2.01, 2.21, and 2.39 (m, 4H, H2'and H3'), 2.45 (s, 3H, SCH$_3$), 3.50 (m, 2H, H5'), 4.02 (m, 1H, H4'), 4.83 (t, J=5.5, 1H, 5'OH), 6.32 (dd, J=7 and 4.5, 1H, H1'), 6.50 (d, J=3.7, 1H, H7), 7.07 (broad s, 2H, NH$_2$), 7.20 (d, 1H, J=3.7, H8).

F. PREPARATION OF 2',3'-DIDEOXY-7-DEAZAADENOSINE (20)

A mixture of 600 mg of 27 and excess Raney Nickel (Aldrich, pre-washed with water and methanol) was refluxed under nitrogen until TLC indicated the disappearence of the starting material (6 h). The hot solution was filtered though filter-aid and the collected Raney nickel was washed well with methanol. The combined filtrates were evaporated to afford 424 g (84.9%) of 20 as a colorless glassy solid identical to the material prepared in Example 4C.

G. PREPARATION OF 7-IODO-2',3'-DIDEOXY-7-DEAZAADENOSINE (21)

Dideoxy-7-deazaadenosine 20 was iodinated following the procedure given in Example 4D.

EXAMPLE 6

A THIRD PREPARATION OF 7-IODO-2',3'-DIDEOXY-7-DEAZAADENOSINE (21)

(Compound 21 is an intermediate prepared and used in Example 4.)

A. PREPARATION OF 6-CHLORO-9-(2-DEOXY-β-D-RIBOFURANOSYL)-7-DEAZAPURINE (29)

A solution of concentrated ammonium hydroxide (100 mL) in methanol (175 mL) was added to a solution of 6-chloro-9-(3,5-di-O-p-toluoyl-2-deoxy-β-D-ribofuranosyl)-7-deazapurine (28, 10.0 g; prepared as described by Z. Kazimierczuk et al., J. Amer. Chem. Soc., Vol. 106, 6379 (1984)) in dichloromethane (100 mL). After stirring the resulting mixture at 25° for 24 h, additional concentrated ammonium hydroxide (50 mL) was added. After stirring for a total of 5 d, the reaction mixture was evaporated to dryness and the crude product co-evaporated with ethanol. The residue was dissolved in dichloromethane and the desired product crystallized. Filtration and drying afforded 4.90 g (92%) of nucleoside 29 as colorless crystals (mp 155.5°-158.5°).

$^1$H—NMR (DMSO-d$_6$): 2.30 and 2.55 (m, 2H, H2'), 3.58 (m, 2H, H5'), 3.85 (m, 1H, H3'), 4.40 (m, 1H, H4'), 4.97 (m, 1H, OH), 5.35 (m, 1H, OH), 6.65 (m, 1H, H1,), 6.75 (d, 1H. H7), 8.00 (m, 1H, H8), 8.65 (s, 1H, H2). This data was obtained from a different batch of 29 prepared as described above.

B. PREPARATION OF 6-CHLORO-9-(5-O-TRIPHENYLMETHYL-2-DEOXY-β-D-RIBOFURANOSYL)-7-DEAZAPURINE (30)

Nucleoside 29 (2.5 g) was dried by co-evaporation with dry pyridine. The residue was redissolved in dry pyridine (40 mL) and triphenylmethyl chloride (2.5 g), 4-(dimethylamino)pyridine (120 mg), and triethylamine (1.6 mL) were added. The reaction mixture was stirred at 65° for 4 h under nitrogen. Additional triphenylmethyl chloride (1.0 g) and triethylamine (0.6 mL) were added and the reaction was stirred at 75° for 18 h. After cooling, methanol (2 mL) was added and the reaction mixture was evaporated to dryness. The residue was partitioned between dichloromethane and 0.5N hydrochloric acid. The organic layer was washed with aqueous sodium bicarbonate and brine, dried over sodium sulfate, and evaporated to dryness. Chromatography on silica gel with 0%, 1.5% and 3% methanol in dichloromethane afforded 2.26 g, (48%) of trityl ether 30 as a glassy solid.

$^1$H—NMR (CDCl$_3$): 2.46 and 2.65 (m, 2H, H2'), 3.40 (m, 2H, H5'), 4.10 (m, 1H, H3'), 4.65 (m, 1H, H4'), 6.55 (d, 1H. H7), 6.72 (m, 1H, H1'), 7.2-7.5 (m, 16H, trityl H and H8), and 8.60 (s, 1H, H2).

C. PREPARATION OF 6-CHLORO-9-(5-O-TRIPHENYLMETHYL2-DEOXY-3-THIONOCARBOPHENOXY-β-D-RIBOFURANOSYL)7-DEAZAPURINE (30a)

4-(Dimethylamino)pyridine (1.35 g) and phenyl chlorothionocarbonate (1.20 mL) were added to a solution of trityl ether 30 in dry dichloromethane (30 mL). After stirring the reaction mixture under nitrogen for 2 h at 25°, additional dichloromethane (20 mL) was added and the solution was washed with 0.5N hydrochloric acid, 0.5N sodium hydroxide, and brine. The organic layer was dried over sodium sulfate and evaporated to dryness. Trituration of the residue with dichloromethane-ether afforded 1.53 g, (76%) of thiocarbonate 30a as colorless crystals (mp 186.5°–188.5°).

$^1$H—NMR (CDCl$_3$): 2.85 and 3.00 (m, 2H, H2'), 3.55 m, 2H, H5'), 4.50 (m, 1H, H4'), 6.00 (m, 1H, H3'), 6.60 (d, 1H. H7), 6.85 (m, 1H, H1'), 7.1–7.5 (m, 20H, trityl and phenyl H), 7.50 (d, 1H, H8), and 8.60 (s, 1H, H2).

D. PREPARATION OF 6-CHLORO-9-(5-O-TRIPHENYLMETHYL2,3-DIDEOXY-β-D-RIBOFURANOSYL)-7-DEAZAPURINE (31)

A solution of thiocarbonate 30a (1.2 g), azoisobis-butyronitrile (50 mg), and tri-n-butyltinhydride (0.60 mL) in dry toluene (50 mL) was heated at 110° under nitrogen for 15 min. After cooling, the reaction mixture was diluted with 50 mL of ether and washed with 10% aqueous potassium fluoride (50 mL) and brine. The organic layer was dried over sodium sulfate and evaporated to dryness. Chromatography of the resulting crude product on silica gel with 0% and 1.5% methanol in dichloromethane afforded 0.84 g, (92%) of dideoxynucleoside 31 as a colorless solid (mp 60°–63.5°).

$^1$H—NMR (CDCl$_3$): 2.11, 2.36, and 2.50 (m, 4H, H2'and H3'), 3.37 (m, 2H, H5'), 4.35 (m, 1H, H4'), 6.50 (d, J=3.7, 1H, H7), 6.58 (dd, 1H, H1'), 7.25 and 7.45 (m, 15H, trityl H), 7.55 (d, 1H, J=3.7, H8), and 8.60 (s, 1H, H2).

E. PREPARATION OF 6-CHLORO-9-(2,3-DIDEOXY-β-D-RIBOFURANOSYL)-7-DEAZAPURINE (31a)

Trifluoroacetic acid (1.5 was added to a solution of trityl ether 31 (700 mg) in 1:1 methanoldichloromethane (20 mL). After stirring under nitrogen at 25° for 17 h, sodium bicarbonate (1.5 g) was added and the mixture was stirred for 30 min. The reaction mixture was filtered and evaporated to dryness. Chromatography of the resulting crude product on silica gel with 0% and 2% methanol in dichloromethane afforded 300 mg (84%) of alcohol 31a as a colorless glass. $^1$H—NMR (CDCl$_3$): 2.20, 2.40, and 2.65 (m, 4H, H2' and H3'), 3.65 and 4.00 (m, 2H, H5'), 3.95 (broad s, 1H, OH), 4.35 (m, 1H, H4'), 6.28 (dd, 1H, H1'), 6.62 (d, J=4, 1H, H7), 7.40 (d, 1H, J=4, H8), and 8.65 (s, 1H, H2).

F. PREPARATION OF 6-CHLORO-9-(5-ACETOXY-2,3-DIDEOXY-β-D-RIBOFURANOSYL)-7-DEAZAPURINE (32)

Acetic anhydride (2.0 mmol) was added to a solution of alcohol 31a (284 mg) in dry pyridine (10 mL). After stirring the solution for 1.25 h at 25°, methanol (10 mL) was added. After stirring an additional 30 min, the reaction mixture was evaporated to dryness. The residue was dissolved in dichloromethane and this solution was washed with 1N hydrochloric acid (2×) and brine (1×). The organic layer was dried over sodium sulfate and evaporated to dryness to afford 295 mg (89%) of crude acetate 32 as a colorless glass.

$^1$H—NMR (CDCl$_3$): 2.07 (s, 3H, acetyl), 2.20, 2.45, and 2.55 (m, 4H, H2'and H3'), 4.25 and 4.35 (m, 2H, H5'), 4.40 (m, 1H, H4'), 6.55 (dd, 1H, H1'), 6.65 (d, 1H, H7), 7.50 (d, 1H, H8), and 8.60 (s, 1H, H2).

G. PREPARATION OF 6-CHLORO-7-IODO-9-(5-O-ACETYL-2,3-DIDEOXY-β-D-RIBOFURANOSYL)-7-DEAZAPURINE (33)

A solution of iodine monochloride (340 mg; in dichloromethane (about 1 mL) was added to a solution of acetate 32 (200 mg) in dry dichloromethane (20 mL). After stirring at 25° for 3 h, the reaction mixture was partitioned between dichloromethane and aqueous sodium hydrosulfite. The organic layer was washed with aqueous sodium bicarbonate and brine, dried over sodium sulfate and evaporated to dryness. The residue was triturated with dichloromethane-ether to afford 135 mg (47%) of colorless crystals (mp 132.5°–134°).

$^1$H—NMR (CDCl$_3$): 2.10, 2.40, and 2.55 (m, 4H, H2' and H3'), 2.17 (s, 3H, COCH$_3$), 4.27 and 4.37 (m, 2H, H5'), 4.40 (m, 1H, H4'), 6.55 (dd, 1H, H1'), 7.72 (s, 1H, H8), and 8.60 (s, 1H, H2).

H. PREPARATION OF 7-IODO-2',3'-DIDEOXY-7-DEAZAADENOSINE (21)

Ammonia (4 g) was added to a solution of 125 mg of chloride 33 in methanol (20 mL) in a glass-lined bomb. The bomb was heated in an autoclave at 100° for 3 h. After cooling, the reaction mixture was evaporated to dryness. The residue was dissolved in hot ethyl acetate and the hot solution was filtered though a pad of filter aid. After evaporating the filtrate to dryness, the residue was triturated with ether to afford 85 mg of slightly impure product 21 as colorless crystals. Further purification of this material by preparative TLC on a silica gel with 5% methanol in dichloromethane afforded 67 mg (63%) iodide 21 as a colorless solid. This material was identical to that prepared in Example 4D.

EXAMPLE 7

PREPARATION OF 7-IODO-2',3'-DIDEOXY-7-DEAZAINOSINE (53)

(Compound 53 is an example of structure 4 wherein Het is 7-deazahypoxanthine (1))

Water (18 mL) was added dropwise to a suspension of deazaadenosine 21 (720.3 mg, 2.00 mmol) in glacial acetic acid (2.0 mL) under argon to produce a clear solution. Solid sodium nitrite (1.38 g, 20.0 mmol, 10 eq) was added though a stream of argon in small batches over 10 min. The resulting cloudy reaction mixture was mechanically stirred under argon and a gummy precipitate gradually formed. After 18 h, the reaction was filtered and the precipitate was washed thoroughly with ethyl acetate (100 mL) and water (about 10 mL). The combined filtrates were partitioned and the aqueous layer was extracted with ethyl acetate (2×50 mL). The combined organic layers were dried over magnesium sulfate and evaporated to dryness. According to TLC, both the precipitate and the ethyl acetate extracts consisted of product 53 and contaminated with less than 5% of unreacted 21. Both batches of product were dissolved in 1:1 methanol-dichloromethane, combined, and evaporated onto silica gel (7 g). The silica gel was co-evaporated with chloroform (50 mL) and placed on a silica gel column (50 g). Elution with 8% methanol in dichloromethane afforded 558.3 mg (78%) of deazainosine 53 as a pale yellow solid. Two crops of white needles were obtained by recrystallizing this material from boiling isopropanol. These needles exhibited a melting point with decomposition that varied between 200° and 210°. The chromatographed and recrystallized products were homogeneous by TLC and NMR except for the presence of isopropanol (5 mole %).

$^1$H—NMR (DMSO-d$_6$): 12.04 (broad s, 1H, H1), 7.93 (s, 1H, H2), 7.56 (s, 1H, H8), 6.29 (dd, J=4.0 and 6.8, 1H, H1'), 4.94 (t, J=5.0, 1H, 5'OH), 4.04 (apparent hept, J=3.5, 1H, H4'), 2.36, 2.18 and 1.99 (m, 4H, H2' and H3').

EXAMPLE 8

PREPARATION OF 5-(3-AMINO-1-PROPYNYL)2-DEOXYCYTIDINE 5'-TRIPHOSPHATE (54)

(Compound 54 is an example of an alkynylamino nucleotide (I) wherein R$_1$ is —CH$_2$—, Het is cytosine (i), R$_2$, R$_3$, R$_7$, and R$_8$ are H, R$_6$ is OH, and R$_5$ is P$_3$O$_9$H$^{3-}$—.)

A. PREPARATION OF 5-IODO-2'-DEOXYCYTIDINE (55)

A solution of 2,-deoxycytidine monohydrate (1.226 g, 5.00 mmol, Aldrich) and mercuric acetate (1.753 g, 5.5 mmol, 1.1 eq, Fisher) in methanol (20 mL) was refluxed for 14.5 h. The resulting white suspension was diluted with methanol (30 mL) and dichloromethane (50 mL) and then iodine (1.522 g, 6.00 mmol, 1.2 eq) was added. After stirring for 60 min, the resulting purple solution had decolorized and unreacted mercurial was still visible as a white suspension. After 100 min and 240 min, further additions of iodine (0.381 g, 1.5 mmol, 0.3 eq and 0.122 g, 0.50 mmol, 0.1 eq; respectively) were made. After a total of 5 h, the reaction was crystal clear and purple. AG3 X4A resin in the free base form (5.17 g, 2.9 meq/g, 3 eq, Bio-Rad) was added and then hydrogen sulfide was bubbled into the reaction mixture for 5 min. Complete precipitation of mercury(II) was verified by TLC. The reaction was filtered though filter aid and the filter aid was washed with 1:1 methanol-dichloromethane. Silica gel (5 g) was added to the combined filtrates and the reaction mixture was evaporated to dryness. The silica gel was co-evaporated with chloroform (50 mL) and placed on a silica gel column (50 g). Elution with 15%, 20% and 30% methanol in dichloromethane afforded 1.378 g, (78%) of iodocytidine 55 as a white powder. Recrystallization from boiling methanol (35 mL) afforded, after vacuum-drying overnight, 0.953 g, of white needles (mp 179°-180°). Concentration of the mother liquors to 10 mL afforded a second crop of 0.140 g, of pale yellow needles (mp 172°-174°). With the exception of a trace of methanol, both crops (total yield, 62%) were homogeneous according to TLC and NMR.

$^1$H—NMR (DMSO-d$_6$): 8.28 (s, 1H, H6), 7.8 and 6.6 (broad s, 2H, NH$_2$), 6.08 (t, J=6.3, 1H, H1'), 5.20 (d, J=4, 1H, 3'OH), 4.90 (t, J=5, 1H, 5'OH), 4.20 (m, 1H, H4'), 3.77 (distorted q, 1H, H3'), 3.60 and 3.54 (m, 1H, H5'), 2.12 and 1.98 (m, 1 H, H2'). TLC (75:20:5 dichloromethane-methanol-concentrated ammonium hydroxide; UV): starting material, R$_f$=0.15; product 55, 0.33; mercury(II), 0.54.

B. PREPARATION OF 5-(3-TRIFLUOROACETAMIDO1-PROPYNYL)2'-DEOXYCYTIDINE (56)

Iodide 55 (353.1 mg, 1.00 mmol) was coupled for 4 h to N-propargyltrifluoroacetamide following the general procedure given in EXAMPLE 1C. Chomatography of the crude product with a 0–20% methanol in dichloromethane gradient afforded 3.84 g, (102%) of white powder after vacuum drying overnight. This material was homogeneous by TLC, but tenaciously retained solvent. Recrystallization of this powder from boiling isopropanol (10 mL) and cooling to −20° afforded 299.6 mg (74%) alkynylamino nucleoside 56 as white needles (mp 168°-170°). NMR showed that the recrystallized product was homogeneous and that the crystals contained 0.5 molecules of isopropanol per molecule of product 56.

$^1$H—NMR (DMSO-d$_6$): 9.96 (broad s, 1H, NHTFA), 8.15 (s, 1H, H6), 7.83 and 6.86 (broad s, 2H, NH$_2$), 6.10 (t, J=6.5, 1H, H1'), 5.21 (d, J=4.5, 1H, 3'OH), 5.06 (t, J=5, 1H, 5'OH), 4.35 (d, J=4, 0.5H, isopropanol OH), 4.28 (broad s, 2H, —CH$_2$N—), 4.20 (apparent hex, J=3.5, 1H, H4'), 3.79 (m, 1.5H, H3' and isopropanol CH), 3.56 (m, 2H, H5'), 2.13 and 1.97 (m, 1H, H2'), and 1.04 (d, J=6, 3H, isopropanol CH$_3$). TLC (85:13:2 dichloromethane-methanol-concentrated ammonium hydroxide, two elutions; UV): starting iodide 55, R$_f$=0.31; product 56, 0.27.

C. PREPARATION OF 5-(3-AMINO-1-PROPYNYL)2'-DEOXYCYTIDINE 5'-TRIPHOSPHATE (54)

Alkynylamino nucleoside 56 (0.275mmol) was converted to the corresponding 5'-triphosphate and its trifluoroacetyl group was removed following the general procedure given in Example 1E. After addition of the second aliquot of phosphorus oxychloride, phosphorylation was allowed to proceed for 3.5 h. Assuming an absorption coefficient for the product equal to that of the starting material (8,780), the yield of triphosphate 54, based on its UV absorption at 293 nm, was 17%.

EXAMPLE 9

PREPARATION OF 5-(3-TRIFLUOROACETAMIDO1-PROPYNYL)-2'-DEOXYURIDINE (57)

(Compound 57 is an example of an alkynylamino nucleotide (I) wherein R$_1$ is —CH$_2$—, R$_2$ is COCF$_3$, Het is uracil (h), R$_3$, R$_5$, R$_7$ and R$_8$ are H, and R$_6$ is OH.)

5-Iodo-2'-deoxyuridine (7.08 g, 20.0 mmol, Aldrich) was coupled for 4 h to N-trifluoroacetylpropargylamine following the general procedure given in EXAMPLE 1C except that the reaction was run 2.5 times more concentrated than usual. Chromatography of the crude product on silica gel (500 g) with 10–20% methanol in dichloromethane afforded, 3.50 g, (46%) of alkynylamino nucleoside 57 as a tan solid. According to NMR and TLC, this material was >95% pure except for the presence of methanol (about 50 mole %) that was not removed by vacuum-drying.

$^1$H—NMR (DMSO-d$_6$): 11.63 (s, 1H, H3), 10.06 (distorted t, 1H, NHTFA), 8.19 (s, 1H, H6), 6.10 (apparent t, 1H, H1'), 5.23 (d, J=4, 1H, 3'OH), 5.07 (t, J=5, 1H, 5'OH), 4.23 (m, 3H, —CH$_2$—and H4'), 3.8 (apparent q, J=4, 1H, H3'), 3.58 (m, 2H, H5'), and 2.12 (m, 2H, H2').

EXAMPLE 10

PREPARATION OF 5-(5-TRIFLUOROACETAMIDO-1-PENTYNYL)2',3'-DIDEOXYURIDINE (58)

(Compound 58 is an example of structure 5 wherein Het is uracil (h) and R$_1$ is —(CH$_3$)$_3$—.)

A. PREPARATION OF 5-TRIFLUOROACETAMIDO-1-PENTYNE (59)

Sodium hydride (60% dispersion in oil, Alfa) was rendered oil-free by thoroughly and rapidly washing with pentane and then vacuum-drying. Oil-free sodium hydride (4.40 g, 0.110 mole, 1.1 eq) was added in about 20 portions over 25 min to a solution of 5-chloropentyne (10.6 mL, 0.100 mole, 1.0 eq), trifluoroacetamide (14.13 g, 0.125 mole, 1.25 eq), and sodium iodide (14.99 g, 0.100 mole, 1.0 eq) in dry dimethylformamide (250 mL, Aldrich). The reaction mixture was stirred at 25° for 4.5 h and at 60° for 21 h. After cooling, the reaction mixture was added to a solution of potassium dihydrogen phosphate (43.5 g, 0.250 mole, 2.0 eq) in water (500 mL). This solution was extracted with pentane ($2\times500$ mL) and ether ($3\times500$ mL). The combined organic layers were washed with water ($1\times100$ mL), dried over magnesium sulfate, and concentrated with a rotary evaporator. Fractional distillation twice through a 20 cm Vigreux column afforded 8.09 g, (45%) of 5-trifluoroacetamido-1-pentyne (58) as a colorless, mobile liquid (bp 68°°-69° at 13 torr.)

$^1$H—NMR (CDCl$_3$): 6.77 (broad s, 1H, NHTFA), 3.53 (q, J=6.7 and 2.7, 2H, -CH$_2$NHTFA), 2.31 (td, J=6.7 and 2.7, 2H, HCCCH$_2$—), 2.04 (t, J=2.7, 1H, HCCCH$_2$—), and 1.83 (quintet, J=6.7, 2H, —CH2CH2CH2—).

B. PREPARATION OF 5-(5-TRIFLUOROACETAMIDO-1-PENTYNYL)2',3'DIDEOXYURIDINE (58)

5-Trifluroacetamido-1-pentyne (59) was coupled for 4 h to 5-iodo-2',3'-dideoxyuridine (47, prepared as described in Example 2A) according to the general procedure described in EXAMPLE 1C. Chromatography on silica gel (100 g) with a 0-5% methanol in dichloromethane gradient afforded 647.7 mg of alkynylamino nucleoside 58 as a light tan foam. This material was homogeneous by TLC and NMR except for the presence of about 16 mole % of dimethylformamide. Correcting for the presence of dimethylformamide, the yield of desired product was 80%.

$^1$H—NMR (DMSO-d$_6$): 11.52 (s, 1H, H3), 9.47 (distorted t, 1H, NHTFA), 5.90 (q, 1H, H1'), 5.12 (t, 1H, 5'OH), 4.04 (m, 1H, H4'), 3.71 and 3.52 (m, 2H, 5'H), 3.30 (m, 2H, —CH$_2$CH$_2$CH$_2$NHTFA), 2.40 (t, 2H, —CH$_2$CH$_2$CH$_2$NHTFA), 2.23, 2.01 and 1.85 (m, 4H, H2' and H3'), and 1.73 (quintet, 2H, —CH2CH2CH2NHTFA).

EXAMPLE 11

PREPARATION OF 5-(12-TRIFLUOROACETAMIDO-1-DODECYNYL)2',3'-DIDEOXYURIDINE (60)

(Compound 60 is an example of structure 5 wherein Het is uracil (h) and R$_1$ is —(CH$_2$)$_{10}$—.)

A PREPARATION OF 11-DODECYN-1-OL (61)

1-Bromo-10-tetrahydropyranyloxydecane (64.26 g, 0.200 mole, Lancaster, "97+%") was added dropwise over 140 min to a precooled suspension of lithium acetylide ethylenediamine complex (23.94 g, 0.260 mole, 1.3 eq, Aldrich, 90%) in dry dimethylsulfoxide (100 mL) so that the internal temperature remained at 5°-10°. After the addition was complete, the cooling bath was removed and the reaction mixture was stirred for 4.5 h. Water (20 mL) was added dropwise to the reaction mixture. After stirring for 10 min, the reaction mixture was poured into water (300 mL). This solution was extracted sequentially with pentane ($2\times300$ mL) and ether ($2\times300$ mL). Each organic layer was washed individually with water (about 20 mL) and the aqueous washes were combined with the main aqueous layer for re-extraction. The combined organic layers were dried over magnesium sulfate and evaporated to dryness to afford 51.38 g (96%) of crude 12-(tetrahydropyranyloxy)-1-dodecyne as an oil.

A strongly acidic ion exchange resin (AG-50W-X8, 50 g, 5.1 meq/g, Bio-Rad) was added to a solution of the above crude product (49.96 g) in a mixture of chloroform (260 mL) and methanol (260 mL). The suspension was heated at reflux for 4.5 h and then cooled. The reaction mixture was filtered and the filtrate was concentrated. Chromatography of the residue on silica gel (500 g) with 10%, 20% and 30% ethyl acetate in hexanes afforded 31 g, of an oil which was >95% one spot by TLC with detection by phosphomolybdic acid. Distillation of this material through a 20 cm Vigreux column afforded, after a 0.78 g, forerun, 17.91 g, of 11-dodecyn-1-ol (61) as a thick, colorless oil (bp 104-108 at 1.4 torr) which solidified to a white solid on standing. This material was 98% one peak by GC.

$^1$H—NMR (CDCl$_3$) of the chromatographed product before distillation: 3.64 (t, 2H, —CH$_2$OH), 3.37 and 3.33 (m, about 0.2H, impurity), 2.17 (td, 2H, HCCCH$_2$—), 1.92 (t, 1H, HCCCH$_2$—), and 1.2-1.6 (m, 17H, (CH$_2$)$_8$ and OH). IR (thin film of melt): 3392 (O—H), 3311, 2930 and 2854 (C—H), 2160 (acetylene), 1466, 1432, 1394, 1371, 1352, 1328, 1303, 1103, and 1001.

B. PREPARATION OF 12-IODO-1-DODECYNE (62)

Iodine (43.16 g, 170 mmol, 2.0 eq) was added to a suspension of distilled alcohol 61 (15.50 g, 85 mmol), imidazole (17.36 g, 255 mmol, 3.0 eq), and triphenylphosphine (66.90 g, 255 mmol, 3.0 eq) in dry toluene (425 mL, stored over molecular sieves). The reaction mixture was heated at reflux with vigorous stirring for 25 min, generating a yellow solution with a oily black precipitate. After cooling to 25°, saturated aqueous sodium bicarbonate (200 mL) and iodine (23.73 g, 93.5 mmol, 1.1 eq) were added and the reaction was stirred vigorously for 1 h. Saturated aqueous sodium sulfite (40 mL) was added, quenching the purple color. The reaction mixture was allowed to separate into two layers and the organic layer was washed with brine. The organic layer was dried over magnesium sulfate and concentrated. The residue was dissolved in dichloromethane (50 mL) and ether (200 mL) was added. After standing for 30 min, the resulting precipitate (triphenylphosphine oxide) was removed by filtration and washed with ether (100 mL). On further standing, the combined mother liquor and ether wash deposited a second crop of crystals which were removed as before. The combined mother liquors and ether washes were concentrated and dissolved in warm toluene (200 mL). This solution was placed on a silica gel column (500 g) and eluted with toluene (3 L) to afford 13.55 g, (55%) of iodide 62 as a pale yellow mobile liquid. This material was 96% one peak by GC.

$^1$H—NMR (CDCl$_3$): 3.20 (t, 2H, —CH$_2$I), 2.17 (td, 2H, HCCCH$_2$—), 1.94 (t, 1H, HCCCH$_2$—), 1.82, 1.51 and 1.20-1.42 (m, 16H, (CH$_2$)$_8$).

C. PREPARATION OF 12-TRIFLUOROACETAMIDO-1-DODECYNE (63)

Sodium hydride (60% dispersion in oil, Alfa) was rendered oil-free by rapidly and thoroughly washing with pentane and vacuum-drying. Trifluoroacetamide (22.61 g, 200 mmol, 5 eq) was added in about 10 portions over 50 min to a suspension of oil-free sodium hydride (3.84 g, 160 mmol, 4 eq) in dry dimethylformamide (90 mL, Aldrich). When it was discovered early in this addition that the reaction mixture was getting warm, an ice-water bath was added and the rest of the addition was performed at an internal temperature of about 10°. The ice-water bath was removed and the reaction mixture was stirred until hydrogen evolution ceased. After stirring an addition 15 min, a solution of iodide 63 (11.69 g, 40.0 mmol) in dry dimethylformamide (10 mL) was added dropwise over 10 min to the reaction mixture. After stirring for 4 h at 25°, the reaction mixture was rapidly poured into a stirred mixture of saturated aqueous ammonium chloride (200 mL), water (200 mL) and pentane (200 mL). The reaction vessel was rinsed with a mixture of water (50 mL), saturated aqueous ammonium chloride (50 mL) and pentane (200 mL). The combined solutions were allowed to separate into two layers and the aqueous layer was extracted with pentane (2×200 mL). The combined organic layers were dried over magnesium sulfate and evaporated to dryness to yield 10.42 g, (94%) of trifluoroacetamide 63 as an oil which solidified to a waxy solid on standing. Recrystallization of this material from boiling hexanes (100 mL) with slow cooling to −20° afforded 8.145 g (73%) of trifluoroacetamide 63 as pale yellow needles (mp 46°–47°).

$^1$H—NMR (CDCl$_3$): 6.27 (broad s, 1H, NHTFA), 3.34 (apparent q, 2H, —CH$_2$NHTFA), 2.18 (td, 2H, HCCCH$_2$—), 1.94 (t, 1H, HCCCH$_2$—), 1.20–1.65 (m, 16H, (CH$_2$)$_8$). IR (thin film of melt): 3312, 3298, 2932 and 2857 (C-H and N—H), 2117 (acetylene), 1706 (C=O), 1675, 1563, 1460, 1448, 1208, 1182, 1166, 722, and 634.

D. PREPARATION OF 5-(12-TRIFLUOROACETAMIDO1-DODECYNYL)-2',3'-DIDEOXYURIDINE (60)

Protected alkynylamine 63 was coupled for 24 h to 5-iodo-2',3'-dideoxyuridine (47, 676.2 mg, 2.00 mmol, prepared as described in Example 2A) following the general procedure described in EXAMPLE 1C. Chromatography on silica gel (100 g) eluting with a 0–5% methanol in dichloromethane gradient afforded a dark red foam. The red impurity was removed by chromatography on a reverse phase column (100 g, octadecylsilane on 40 micrometer silica gel, Baker) with 40% water in methanol. The appropriate fractions were combined, concentrated, and co-evaporated twice with absolute ethanol to afford 731 mg of alkynylamino nucleoside 60 as a clear oil. This material was homogeneous by TLC and NMR except for the presence of residual ethanol (25 mole %, corrected yield 73%).

$^1$H—NMR (DMSO-d$_6$): 11.49 (broad s, 1H, H3), 9.38 (distorted t, 1H, NHTFA), 8.15 (s, 1H, H6), 5.90 (dd 1H, H1'), 5.12 (distorted t, 1H, 5'OH), 4.35 (t, 0.25H, CH$_3$CH$_2$OH), 4.03 (m, 1H, H4'), 3.72 and 3.52 (m, 2H, H5'), 3.43 (m, 0.5H, CH$_3$CH$_2$OH), 3.16 (quintet, 2H, —CH$_2$NHTFA), 2.34 (t, 2H, propargylic H), 2.16, 2.01, and 1.86 (m, 4H, H2' and H3'), 1.65–1.15 (m, 16H, (CH$_2$)$_8$), and 1.06 (t, 0.75H, CH$_3$CH$_2$OH).

EXAMPLE 12

PREPARATION OF 5-(5-AMINO-1-PENTYNYL)2',3'-DIDEOXYURIDINE (64)

(Compound 64 is an example of an alkynylamino nucleotide (I) wherein Het is uracil (h), R$_1$ is (CH$_2$)$_3$, and R$_2$, R$_3$, R$_5$, R$_6$, R$_7$ and R$_8$ are H.)

A. PREPARATION OF 5-AMINO-1-PENTYNE (65)

Ammonia (340 g, 20 mole) was distilled into a bomb which contained 5-chloropentyne (20.51 g, 0.200 mole) and sodium iodode (7.49 g, 0.050 mole, 0.25 eq). The bomb was sealed and heated in an autoclave at 100° for 12 h. The ammonia was allowed to evaporate and the residue was stirred with a two phase mixture consisting of sodium hydroxide (40 g, 1.0 mole, 5 eq), water (100 mL), and ether (100 mL). The resulting mixture was filtered and allowed to separate into two layers. The organic layer was dried over magnesium sulfate and distilled through a 20 cm Vigreux column. Four fractions (12.46 g, bp 95°–127°, atmospheric pressure) were found by GC to contain significant amounts of product. These fractions were combined and carefully distilled through a spinning band column to afford 6.55 g, (39%) of 5-amino-1-pentyne (65) as a colorless, mobile liquid (bp 125.5°–126°). This material was >99% one peak by GC.

$^1$H—NMR (CDCl$_3$): 2.81 (t, J=7.5, 2H, —CH$_2$NH$_2$), 2.27 (td, J=7.5 and 2.5, 2H, HCCCH$_2$—), 1.96 (t, J=2.5, 1H, HCCCH$_2$—), 1.66 (quintet, J=7.5, 2H, —CH$_2$CH$_2$CH$_2$—), and 1.07 (broad s, 2H, NH$_2$).

B A GENERAL PROCEDURE OF COUPLING UNPROTECTED ALKYNYLAMINES TO IODONUCLEOSIDES. PREPARATION OF 5-(5-AMINO-1-PENTYNE)-2',3'-DIDEOXYURIDINE (64)

A dry, 35-mL, round-bottomed flask was charged with 5-iodo-2',3'-dideoxyuridine (47, 676.2 mg, 2 00 mmol, prepared as described in Example 2A) and then flushed with argon. Dry dimethylformamide (10 mL, Aldrich), dry triethylamine (0.56 mL, 4.0 mmol, 2.0 eq, stored over sieves), 5-amino-1-pentyne (0.59 mL, 6.03 mmol, 3.0 eq), and tetrakis(triphenylphosphine)palladium(O) (231 mg, 0.200 mmol, 0.1 eq, weighed into a vial in a dry box) were added. The resulting suspension was stirred for 45 min, but the palladium catalyst remained at least partly undissolved. Cuprous iodide (190.4 mg, 1.00 mmol, 0.5 eq, Aldrich Gold Label) was added. After stirring for 15 min, a homogenous blue solution had formed and after about 150 min the solution became cloudy. After 200 min, TLC showed that all of starting iodide 47 had been consumed. After 4 h, the reaction mixture was concentrated with a rotary evaporator for about 10 min at 45° and 2 torr. The residue was immediately absorbed onto a silica gel column (100 g) and eluted with a mixture of dichloromethane, methanol and concentrated ammonium hydroxide (400 mL each of 90:9:1, 85:13:2, 75:20:5, 65:30:5 and 50:45:5). The fractions containing the major polar product according to TLC were combined, co-evaporated twice with ethanol, and vacuum-dried overnight to afford 395.9 g, (67%) of alkynylamino nucleoside 64 as a yellow solid. This material was homogeneous by TLC and NMR except for the presence of ethanol (33 mole %) which was not removed by vacuum-drying. The yield of 64, corrected for the presence of ethanol, was 64%.

$^1$H—NMR (DMSO-d$_6$): 8.33 (s, 1H, H6), 5.90 (dd, J=6.6 and 3.0, 1H, H1'), 4.05 (m, 1H, H4'), 3.73 (dd, J=12.1 and 2.8, 1H, H5'a), 3.53 (dd, J=12.1 and 3.1, 1H, H5'b), 2.80 (broad s, 2H, —C$\underline{H}_2$H$_2$), 2.45 (t, J=7.0, 2H, propargylic H), 2.28, 2.02 and 1.86 (m, 4H, H2' and H3'), and 1.70 (quintet, J=7.0 Hz, 2H, —CH$_2$C$\underline{H}_2$C-H$_2$—). This NMR data was obtained form a different batch of 64 prepared in a manner similar to that described above. The signals for the exchangeable hydrogens (H3, 5'OH, and —NH$_2$) in NMR samples of both materials were combined into a single broad (>2 ppm wide) signal which was barely resolved from the baseline.

EXAMPLE 13

PREPARATION OF 5-(3-AMINO-1-PROPYNYL) 2',3'-DIDEOXYURIDINE (66)

(Compound 66 is an example of an alkynylamino nucleotide (I) wherein Het is uracil (h), R$_1$ is CH$_2$, and R$_2$, R$_3$, R$_5$, R$_6$, R$_7$ and R$_8$ are H.)

5-Iodo-2',3'-dideoxyuridine (47, 2.00 mmol) was coupled for 3 h to propargylamine (6.00 mmol, Aldrich) according to the procedure described in Example 12B except that propargylamine was used in place of 5-amino1-pentyne. Chromatography as described above returned 794.5 mg of impure alkynylamino nucleoside 66 as a yellow solid which afforded a single spot when analyzed by TLC. NMR and the mass balance of the reaction indicated that this material was contaminated by ethanol and possibly inorganic impurities.

$^1$H—NMR (DMSO-d$_6$): 11.70 (broad s, 1H, H3), 8.40 (s, 1H, H6), 8.25 (broad s, 2H, NH$_2$), 5.89 (dd, J=6.6 and 3.0, 1H, H1'), 5.13 (t, J=5.0, 1H, 5'OH), 4.07 (m, 1H, H4'), 3.96 (s, 2H, —C$\underline{H}$'NH$_2$), 3.71 and 3.56 (m, 2H, H5'), 2.30, 2.04 and 1.85 (m, 4H, H2' and H3') and signals for ethanol and an unknown impurity. The above NMR data was taken from different preparation of 66 performed as above except that 0.2 eq of cuprous iodide was used and the reaction did not go to completion.

EXAMPLE 14

PREPARATION OF 1-(2-HYDROXYETHOXYMETHYL)5-(3-AMINO-1-PROPYNYL)CYTOSINE TRIPHOSPHATE (67)

(Compound 67 is an example of an alkynylamino nucleotide (I) wherein R$_1$ is —CH$_2$—, R$_2$ and R$_3$ are H, Het is cytosine (i), R$_4$ is (g), and R$_5$ is P$_3$O$_9$H$^3$—.)

A. PREPARATION OF 1-(2-HYDROXYETHOXYMETHYL)5-IODOCYTOSINE (68)

A mixture of 1-(2-hydroxyethoxymethyl)cytosine (1.85 g, 10.0 mmol) and mercuric acetate (3.35 g, 10.5 mmol) was refluxed in methanol (50 mL) and dichloromethane (100 mL). Iodine (3.05 g, 12.0 mmol) was added and the reaction mixture was stirred for 1 h. The free base form of AG3-X4 resin (38 meq) was added and the solution bubbled with hydrogen sulfide for 15 min. The solids were removed by filtration and the filtrate stripped down onto silica gel (10 g). The silica was loaded onto a silica gel column (4×25 cm) and eluted 5%, 10% and 20% methanol in dichloromethane. Evaporation followed by vacuum-drying afforded a colorless solid (1.73 g, 56%).

Recrystallization from 95% ethanol afforded analytically pure material (mp 172°). Calculated for C$_7$H$_{10}$N$_3$O$_3$I: C 27.03%, H 3.24%, N 13.51%. Found: C 27.08%, H3.41%, N13.51%. UV (methanol): maximum at 292.5 (5,300). $^1$H—NMR (DMSO-d$_6$): 3.481 (m, 4H), 4.659 (t, J=5, 1H), 5.070 (s, 2H, 6.665 (broad s, 1H), 7.869 (broad s, 1H), and 8.107 (s, 1H),

B PREPARATION OF 1-(2-HYDROXYETHOXYMETHYL)-5-(3-TRI-FLUOROACETAMIDO-1-PROPYNYL)CYTOSINE (69)

Iodide 68 (311 mg, 1.00 mmol) was coupled to N-propargyltrifluoroacetamide (43) according to the general procedure described in EXAMPLE 1C. Flash chromatography on silica gel (3×20 cm) with 5%, 10% and 20% methanol in dichlormethane afforded alkynylamino nucleotide 69 as a pale yellow foam (77.4 mg, 23%).

$^1$H—NMR(DMSO-d$_6$): 3.472 (broad s, 4.276 (d, J=5.0, 2H), 4.653 (broad t, J=4.5, 1H), 5.091 (s, 2H), 6.925 (broad s, 1H), 8.037 (s, 1H), and 9.964 (broad s, 1H),

C. PREPARATION OF 1-(2-HYDROXYETHOXYMETHYL)5-(3-AMINO-1-PROPYNYL)CYTOSINE (67)

The hydroxyl group of the sugar part of alkynylamino nucleoside 69 (0.167 mmol) was converted to a triphosphate and the trifluoroacetyl group was removed following the general procedure given in Example 1E. After addition of the second aliquot of phosphorus oxychloride, phosphorylation was allowed to proceed for for 75 min. Assuming an absorption coefficient for the product equal to that of the starting material (7,790), the yield of triphosphate 67, based on its UV absorption at 291 nm, was 21%.

EXAMPLE 15

Preparation of N-Hydroxysuccinimide Ester 2a (A preferred reagent for attaching a 505 nm fluorescent dye to an alkynylamino-nucleotide wherein R$_9$ and R$_{10}$ are H).

A. Preparation of 9-(Carboxyethylidene)-3,6-dihydroxy-9H-xanthene (SF-505)

Resorcinol (33.0 g, 0.300 mol) and succinic anhydride (30.0 g, 0.300 mol) were placed in a round bottomed flask and purged with nitrogen. Methanesulfonic acid (150 mL) was added and the solution was stirred at 65° C. for 2 hours under an atmosphere of nitrogen. The reaction mixture was added dropwise to rapidly stirred, ice-cooled water (1 L) with simultaneous addition of 50% aqueous sodium hydroxide to maintain pH 2.5+/0.5. The product which appeared as a granular precipitate was collected by filtration and rinsed with water (3×100 mL) then acetone (3×100 mL). The product was air-dried then vacuum-dried (vacuum oven) at 110° C. for 18 hours to afford a dark red powder (37.7 g, 88%).

An analytical sample was prepared by dissolving 1.0 g, of product in 25 mL of hot 0.3N HCl. The precipitate which formed on cooling was removed by filtration and discarded. Dilute aqueous sodium hydroxide was added to raise the pH to 1.25. The resulting precipitate was collected by filtration, rinsed with water, air-dried then vacuum-dried over P₂O₅ at 140° C. for 36 hours.

Anal: Calc. [C(16)H(12)O(5)] C 67.60, H 4.26.

Found: C 67.37. H 4.34. 0.52% water (K-F). NMR (DMSO-d₆): (mostly spirolactone form) δ 2.690 (t, J=8.6 hz, 2H): 3.070 (t, J=8.6 hz, 2H), 6.530 (d, J=1 8 hz, 2H); 6.676 (dd. J=8.7. 1.8 hz, 2H), 7.432 (d, J=8.7, 1.8 hz, 2H), 7.432 (d, J=8.7 hz, 2H), and 9.964 (s, 2H), Vis. abs. (pH 8.2; 50 mM aq is/HCl): max 486 nm (72,600).

B. Preparation of 9-(2-Carboxyethyl)-3.6-diacetoxy9-ethoxy-9H-xanthene (Ac2EtSF-505)

SF-505 (29.3 g, 103 mmol] as added to ice-cold acetic anhydride (500 mL) followed by pyridine (100 mL). The mixture was stirred in ice for 20 minutes then added over 20 minutes to rapidly stirred ice-cold water (7 L). After stirring for an additional 30 minutes, the intermediate product was filtered and resuspended in water (4 L) and stirred for another 30 minutes. The solid was collected by filtration, dissolved in absolute ethanol (1 L), and refluxed for 45 minutes. The solution was concentrated on a rotary evaporator to 200 mL which resulted in crystallization. The product was collected by filtration air-dried then vacuum-dried to afford pale-orange microcrystals (21.9 g, 51%).

Recrystallization from methylene chloride/cyclohexane gave colorless microcrystals. M.p.: 142°-143° C. Anal: Calc. [C(22)H(22)O(8)] C 6.63.76, H 5.35. Found: C 63.58, H 5.39. NMR (DMSO-d₆): δ 1.035 (t, J=6.9 hz, 3H), 1.667 (m, 2H), 2.232 (m, 2H), 2.294 (s, 6H), 2.888 (q, J=6.9 hz, 2H), 7.0–7.1 (m, 4H), and 7.575 (d, J=9.1 hz, 2H).

C. Preparation of 9-(2-(N-Succinimidyloxycarbonyl))ethyl)-3,6-diacetoxy-9-ethoxy-9H-xanthene (Ac2EtSF-505-NHS)

Ac2EtSF-505 (10.4 g, 25.1 mmol) was mixed with methylene chloride (300 mL) and 1-(3-dimethylaminopropyl)-3-ethylcarbodiimide hydrochloride (9.70 g. 50.6 mmol) and N-hydroxysuccinimide (4.32 g, 37.5 mmol) were added. The mixture was stirred for one hour and then washed with water (5×50 mL). The combined aqueous layers were back extracted with methylene chloride (50 mL) and the pooled organic layers were dried over sodium sulfate and stripped down. Trituration with ethanol (75 mL) followed by filtration and air-drying afforded the crude product as a light yellow solid (c. 10 g). This material was dissolved in methylene chloride (50 mL) and cyclohexane (50 mL) was added. One teaspoon of charcoal was added, the mixture was filtered, and the product was brought down with an additional portion of cyclohexane (100 mL). Collection by filtration. air-drying, and vacuum-drying afforded colorless crystals (6.94 g, 54%).

A second crystallization from ethanol afforded an analytical sample. M.p.: 162°-3° C. Anal: Calc. [C(26)H(25)N(1)O(10)] C 61.05, H, 4.93,N 2.74. Found: C 60.78, H 5.01N 2.65. NMR (DMSO-d₆): δ 1.056 (t, J=7.0 hz, 3H), 2.4–2.1 (m, 4H), 2.293 (s, 6H), 2.757 (s, 4H), 2.922 (q, J=7.0 hz, 2H), 7.069 (m, 4H), and 7.617 (p d, J=9.1 hz, 2H.)

D. Preparation of 9-(2-(N-methyl-N-(benzyloxycarbonylmethyl)carboxamido)ethyl)-3,6-diacetoxy9-ethoxy-9H-xanthene (Ac2EtSF-505-Sar-OBn)

To a solution of sarcosine benzyl ester* (1.13 g, 6.31 mmol) in methylene chloride (50 mL) was added Ac-2EtSF-505-NHS (2.58g, 5.05 mmol) and 5% aq sodium bicarbonate solution (30 mL). The two-phase mixture was stirred rapidly for 20 hours. The layers were separated and the organic layer washed with 3×15 mL water, dried over sodium sulfate and concentrated to 25 mL. The solution was diluted to 150 mL with cyclohexane, charcoal-treated, and reduced to 75 mL under a stream of nitrogen resulting in the precipitation of the product. The supernatant was decanted away and the residue coevaporated with methylene chloride to afford a colorless foam (1.70 g, 58%).

* Sarcosine benzyl ester p-tosylate salt (Adams Chemical Co.) was taken up in methylene chloride and washed repeatedly with 5% aqueous sodium bicarbonate, then water washed, dried over sodium sulfate, and stripped down.

Extensive vacuum-drying afforded an analytical sample. Anal: Calc. [C(32)H(33)N(1)O(9)] C 66.77 H 5.78, N 2.43. Found: C 66.66, H 5.89, N 2.25. NMR (DMSO-d₆): (Shows 5:2 mixture of amide bond rotamers.) δ (major and minor) 1.040 and 1.018 (t J=6.7 hz, 3H), 1.789 and 1.670 (m, 2H), 2.211 (m, 2H), 2.290 and 2.276 ·(s, 6H), 2.713 and 2.695 (s, 3H), 2.893 (q, J=6 7 hz, 2H), 3.963 (s, 2H), 5.075 and 5.039 (s, 2H), 7.044 (m, 4H), 7.324 (m, 5H), and 7.573 and 7.516 (p d, J=9.2 hz, 2H).

E. Preparation of 9-(2-(N-Methyl-N-(N'-succinimidyloxycarbonylmethyl)carboxamido)ethyl)-3,6-diacetoxy-9-ethoxy-9H-xanthene (Ac2EtSF-505-Sar-NHS, Structure 2a)

To a solution of Ac2EtSF-505-Sar-OBn (1.55 g 2.69 mmol) in absolute ethanol (60 mL) was added 10% palladium on carbon (0.15 g). The mixture was stirred under balloon pressure of hydrogen for 30 minutes. The catalyst was removed by filtration and the ethanol stripped off to afford a syrupy residue.

This residue was dissolved in methylene chloride (85 mL) and N-hydroxysuccinimide (0.495 g, 4.30 mmol) and 1-(3-dim ethylaminopropyl)-3-ethylcarbodiimide hydrochloride (1.12 g, 5.84 mmol) were added (4×25 mL). The solution was concentrated to 25 mL diluted to 175 mL with cyclohexane, charcoal treated and reduced in volume to 75 mL under a stream of nitrogen. The solid product was collected by filtration, air-dried, and vacuum-dried to afford a colorless Powder (0.97 g, 62%).

Coevaporation with methylene chloride followed by extensive vacuum-drying at 40° C. removed traces of cyclohexane and afforded an analytical sample as an amorphous solid. Anal: Calc. [C(29)H(30)N(2)O(11)] C 59.79, H 5.19, N 4.81. Found: C 59.37, H 4.62, N 4.62, 0.93% water (K-F). NMR (DMSO₆): (Shows a 4:1 mixture of amide bond rotamers.) δ (major and minor) 1.034 (t, J=6.9 hz, 3H), 1.827 and 1.935 (m, 2H), 2.223 (m, 2H), 2.289 (s, 6H), 2.758 (s, 4H), 2.779 and 2.824 (s, 3H), 2.888 (q, J=6.8 hz, 2H), 4.333 and 4.473 (s, 2H), 7.043 (m, 4H), and 7.587 (per d, J=9.1 hz, 2H).

EXAMPLE 16

Preparation of N-Hydroxysuccinimide Ester 2b (A preferred reagent for attaching a 512 nm fluorescent dye to an alkynylamino-nucleotide wherein $R_9$ is H and $R_{10}$ is $CH_3$)

A. Preparation of 4-Methylresorcinol 2,4-Dihydroxybenzaldehyde (33.97 gm, 0.246 mol) (recrystallized from toluene) was dissolved in spectroscopic grade 2-propanol (3 L) in a round bottom flask fitted with a gas inlet and a bubbler outlet. 10% Palladium on carbon (1.35 gm) was added followed by phosphoric acid (3 mL) and the mixture was sparged with nitrogen. The nitrogen flow was switched to hydrogen and the mixture was rapidly stirred with ice cooling. After 3 hours hydrogen uptake was complete and the catalyst was removed by filtration. The filtrate was stripped down to 200 mL and 200 mL of ethyl acetate was added. The solution was washed with 4×200 mL of water and the combined water extracts back-extracted with ethyl acetate. These organic extracts were water washed and the combined organic layers dried over sodium sulfate and stripped down to afford the product as a colorless crystalline solid (29.95 gm, 98%). M.p.: 106° C. (Lit. 106°–107° C. [J. C. Bell W. Bridge, and A. Robertson, *J. Chem. Soc.*, 1542-45 (1937)]). NMR (DMSO-$d_6$): δ 1.961 (s, Me). 6.076 (dd, H-6, J[5, 6]=8 hz, J[2,6]=2 hz), 6.231 (d, H-2), 6.760 (d, H-5) 8.867 (s, OH), and 9.008 (s, OH).

B. Preparation of 9-Carboxyethylidene-3,6-dihydroxy2,7-dimethyl-9H-xanthene (SF-512)

4-Methylresorcinol (25.8 g, 0.208 mol) and succinic anhydride (20.8 g, 0.208 g) were placed in a round bottom flask and the flask was purged with nitrogen. Methanesulfonic acid (150 mL) was added and the solution heated under nitrogen to 65° C. for 2 hours. The solution was added dropwise to 1 L of rapidly stirred, ice-cooled water with the simultaneous addition of 50% ag sodium hydroxide to maintain the pH at 2.25+/−0.25. The product was collected by centrifugation and washed with water (3×) and acetone (2×). The solid was air-dried, then vacuum-dried at 110° C. to afford a brick-red powder (24.1 g, 74%).

Purification was effected by allowing ethyl acetate to slowly diffuse into a solution of the product in dimethyl sulfoxide. The precipitate was collected by filtration, air-dried, then vacuum-dried. NMR (DMSO-$d_6$): (Shows pure delta form along with one mole each of water and dimethyl sulfoxide.) δ 2.124 (s, 6H), 3.421 (d, J=7.2 hz 2H), 5.769 (t, J=7.2 hz, 1H); 6.512 (s, 1H), 6.573 (s, 1H); 7.295 (s, 2H), 9.681 (s, 1H), 9.825 (s, 1H), and 12.346 (bs, 1H), Vis. abs. (pH 8.2 aq Tris): max 493.5 nm.

C. Preparation of 9-Carboxyethyl-3.6-diacetoxy-2,7-dimethyl-9-ethoxy-9H-xanthene (Ac2EtSF-512)

A sample of SF-512 (20.0 g, 64.0 mmol) was added to acetic anhydride (350 mL) followed by pyridine (80 mL). This was stirred for 1 hour and then filtered to remove traces of unreacted dye. The filtrate was poured into 3.5 L of rapidly stirred water. The solid intermediate was collected by filtration, resuspended in 2 L cold water, stirred for 15 minutes, then recollected and air-dried to afford the spirolactone intermediate (20.8 g).

This was dissolved in absolute ethanol (600 mL) and refluxed for 45 minutes. The solution was charcoal-treated and concentrated to 300 mL. The product was collected by filtration, rinsed with cold ethanol (2×50 mL), air-dried, and then vacuum-dried to afford colorless microcrystals (14.9 g, 53%), M.p.: 143° C. Anal: Calc. [C(24)H(26)O(8)] C 65.15, H 5.92. Found: C 65.31, H 5.97. NMR (DMSO-$d_6$): δ 1.027 (t, J=6.9 hz, 3H), 1.628 (m, 2H), 2.136 (s, 6H), 2.207 (m, 2H), 2.303 (s, 6H), 2.884 (q, 6.9 hz, 2H), 6.939 (s, 2H), and 7.417 (s, 2H).

D. Preparation of 9-(2-(N-Succinimidyloxycarbonyl)ethyl)-3,6-diacetoxy-2,7-dimethyl-9-ethoxy-9H-xanthene (Ac2EtSF-512-NHS)

To a solution of Ac2EtSF-512 (9.42 g, 21.3 mmol) in methylene chloride (175 mL) was added N-hydroxysuccinimide (3.62 g, 31.5 mmol) followed immediately by 1-(3-dimethylaminopropyl)-3-ethylcarbodiimide hydrochloride (8.05 g, 42.0 mmol). The solution was stirred at room temperature for 2 hours. The mixture was washed with water (4×100 mL) and the aqueous washings back-extracted with methylene chloride (2×50 mL). The combined organic layers were dried over sodium sulfate and stripped down to an oil. Absolute ethanol was added and crystallization was induced by scratching. The product was collected by filtration air-dried, then vacuum-dried to afford pale-orange microcrystals (9.80 g, 85%).

An analytical sample was prepared by dissolving 1 g, in methylene chloride (10 mL) and adding cyclohexane (40 mL). Charcoal treatment followed by cooling and scratching induced crystallization affording a colorless crystalline solid. M.p.: 159° C. Anal: Calc. [C(28)H(29)N(1)O(10)] C 62.33, H 5.42, N 2.60. Found: C 62.06 H 5.71. N 2.39. NMR (DMSO-$d_6$): δ 1.053 (t, J=6.9 hz, 3H), 2.149 (s, 6H), 2.304 (s, 6H), 2.1–2.4 (m, 4H), 2.747 (s, 4H), 2.920 (q, J=6.9 hz, 2H), 6.975 (s, 2H), and 7.464 (s, 2H).

E. Preparation of 9-(2-(N-methyl-N-(benzyloxycarbonylmethyl)carboxamido)ethyl)-3.6-diacetoxy2.7-dimethyl-9-ethoxy-9H-xanthene (Ac2EtSF-512-Sar-OBn)

To a solution of sarcosine benzyl ester (0.72 g, 4.02 mmol) in methylene chloride (25 mL) was added Ac-2EtSF-512-NHS (1.73 g, 3.21 mmol) and 5% aq sodium bicarbonate solution (20 mL). The two-phase mixture was stirred rapidly for 20 hours. The layers were separated and the organic layer washed with 3×15 15 mL water, dried over sodium sulfate, and concentrated to 10 mL. The solution was diluted to 60 mL with cyclohexane, charcoal-treated, and reduced to 25 mL under a stream of nitrogen resulting in the precipitation of the product. The supernatant was decanted and the colorless solid vacuum-dried (1.44 g, 74%).

Recrystallization from methylene chloride/cyclohexane with charcoal treatment afforded an analytical sample. M.p.: 150°–2° C. Anal: Calc. [C(34)H(37)N(1)O(9)] C 67.65 H 6.18N 2.32. Found: C 67.42 H 6.08N 2.33. NMR (DMSO-$d_6$) (Shows 5:2 mixture of amide bond rotamers ) δ (major and minor) 1.049 and 1.008 (t, J=6.8 hz, 3H), 1.747 and 1.66 (m, 2H), 2.144 and 2.115 (s, 6H), 2.18 (m, 2H), 2.314 and 2.303 (s, 6H), 2.694 (s, 3H), 2.907 and 2.884 (q, J=6.8 hz, 2H), 3.961 (s, 2H), 5.075 and 5.016 (s, 2H), 6.960 and 6.917 (s, 2H), 7.430 and 7.396 (s, 2H), and 7.30 (m, 5H).

F. Preparation of 9-(2-(N-Methyl-N-(N'-succinimidyloxycarbonylmethyl)carboxamido)ethyl)-3,6-diacetoxy-9-ethoxy-2,4,5,7-tetramethyl-9H-xanthene (Ac2EtSF-512-Sar-NHS. Structure 2b)

To a suspension of Ac2EtSF-512-Sar-OBn (0.45 g, 0.745 mol) in absolute ethanol (20 mL) was added 10% palladium on carbon (0.05 g). The mixture was stirred under balloon pressure of hydrogen for 30 minutes. The catalyst was removed by filtration and the ethanol stripped off to afford a syrupy residue.

This residue was dissolved in methylene chloride (25 mL) and N-hydroxysuccinimide (0.129 g, 1.12 mmol) and 1-(3-dimethylaminopropyl)-3-ethylcarbodiimide hydrochloride (0.292 g, 1.52 mmol) were added. The mixture was stirred for 30 minutes and then washed with water (3×15 mL). The solution was dried over sodium sulfate, concentrated to 10 mL, diluted to 40 mL with cyclohexane charcoal treated and reduced in volume to 20 mL under a stream of nitrogen. The supernatant was decanted and the residue subjected to a second precipitation from methylene chloride to afford a colorless powder (0.27 g, 59%). Anal: Calc. [C(31)H(34)N(2)O(11)] C 60.98, H 5.61, N 4.59. Found: C 60.28, H 5.71, N 4.40, 1.08% water (K-F). NMR (DMSO-d$_6$); (Shows a 5:1 mixture of rotamers about the amide bond.) δ (major and minor) 1.043 (t, J=7.0 hz, 3H), 1.793 and 1.933 (m, 2H), 2.145 and 2.133 (s, 6H), 2.198 (m, 2H), 2.314 (s, 6H), 2.740 (s, 4H), 2.778 and 2.821 (s, 3H), 2.900 (q, J=7.0 hz, 2H), 4.334 and 4.469 (s, 2H), 6.960 and 6.925 (s, 2HO, and 7.441 (s, 2H).

EXAMPLE 17

Preparation of N-Hydroxysuccinimide Ester 2c (A preferred reagent for attaching a 519 nm fluorescent dye to an alkynylamino-nucleotide where-in R$_9$ is CH$_3$ and R$_{10}$ is H)

A. Preparation of 9-(2-Carboxyethylidene)-3,6-dihydroxy-4,5-dimethyl-9H-xanthene (SF-519)

2-Methylresorcinol (37.2 g, 0.300 mol) and succinic anhydride (30.0 g, 0.300 mol) were Placed in a round bottomed flask and purged with nitrogen. Methanesulfonic acid (150 mL) was added and the solution was stirred at 65° C. for 4 hours under an atmosphere of nitrogen. The reaction mixture was added dropwise to rapidly stirred, ice-cooled water 1 L) with simultaneous addition of 50% aqueous sodium hydroxide to maintain pH 6.0+/−0.5. The finely divided solid was collected by centrifugation and rinsed with water (4×250 mL), each time resuspending, spinning down, and discarding the supernatant. The crude product was suspended in water (1 L) and sufficient aqueous sodium hydroxide (50%) was added to raise the pH to 10.2. The solution was filtered and the filtrate brought to pH 1.2 with concentrated HCl. The product was collected by centrifugation and rinsed with water (3×350 mL) and acetone (3×250 mL) as described above. The resulting solid was azeotroped with toluene, collected by filtration, and vacuum-dried at 110° C. to afford a brick-red powder (24.6 g, 53%). Anal: Calc. [C(18)H(16)O(5)] C 69.22 H 5.16. Found: C 68.95 H 5.30, 0.80% water (K-F). NMR (DMSO-d$_6$) (mostly delta form): δ 2.164 (s, 3H), 2.177 (s, 3H), 3.376 (d, J=7.1 hz, 2H), 5.749 (t, J=7.2 hz, 1H), 6.642 (d, J=8.8 hz, 1H), 6.672 (d, J=8.8 hz, 1H), 7.216 (d, J=8.5 hz, 1H), 7.227 (d, J=8.5 hz, 1H), 9.602 (bs, 1H), and 9.758 (bs, 1H), Vis. abs. (pH 8.2; 50 mM aq Tris/HCl) max 500 nm (69,800).

B. Preparation of 9-(2-Carboxyethyl)-3.6-diacetoxy4.5-dimethyl-9-ethoxy-9H-xanthene (Ac2EtSF-519)

SF-519 (15.0 g, 48.0 mmol) was added to acetic anhydride (250 mL) and the solid was pulverized. (Sonication is useful to disperse the highly insoluble SF-519.) The suspension was ice-cooled, pyridine (50 mL) was added, and the mixture stirred for 20 minutes. The solution was filtered and added in a slow but steady stream to rapidly stirred ice-cold water (4 L). After stirring for an additional 20 minutes the intermediate product was filtered, resuspended in water (3 L). and stirred for another 25 minutes. The solid was collected by filtration and air-dried. The dried intermediate was dissolved in absolute ethanol (600 mL) and refluxed for 1 hour. The solution was concentrated on a rotary evaporator to 200 mL which resulted in crystallization. The product was collected by filtration, air-dried, then vacuum-dried to afford colorless microcrystals (12.13 g, 57%).

An analytical sample was prepared by precipitation from methylene chloride solution with cyclohexane. NMR (DMSO-d$_6$): δ 1.033 (t, J=6.9 hz, 3H), 1.674 (m, 2H), 2.189 (s, 6H), 2.19 (m, 2H), 2.348 (s, 6H) 2.878 (q, J=6.9 hz, 2H), 7.006 (d, J=8.6 hz, 2H), and 7.399 (d J=8.6 hz 2H).

C. Preparation of 9-(2-(N-Succinimidyloxycarbonyl)ethyl-3,6-diacetoxy-4,5-dimethyl-9-ethoxyl9H-xanthene (Ac2EtSF-519-NHS)

Ac2EtSF-519. (7.80 g, 17.6 mmol) was mixed with methylene chloride (175 mL) and N-hydroxysuccinimide (2.75 g, 23.9 mmol) and 1-(3-dimethylaminopropyl)-3-ethylcarbodiimide hydrochloride (7.00 g, 36.5 mmol) were added. The mixture was stirred for 90 minutes and then washed with water (5×100 mL). The combined aqueous layers were back extracted with methylene chloride (2×50 mL) and the pooled organic layers were dried over sodium sulfate and stripped down. Trituration with ethanol (100 mL) followed by filtration and air-drying afforded the product as a light yellow solid (7.45 g, 78%).

Two recrystallizations from cyclohexane/methylene chloride with charcoal treatment afforded an analytical sample. M.p.: 164°–5° C. Anal: Calc. [C(28)H(29)N(1)O(10)] C 62.33, H 5.42, N 2.60. Found: C 62.17, H 5.47, N 2.48. NMR (DMSO-d$_6$: δ 1.051 (t, J=7.0 hz, 3H), 2.4-2.1 (m, 4H), 2.191 (s, 6H), 2.337 (s, 6H), 2.715 (s, 4H), 2.912 (q, J=7.0 hz, 2H), 7.015 (d, J=8.6 hz, 2H), and 7.429 (d, J=8.6 hz, 2H).

D. Preparation of 9-(2-(N-methyl-N-(benzyloxycarbonylmethyl)carboxamido)ethyl)-3,6-diacetoxy-4,5-dimethyl-9-ethoxy-9H-xanthene (Ac2EtSF-519-Sar-OBn)

To a solution of sarcosine benzyl ester (0.557 g, 3.11 mmol) in methylene chloride (19 mL) was added Ac2EtSF-519-NHS (1.30 g, 2.41 mmol) and 5% aqueous sodium bicarbonate solution (15 mL). The two-phase mixture was stirred rapidly for 18 hours. The layers were separated and the organic layer washed with 3×10 mL water, dried over sodium sulfate, and concentrated to 10 mL. The solution was diluted to 40 mL with cyclohexane, charcoal-treated and reduced to 20 mL under a stream of nitrogen resulting in the precipitation of the product as a sticky solid. The supernatant was decanted away and the residue coevaporated with methylene chloride to afford a colorless foam (0.97 g, 67%).

Extensive vacuum drying afforded an analytical sample. Anal: Calc. [C(34)H(37)N(1)O(9)]C 67.65 H 6.18 N 2.32. Found: C 67.43 H 6.37 N 2.32. NMR (DMSO-d$_6$) (Shows 5:2 mixture of amide bond rotamers.): δ (major and minor) 1.044 and 1.020 (t=7.0 hz, 3H), 1.824 and 1.714 (m, 2H), 2.17 (m, 2H), 2.195 and 2.169 (s, 6H), 2.346 and 2.337 (s, 6H), 2.720 and 2.691 (s, 3H), 2.889 (q, J=7.0 hz, 2H), 3.959 and 3.988 (s, 2H), 5.073 and 5.048 (s, 2H), 7.000 and 6.954 (d, J=8.6 hz, 2H), and 7.45–7.25 (m, 7H).

E. Preparation of 9-(2-(N-Methyl-N-(N'-succinimidyloxycarbonylmethyl)carboxamido)ethyl)-3,6-diacetoxy-4,5-dimethyl-9-ethoxy-9H-xanthene (Ac2EtSF-519-Sar-NHS, Structure 2c)

To a solution of Ac2EtSF-519-Sar-OBn (1.35 g, 2.24 mmol) in absolute ethanol (50 mL) was added 10% Palladium on carbon (0.13 g). The mixture was stirred under balloon pressure of hydrogen for 20 minutes. The catalyst was removed by filtration and the ethanol stripped off to afford a syrupy residue.

This residue was dissolved in methylene chloride (50 mL) and N-hydroxysuccinimide (0.39 g, 3.39 mmol) and 1-(3-dimethylaminopropyl)-3-ethylcarbodiimide hydrochloride (1.57 g, 8.19 mmol) were 15 added. The mixture was stirred for 75 minutes and then washed with water (4×15 mL). The solution was dried over sodium sulfate concentrated to 25 mL. diluted to 125 mL with cyclohexane, charcoal treated, and reduced in volume to 50 mL under a stream of nitrogen. The supernatant was decanted and the remaining oil taken up in methylene chloride (5 mL) and added dropwise to rapidly stirred cyclohexane (75 mL) to afford a colorless powder (0.587 g, 43%).

To provide an analytical sample a portion of the product was taken up in methylene chloride, dried over molecular sieves, evaporated under a stream of nitrogen, and finally dried in a drying pistol at 48° C. over phosphorus pentoxide for 20 hours. Anal: Calc. [C(31)H(34)N(2)O(11)]; C 60.98, H 5.61, N 4.59. Found: C 60.15, H 5.71, N 4.51, water (K-F) 1.51%. NMR (DMSO-d$_6$) (Shows a 4:1 mixture of amide bond rotamers.): δ (major and minor) 1.039 (t, J=6.9 hz, 3H), 1.841 and 1.945 (m, 2H), 2.19 (m, 2H), 2.194 (s, 6H), 2.345 (s, 6H), 2.767 and 2.744 (s, 4H), 2.778 and 2.825 (s, 3H), 2.888 (q, J=6.9 hz, 2H), 4.328 and 4.461 (s, 2H), 7.000 (d J=8.6 hz, 2H), and 7.410 (d, J=8.6 hz, 2H).

EXAMPLE 18

Preparation of N-Hydroxysuccinimide Ester 2d (A preferred reagent for attaching a 526 nm dye to an alkynylamino-nucleotide wherein R$_9$ and R$_{10}$ are CH$_3$)

A. Preparation of 2,4-Dihydroxy-3-methylbenzaldehyde

Phosphorus oxychloride (80 mL, 0.86 mol) was added to a stirred mixture of N-methylformanilide (102 mL, 0.82 mol) in ether (250 mL). The mixture was stirred for 1 hour at room temperature and then cooled in ice. 2-Methyl resorcinol (Aldrich, 100 g 0.81 mol) was added and the mixture was allowed to warm to room temperature while stirring overnight. The precipitated intermediate product was collected by filtration and rinsed with ether (3×). The intermediate was hydrolyzed by dissolving in a mixture of acetone (250 mL) and water (250 mL) and stirring for 30 minutes. Water (2 L) was added, the mixture was brought to a boil, and then allowed to cool and deposit crystalline product. This was recrystallized a second time from water (4 L) to afford pure product (70 g, 57%). M.p. 150° C. (Lit. 152°–3° C. [W. Baker et al., *J. Chem. Soc.*, 2834–5 (1949).]. NMR (DMSO-d$_6$): δ 1.973 (s, 3H), 6.551 (d, J=8.5 hz, 1H), 7.428 (d, J-8.5 hz, 1H), 9.703 (s, 1H), 10.745 (s, 1H), and 11.592 (s, 1H).

B. Preparation of 2,4-dimethylresorcinol

A solution of 2,4-dihydroxy-3-methylbenzaldehyde (30.0 g, 197 mmol) with isopropanol (3 L) was ice-cooled in a 5 L 3-neck flask fitted with a magnetic stirrer. Phosphoric acid (4 mL) and 10% palladium on carbon were added and the solution was sparged with nitrogen, then hydrogen. When uptake was judged to be complete (c. 1.5 hour) the solution was again sparged with nitrogen and then filtered through Celite ®. The solvent was stripped off, the residue taken up in ethyl acetate, and the resulting solution washed with water (4×100 mL). The water washes were back-extracted with ethyl acetate and the combined organic layers dried over sodium sulfate and stripped down. Sublimation (95°, 0.05 torr) afforded a colorless solid (19.6 g, 72%). M.p. 107–8° C. (Lit. 108–109° C. [W. Baker et al., *J. Chem. Soc.*, 2834–5 (1949).]). NMR (DMSO-d$_6$): δ 1.969 (s, 3H), 2.037 (s, 3H), 6.220 (d, J=8.1 hz, 1H), 6.637 (d, J=8.1 hz, 1H), 7.929 (s, 1H), and 8.785 (s, 1H).

C. Preparation of 9-(2-Carboxyethylidene)-3,6-dihydroxy-2,4,5,7-tetramethyl-9H-xanthene (SF-526)

2,4-Dimethylresorcinol (28.4 g, 0.205 mol) and succinic anhydride (20.0 g, 0.200 mol) were placed in a round bottomed flask and purged with nitrogen. Methanesulfonic acid (231 mL) was added and the solution was stirred at 70° C. for 20 hours under an atmosphere of nitrogen. The reaction mixture was added dropwise to a rapidly stirred mixture of aqueous sodium hydroxide (95 g, in 150 mL water) and ice (3 L). Sufficient methanesulfonic acid was added to bring the final pH from 4.7 to 1.5. The resulting solid was collected by centrifugation and washed by suspending, spinning down, and decanting from water (5×1.2 L). The final suspension was collected by filtration, air-dried, then oven-dried at 110° C. for 6 hours to afford a brick-red solid (30.6 g, 44%).

A second precipitation from alkaline solution, followed by centrifugation and water washes afforded an analytical sample. Anal: Calc. [C(16)H(12)O(5)] C 70.57. H 5.92. Found: C 70.39, H 6.00, 0.21% water (K-F). NMR (DMSO-d$_6$) (mostly spirolactone form): δ 2.172 (s, 12H), 2.508 (m, 2H), 3.342 (m, 2H), and 7.604 (s, 2H), Vis. abs. (pH 8.2; 50 mM ag Tris/HCl): 509 nm (71,300).

D. Preparation of 9-(2-Carboxyethyl)-3,6-diacetoxy9-ethoxy-2,4,5,7-tetramethyl-9H-xanthene (Ac2EtSF-526)

SF-526 (25.2 g, 74 mmol) was added to ice-cold acetic anhydride (450 mL) followed by pyridine (100 mL) and the mixture was stirred with ice-cooling for 150 minutes. The reaction mixture was filtered then added in a slow, steady stream to rapidly stirred, ice-cold water (7 L). After stirring for an additional 30 minutes, the intermediate product was filtered, washed with water, resuspended in water (4 L) and stirred for another 30 minutes. The solid was collected by filtration and air-dried to afford the spirolactone intermediate (28.9 g). A portion of this intermediate (18.6 g) was dissolved in absolute ethanol (1 L), and refluxed for 90 minutes. The solution was concentrated on a rotary evaporator to 300 mL which resulted in crystallization. The product was collected by filtration rinsed with ethanol, air-dried, then vacuum-dried to afford colorless microcrystals (11.6 g, 52% based on amount of intermediate used).

Recrystallization from methylene chloride/cyclohexane with charcoal treatment gave colorless microcrystals. M.p.: 154–155° C. Two evaporations from methylene chloride removed traces of cyclohexane for analysis. Anal: Calc. [C(20)H(20)O(5)] C 70.57, H 5.92. Found: C 70.39, H 6.00, 0.21% water (K-F). NMR (DMSO-$d_6$) (mostly spirolactone form): δ 2.172 (s, 12H), 2.508 (m, 2H), 3.342 (m, 2H), and 7.604 (s, 2H), Vis. abs. (pH 8.2; 50 mM aq Tris/HCl): 509 nm (71,300).

E. Preparation of 9-(2-(N-Succinimidyloxycarbonyl)ethyl)-3,6-diacetoxy-9-ethoxy-2,4,5,7-tetramethyl9H-xanthene (Ac2EtSF-526-NHS)

Ac2EtSF-526 (4.70 g, 9.99 mmol) was mixed with methylene chloride (75 mL) and 1-(3-dimethylaminopropyl)-3-ethylcarbodiimide hydrochloride (3.10 g, 16.2 mmol) and N-hydroxysuccinimide (1.50 g, 13.0 mmol) were added. The mixture was stirred for 90 minutes and then washed with water (4×50 mL). The combined aqueous layers were back extracted with methylene chloride (50 mL) and the pooled organic layers were dried over sodium sulfate and stripped down. Trituration with ethanol (75 mL) followed by filtration and air-drying afforded the crude product as a light yellow solid (c. 4.7 g). This material was dissolved in methylene chloride (50 mL) and cyclohexane (50 mL) was added. One teaspoon of charcoal was added, the mixture was filtered, and the product was brought down with an additional portion of cyclohexane (25 mL). Collection by filtration, air-drying, and vacuum-drying afforded colorless crystals (3.14 g, 55%).

A second precipitation from methylene chloride with cyclohexane afforded an analytical sample. Anal: Calc. [C(30)H(33)N(1)O(10)] C 63.48, H 5.86, N 2.47. Found: C 63.08, H 6.00, N 2.37. NMR (DMSO-$d_6$)): δ 1.058 (t, J=6.9 hz, 3H), 2.136 (s, 6H), 2.155 (s, 6H), 2.228 (m, 4H), 2.371 (s, 6H), 2.748 (s, 4H), 2.918 (q, J=6.9 hz, 2H), and 7.300 (s, 2H).

F. Preparation of 9-(2-(N-methyl-N-(benzyloxycarbonylmethyl)carboxamido)ethyl)-3,6-diacetoxy9-ethoxy-9H-xanthene (Ac2EtSF-505-Sar-OBn)

To a solution of sarcosine benzyl ester (0.72 g, 4.02 mmol) in methylene chloride (40 mL) was added Ac-2EtSF-526-NHS (1.82 g, 3.21 mmol) and 5% ag sodium bicarbonate solution (30 mL). The two-phase mixture was stirred rapidly for 20 hours. The layers were separated and the organic layer washed with 4×15 mL water, dried over sodium sulfate, and concentrated to 15 mL. The solution was diluted to 100 mL with cyclohexane, charcoal-treated, and reduced to 50 mL under a stream of nitrogen resulting in the precipitation of the product. Filtration followed by air-drying afforded a colorless solid (0.96 g, 47%).

Coevaporation with methylene chloride followed by extensive vacuum drying afforded an analytical sample. Anal: Calc. for [C(36)H(41)N(1)O(9)] C 68.45, H 6.54, N 2.22. Found: C 68.29, H 6.70, δ 2.07. NMR (DMSO-$d_6$) (Shows 5:2 mixture of amide bond rotamers.): δ (major and minor) 1.049 and 1.027 (t, J=6.8 hz, 3H), 1.783 and 1.700 (m,2H), 2.129 and 2.099 (s, 6H), 2.159 and 2.129 (s, 6H), 2.14 (m, 2H), 2.379 and 2.371 (s, 6H), 2.699 and 2.690 (s, 3H), 2.873 (q, J=6.8 hz, 2H), 3.958 and 3.976 (s, 2H), 5.075 and 5.019 (s, 2H), 7.266 and 7.233 (s, 2H), and 7.25–7.40 (m, 5H).

G. Preparation of 9-(2-(N-Methyl-N-(N'-succinimidyloxycarbonylmethyl)carboxamido)ethyl)-3,6-1H, H1'), 4.94 (t, J=diacetoxy-9-ethoxy-2,4,5,7-tetramethyl-9H-xanthene (Ac2EtSF-526-Sar-NHS, Structure 2d)

To a solution of Ac2EtSF-526-Sar-OBn (0.96 g, 1.52 mmol) in absolute ethanol (40 mL) was added 10% palladium on carbon (0.10 g). The mixture was stirred under balloon pressure of hydrogen for 30 minutes. The catalyst was removed by filtration and the ethanol stripped off to afford a syrupy residue.

This residue was dissolved in methylene chloride (40 mL) and N-hydroxysuccinimide (0.26 g, 2.26 mmol) and 1-(3-dimethylaminopropyl)-3-ethylcarbodiimide hydrochloride (0.59 g, 3.08 mmol) were added. The mixture was stirred for 30 minutes and then washed with water (4×15 mL). The solution was dried over sodium sulfate, concentrated to 15 mL, diluted to 100 mL with cyclohexane, charcoal treated, and reduced in volume to 50 mL under a stream of nitrogen. The product was collected by filtration, air dried, and vacuum dried to afford colorless microcrystals (0.573 g, 59%).

Coevaporation with methylene chloride followed by extensive vacuum drying at 40° C. removed traces of cyclohexane and afforded an analytical sample as an amorphous solid. NMR (DMSO-$d_6$) δ 1.043 (t, J=6.7 hz, 3H), 1.82 (m, 2H), 2.130 (s, 6H), 2.157 (s, 6H), 2.15 (m, 2H), 2.378 (s, 6H), 2.748 (s, 4H), 2.778 (s, 3H), 2.891 (q, J=6.7 hz, H), 4.327 (s, 2H), and 7.275 (s, 2H).

EXAMPLE 19

A GENERAL METHOD FOR COUPLING ALKYNYLAMINONUCLEOTIDES WITH N-HYDROXYSUCCINIMIDE ESTERS 2

PREPARATION OF FLUORESCENTLY-LABELED CHAIN TERMINATING ALKYNYLAMINO-NUCLEOTIDES 34–37

Alkynylamino-nucleotide triphosphate 49 (10 micromole, from Example 3J) was taken up in water (0.050 mL) and diluted With dimethylformamide (0.100 mL). A solution of N-hydroxysuccinimide ester 2a (12.3 mg, 21 micromole 2.1 eq. from Example 15E) in dimethylformamide (0.100 mL) was added and the mixture was stirred at 50° for 4 hours. Concentrated ammonium hydroxide (0.25 mL) was added, the reaction vessel was tightly stoppered, and heating at 50° was continued for 25 minutes. The resulting red solution was diluted to 10 mL with water and applied to a column of DEAE-Sephadex A-25-120 (1×19 cm bed) that had been equilibrated with 1.0 M pH 7.6 aqueous TEAB (50 mL) and then 0.2M pH 7.6 aqueous TEAB (50 mL). The column was eluted with a linear gradient of pH 7.6 aqueous TEAB from 0.4M (150 mL) to 0.7 M (150 mL). The column was driven at 100 mL/h collecting fractions every 3 minutes. The eluent was monitored by absorbance at 498 nm (40 AUFS). Two lesser by-product bands eluted first followed by the stronger product band with baseline resolution. The fractions estimated to contain pure product were pooled, stripped down (T<30°). co-evaporated three times with absolute ethanol, and taken up in water (0.74 mL). The solution was assayed by visible absorption (pH 8.2 50 mM aqueous Tris buffer) and lyophilized. A dilute solution of the product displayed an absorption maximum at 487.5 nm. Assuming an absorption coefficient for the product equal to that of the free dye (72,600), the yield of labeled alkynylamino-nucleotide 37 was 4.2 micromole (42%).

The above procedure produced fluorescently-labeled chain terminator 37 wherein Het is a 7-deazaguanine (k). Labeled chain terminators 34 (Het is uracil (h)), 35, (cytosine (i)), and 36 (7-deazaadenosine (j)) were prepared following similar procedures by coupling alkynylaminonucleotide triphosphates 46, 42 and 51 with N-hydroxysuccinimides 2d, 2c, and 2b, respectively. Other fluorescently-labeled nucleotide triphosphates were also prepared by the sam methods.

We claim:

1. An alkynylamino-nucleotide having the structure:

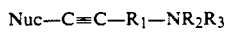

wherein
  $R_1$ is a diradical moiety of 1-20 atoms,
  $R_2$ and $R_3$ are, independently, H, $C_1$-$C_4$ alkyl or a protecting group, and Nuc is $R_4$-Het having the structure

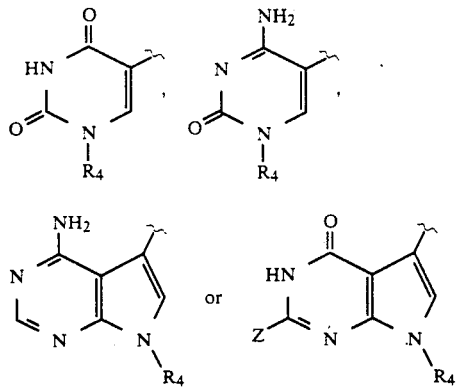

Z is H or $NH_2$, and
$R_4$ is

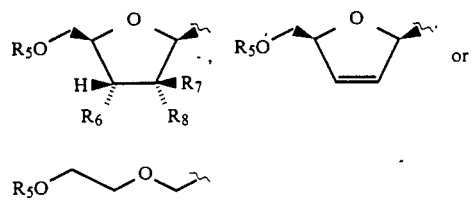

wherein
  $R_5$ is H, $PO_3H_2$, $P_2O_6H_3$, $P_3O_9H_4$ or salts thereof, and
  (i) when $R_7=R_8=H$, then $R_6=H$, OH, F, $N_3$ or $NH_2$; or
  (ii) when $R_7=H$ and $R_8=OH$, then $R_6=H$ or OH; or
  (iii) when $R_7=OH$ and $R_8=H$, then $R_6=OH$.

2. The alkynylamino-nucleotide of claim 1 wherein $R_1$ is straight chained $C_1$-$C_{10}$ alkylene moiety.

3. The alkynylamino-nucleotide of claim 1 wherein $R_1$ is —$CH_2$.

4. The alkynylamino-nucleotide of claim 1 wherein $R_2$ is H and $R_3$ is H or a protecting group.

5. The alkynylamino-nucleotide of claim 1 wherein $R_4$ is a chain-terminating sugar.

6. A labeled alkynylamino-nucleotide having the structure:

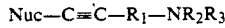

wherein
  $R_1$ is a diradical moiety of 1-20 atoms.
  $R_2$ is H, $C_1$-$C_4$ alkyl or a
  protecting group, and
  Nuc is $R_4$-Het having the structure

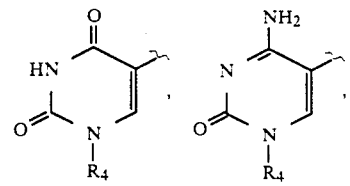

Z is H or $NH_2$, and
$R_4$ is

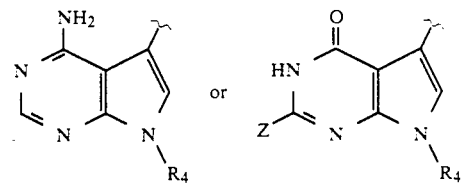

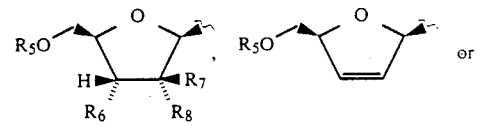

wherein
  $R_5$ is H, $PO_3H_2$, $P_2O_6H_3$, $P_3O_9H_4$ or
  (i) when $R_7=R_8=H$, then $R_6=H$, OH, R, $N_3$ or $NH_2$; or
  (ii) when $R_7=H$ and $R_8=OH$, then $R_6=H$ or OH; or
  (iii) when $R_7=OH$ and $R_8=H$, then $R_6=OH$,
and $R_{R3}$ is a reporter group.

7. The labeled alkynlamino-nucleatide of claim 6 wherein $R_3$ is a fluorescent group.

8. A process for preparing 2-thioalkoxy-6-alkoxy-7-iodo-7-deazapurines wherein 2-thioalkoxy-7-deazapurines are reacted with N-iodosuccinimide for the regioselective introduction of iodine at the 7-position and obtaining the 7-iodo regioisomer.

9. A process of preparing 7-(3-amino-1-propynyl)2',3'-dideoxyguanosine 5'-triphosphate comprising the steps of:

(A) reacting 6-methoxy-2-methylthio-7-deazapurine with 1-chloro-2-deoxy-3,5-di-O-p-toluoyl-α-D-ribofuranose in presence of sodium hydride;

(B) hydrolyzing the ester product 9 of step (A) under basic condition to diol 10;

(C) protecting the 5-OH position in diol 10 with a trityl group;

(D) removing the 3-OH group by reducing an intermediate thionocarbonate with a tin hydride reducing agent;

(E) treating the dideoxydeazapurine 12 resulting from step (D) with N-iodosuccinimide to form the 7-iodo derivative 13;

(F) reacting compound 13 with sodium thiocresolate in hexamethylphosphoramide to form the 7-deazapurin-6-one 14;

(G) treating compound 14 successively with meta-chloroperoxybenzoic acid and ammonia to obtain the 7-deazaguanosine 15;

(H) coupling N-propargyltrifluoroacetamide to the deprotected 7-iodo compound 16 to obtain 7-(3-trifluoroacetamido-1-propynyl)-2',3'-dideoxy-7-deazaguanosine; and (I) reacting the product of step (H) sequentially with phosphorous oxychloride and pyrophosphate to convert it to the 5'-triphosphate followed by deprotection.

10. A process for preparing 6-chloro-7-iodo-7-deazapurines wherein 6-chloro-7-deazapurines are reacted with iodine monochloride for the regioselective introduction of iodine at the 7-position and obtaining the 7-iodo regioisomer.

11. An improved method for preparing alkynylaminonucleotides by coupling iodo-nucleotides having an iodine atom attached to a carbon atom within the heterocyclic base with terminal alkynyl amines using a bis(triphenylphosphine)palladium dichloride/cuprous iodide catalyst, the improvement comprising the use of a tetrakis(triphenylphosphine)palladium(O)/cuprous iodide catalyst.

12. 7-Iodo-nucleotides having the structure:

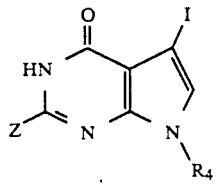

Z is H or NH$_2$, and
R$_4$ is

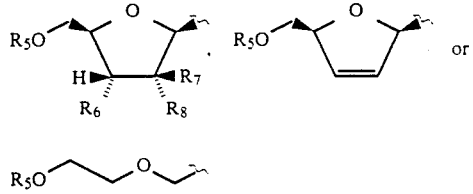

wherein
R$_5$ is H, PO$_3$H$_2$, P$_2$O$_6$H$_3$, P$_3$O$_9$H$_4$ or salts thereof, and
(i) when R$_7$=R$_8$=H, then R$_6$=H, OH, R, N$_3$ or NH$_2$; or
(ii) when R$_7$=H and R$_8$=OH, then R$_6$=H or OH; or
(iii) when R=OH and R$_8$=H, then R$_6$=OH.

* * * * *

UNITED STATES PATENT AND TRADEMARK OFFICE
CERTIFICATE OF CORRECTION

PATENT NO. : 5,047,519
DATED : September 10, 1991
INVENTOR(S) : Frank W. Hobbs, Jr. et al

It is certified that error appears in the above-indentified patent and that said Letters Patent is hereby corrected as shown below:

Title page, item [75], inventors: should read -- Frank W. Hobbs, Jr.; Anthony J. Cocuzza and George L. Trainor--

Signed and Sealed this

Seventeenth Day of October, 1995

Attest:

BRUCE LEHMAN

*Attesting Officer*   *Commissioner of Patents and Trademarks*